US011834660B2

(12) United States Patent
Freier et al.

(10) Patent No.: US 11,834,660 B2
(45) Date of Patent: Dec. 5, 2023

(54) COMPOSITIONS FOR MODULATING ATAXIN 2 EXPRESSION

(71) Applicant: Ionis Pharmaceuticals, Inc., Carlsbad, CA (US)

(72) Inventors: Susan M. Freier, San Diego, CA (US); Gene Hung, San Diego, CA (US); C. Frank Bennett, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/393,738

(22) Filed: Aug. 4, 2021

(65) Prior Publication Data

US 2022/0195430 A1 Jun. 23, 2022

Related U.S. Application Data

(60) Continuation of application No. 16/387,308, filed on Apr. 17, 2019, now Pat. No. 11,111,494, which is a division of application No. 15/127,358, filed as application No. PCT/US2015/021608 on Mar. 19, 2015, now Pat. No. 10,308,934.

(60) Provisional application No. 61/982,131, filed on Apr. 21, 2014, provisional application No. 61/955,705, filed on Mar. 19, 2014.

(51) Int. Cl.
*C12N 15/113* (2010.01)
*A61K 48/00* (2006.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/345* (2013.01); *C12N 2310/346* (2013.01)

(58) Field of Classification Search
CPC ............ C12N 15/113; C12N 2310/315; C12N 2310/321; C12N 2310/341; C12N 2310/11; A61P 25/00; A61P 25/16; A61P 25/28
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |

(Continued)

FOREIGN PATENT DOCUMENTS

| | | |
|---|---|---|
| EP | 0878543 A1 | 11/1998 |
| EP | 1752536 A1 | 2/2007 |

(Continued)

OTHER PUBLICATIONS

Verywellhealth (ALS vs. Parkinson's: Difference, Symptoms, Causes, Treatment (verywellhealth.com) downloaded on Jan. 9, 2023).*
Neurodegenerative Disorders | Peter O'Donnell Jr. Brain Institute | Condition | UT Southwestern Medical Center (utswmed.org) downloaded on Jan. 9, 2023.*
Ataxin-2 Wikipedia. Downloaded on Jul. 16, 2018 from http://en.wikipedia.org/wiki/Ataxin-2.

(Continued)

*Primary Examiner* — Terra C Gibbs
(74) *Attorney, Agent, or Firm* — McNeill Baur PLLC

(57) ABSTRACT

Disclosed herein are antisense compounds and methods for decreasing Ataxin 2 mRNA and protein expression. Such methods, compounds, and compositions are useful to treat, prevent, or ameliorate Ataxin 2 associated diseases, disorders, and conditions. Such Ataxin 2 associated diseases include spinocerebellar ataxia type 2 (SCA2), amyotropic sclerosis (ALS), and parkinsonism.

23 Claims, No Drawings

Specification includes a Sequence Listing.

(56) References Cited

U.S. PATENT DOCUMENTS 5,378,825 A 1/1995 Cook et al.
5,386,023 A 1/1995 Sanghvi et al.
5,393,878 A 2/1995 Leumann
5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,801,154 A 9/1998 Baracchini et al.
5,808,027 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'O
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,582,908 B2 6/2003 Fodor et al.
6,600,032 B1 7/2003 Manoharan et al.
6,660,720 B2 12/2003 Manoharan
6,673,535 B1 1/2004 Pulst
6,770,748 B2 8/2004 Imanishi et al.
6,844,431 B1 1/2005 Pulst
7,015,315 B1 3/2006 Cook et al.
7,053,207 B2 5/2006 Wengel et al.
7,101,993 B1 9/2006 Cook et al.
7,262,177 B2 8/2007 Ts'o et al.
7,374,927 B2 5/2008 Palma et al.
7,399,845 B2 7/2008 Seth et al.
7,427,672 B2 9/2008 Imanishi et al.
7,491,805 B2 2/2009 Vargeese et al.
7,547,684 B2 6/2009 Seth et al.
7,569,686 B1 8/2009 Bhat et al.
7,666,854 B2 2/2010 Seth et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,888,497 B2 2/2011 Bentwich et al.
7,939,677 B2 5/2011 Bhat et al.
8,022,193 B2 9/2011 Swayze et al.
8,030,467 B2 10/2011 Seth et al.
8,080,644 B2 12/2011 Wengel et al.
8,088,746 B2 1/2012 Seth et al.
8,088,904 B2 1/2012 Swayze et al.
8,106,022 B2 1/2012 Manoharan et al.
8,124,745 B2 2/2012 Allerson et al.
8,153,365 B2 4/2012 Wengel et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,501,805 B2 4/2013 Seth et al.
8,440,803 B2 5/2013 Swayze et al.
8,530,640 B2 9/2013 Seth et al.
8,546,556 B2 10/2013 Seth et al.
RE44,779 E 2/2014 Imanishi et al.
8,728,736 B2 5/2014 Leamon et al.
8,828,956 B2 9/2014 Manoharan et al.
9,005,906 B2 4/2015 Swayze et al.
9,012,421 B2 4/2015 Migawa et al.
9,127,276 B2 8/2015 Prakash et al.
9,290,760 B2 3/2016 Rajeev et al.
10,006,027 B2 6/2018 Bennett et al.
10,308,934 B2 6/2019 Freier
10,533,178 B2 1/2020 Bennett et al.
11,111,494 B2 9/2021 Freier
2001/0053519 A1 12/2001 Fodor et al.
2003/0158403 A1 8/2003 Manoharan et al.
2003/0175906 A1 9/2003 Manoharan et al.
2003/0228597 A1 12/2003 Cowsert et al.
2004/0171570 A1 9/2004 Allerson et al.
2004/0220132 A1 11/2004 Kaemmerer
2005/0026164 A1 2/2005 Zhou
2005/0042646 A1 2/2005 Davidson et al.
2005/0100885 A1 5/2005 Crooke et al.
2005/0130923 A1 6/2005 Bhat et al.

(56) References Cited

U.S. PATENT DOCUMENTS

| | | | |
|---|---|---|---|
| 2005/0209178 | A1 | 9/2005 | Pulst |
| 2005/0244851 | A1 | 11/2005 | Blume et al. |
| 2005/0255487 | A1 | 11/2005 | Khvorova et al. |
| 2006/0148740 | A1 | 7/2006 | Platenburg |
| 2006/0270727 | A1 | 11/2006 | Melander et al. |
| 2007/0031844 | A1 | 2/2007 | Khvorova et al. |
| 2007/0224624 | A1 | 9/2007 | Pulst |
| 2008/0039618 | A1 | 2/2008 | Allerson et al. |
| 2008/0113351 | A1 | 5/2008 | Naito et al. |
| 2010/0190837 | A1 | 7/2010 | Migawa et al. |
| 2010/0197762 | A1 | 8/2010 | Swayze et al. |
| 2011/0054005 | A1 | 3/2011 | Naito et al. |
| 2011/0142789 | A1 | 6/2011 | Gitler et al. |
| 2013/0130378 | A1 | 5/2013 | Manoharan et al. |
| 2013/0172399 | A1 | 7/2013 | Corey et al. |
| 2013/0225659 | A1 | 8/2013 | Bennett et al. |
| 2014/0107330 | A1 | 4/2014 | Freier et al. |
| 2014/0303238 | A1 | 10/2014 | Linsley et al. |
| 2015/0018540 | A1 | 1/2015 | Prakash et al. |
| 2015/0141320 | A1 | 5/2015 | Krieg et al. |
| 2015/0184153 | A1 | 7/2015 | Freier et al. |
| 2015/0191727 | A1 | 7/2015 | Migawa et al. |
| 2015/0259679 | A1 | 9/2015 | Bennett et al. |
| 2015/0267195 | A1 | 9/2015 | Seth et al. |
| 2015/0275212 | A1 | 10/2015 | Albaek et al. |
| 2016/0053254 | A1 | 2/2016 | Kimpe et al. |
| 2017/0175113 | A1 | 6/2017 | Bennett et al. |
| 2017/0175114 | A1 | 6/2017 | Freier et al. |
| 2019/0002887 | A1 | 1/2019 | Rigo |
| 2019/0017047 | A1 | 1/2019 | Bennett et al. |
| 2020/0056179 | A1 | 2/2020 | Freier et al. |
| 2020/0087661 | A1 | 3/2020 | Freier |
| 2022/0064639 | A1 | 3/2022 | Freier et al. |
| 2022/0162615 | A1 | 5/2022 | Rigo |

FOREIGN PATENT DOCUMENTS

| | | | |
|---|---|---|---|
| EP | 2399611 | A2 | 12/2011 |
| WO | WO 1997/42314 | | 11/1997 |
| WO | 2000015265 | A1 | 3/2000 |
| WO | 2000070039 | A1 | 11/2000 |
| WO | 2001083513 | A2 | 11/2001 |
| WO | 2003033741 | A1 | 4/2003 |
| WO | WO 2004/003201 | | 1/2004 |
| WO | 2004045543 | A2 | 6/2004 |
| WO | WO 2004/047872 | | 6/2004 |
| WO | WO 2004/070062 | | 8/2004 |
| WO | WO 2005/116204 | | 12/2005 |
| WO | WO 2005/116212 | | 12/2005 |
| WO | WO 2006/021814 | | 3/2006 |
| WO | WO 2006/131925 | | 12/2006 |
| WO | WO 2007/106407 | | 9/2007 |
| WO | WO 2008/109379 | | 9/2008 |
| WO | WO 2008/109450 | | 9/2008 |
| WO | WO 2008/152636 | | 12/2008 |
| WO | WO 2009/046141 | | 4/2009 |
| WO | 2009147684 | A2 | 12/2009 |
| WO | WO 2010/014592 | | 2/2010 |
| WO | WO 2011/006121 | | 1/2011 |
| WO | WO 2011/073326 | | 6/2011 |
| WO | WO 2011/097641 | | 8/2011 |
| WO | WO 2012/012467 | | 1/2012 |
| WO | WO 2012/079578 | | 6/2012 |
| WO | WO 2012/149438 | | 11/2012 |
| WO | 2012177639 | A2 | 12/2012 |
| WO | WO 2013/081864 | | 6/2013 |
| WO | WO 2013/162363 | | 10/2013 |
| WO | WO 2013/173645 | | 11/2013 |
| WO | WO 2015/002971 | | 1/2015 |
| WO | WO 2015/072438 | | 5/2015 |
| WO | WO 2015/143245 | | 9/2015 |
| WO | WO 2015/143246 | | 9/2015 |
| WO | WO 2017/117496 | | 7/2017 |
| WO | WO 2020/023737 | | 1/2020 |

OTHER PUBLICATIONS

Bezprozvanny et al., "Therapeutic prospects for spinocerebellar ataxia type 2 and 3." Drugs Future (2009) 34(12):1-17.

Branch et al., "A good antisense molecule is hard to find," TIBS (1998) 23:45-50.

Burke et al., "Huntingtin and DRPLA proteins selectively interact with the enzyme GAPDH." Nat. Med. (1996) 2(3):347-350.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chiu et al., "Age-Dependent Penetrance of Disease in a Transgenic Mouse Model of Familial Amyotrophic Lateral Sclerosis," Mol and Cell Neurosci, 1995, 6:349-362.

Ciosk et al., "ATX-2, the C. elegans ortholog of ataxin 2, functions in translational regulation in the germline." Development (2004) 131(19):4831-4841.

Corrado et al., "ATXN-2 CAG repeat expansions are interrupted in ALS patients." Hum. Genet. (2011) 130(4):575-580.

Crooke, ST., et al., "Antisense Drug Technology" Second Edition, CRC Press (2008) Chapters 1-28.

Deleavy et al., "Designing chemically modified oligonucleotides for targeted gene silencing" Chem Biol (2012) 19(8): 937-954.

Duvick et al., "SCA1-like disease in mice expressing wild-type ataxin-1 with a serine to aspartic acid replacement at residue 776." Neuron (2010) 67(6): 929-935.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Elden et al., "Ataxin-2 intermediate-length polyglutamine expansions are associated with increased risk for ALS." Nature (2010) 466: 1069-1075.

Elden et al., "Ataxin-2 localization in ALS and FTLD-TDP and TDP-43 localization in SCA2" Nature (2010) 466: 1069-1075 (Supplementary Information).

European partial search report for 15765851.9 dated Oct. 25, 2017.

Extended EP Search Report for 15765851.9 dated Jan. 30, 2018.

Evers et al., "Targeting Several CAG Expansion Diseases by a Single Antisense Oligonucleotide" PLoS ONE (2011) 6(9): e24308.

Frey et al., "Early and Selective Loss of Neuromuscular Synapse Subtypes with Low Sprouting Competence in Motoneuron Diseases," J Neurosci, 2000, 20(7):2534-2542.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

GenBank: NM 002973.3, *Homo sapiens* ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).

GenBank: NT_009775.17 (truncated from nucleotides 2465000 to 2616000) *Homo sapiens* chromosome 12 genomic contig, GRCh37.p13 Primary Assembly (2013) (retrieved from the internet Jun. 28, 2017: https://www.ncbi.nlm.nih.gov/nuccore/NT_009775.17?report=genbank).

GenBank: BX410018.2, BX410018 *Homo sapiens* Fetal Brain *Homo sapiens* cDNA clone CS0DF030YB07 5-PRIME, mRNA sequence; (2003) (retrieved from the internet Jun. 28, 2017: https://www.ncbi.nlm.nih.gov/nucest/BX410018.2).

Grunweller et al. "Comparison of different antisense strategies in mammalian cells using locked nucleic acids, 2'-O-methyl RNA, phosphorothioates and small interfering RNA" Nucl Ac Res (2003) 31: 185-193.

Gurney et al., "Motor Neuron Degeneration in Mice that Express a Human Cu,Zn Superoxide Dismutase Mutation," Science (1994) 264:1772-1775.

Heuvel et al., "Taking a risk: a therapeutic focus on ataxin-2 in amyotrophic lateral sclerosis?" Trends Mol Med (2014) 20(1): 25-35.

Huynh et al., "Expression of ataxin-2 in brains from normal individuals and patients with Alzheimer's disease and spinocerebellar ataxia 2." Ann. Neurol. (1999) 45: 232-241.

(56) References Cited

OTHER PUBLICATIONS

Huynh et al., "Expansion of the polyQ repeat in ataxin-2 alters its Golgi localization, disrupts the Golgi complex and causes cell death." Hum. Mol. Genet. (2003) 12: 1485-1496.
International Search Report for application PCT/US2015/021607 dated Jun. 29, 2015.
International Search Report for application PCT/US2015/021608 dated Jul. 1, 2015.
International Search Report for application PCT/US2016/069406 dated Mar. 31, 2017.
Ito et al., "Treatment with edaravone, initiated at symptom onset, slows motor decline and decreases SOD1 deposition in ALS mice," Experimental Neurology, 2008, 213:448-455.
Kim et al., "Importance of low-range CAG expansion and CAA interruption in SCA2 Parkinsonism." Arch. Neurol. (2007) 64(10): 1510-1518.
Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.
Lajoie et al., "Formation and toxicity of soluble polyglutamine oligomers in living cells." PLoS One (2010) 5(12): e15245 1-15.
Lou Gehrig's Disease (ALS): Prevention | Florida Hospital. Downloaded on Jul. 16, 2018 from https://www.floridahospital.com/lou-gehrigs-disease-als/prevention-lou-gehrigs-disease-als.
Lovett-Racke et al., Therapeutic Potential of Small Interfering RNA for Central Nervous System Diseases. Archives of Neurobiology (2005) 62:1810-1813.
Magana et al., "Spinocerebellar ataxia type 2: clinical presentation, molecular mechanisms, and therapeutic perspectives" Mol Neurobiol (2013) 47(1): 90-104.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
New England Biolabs 1998/99 Catalog (cover page and pp. 121 and 284).
Nonhoff et al., "Ataxin-2 interacts with the DEAD/H-box RNA helicase DDX6 and interferes with P-bodies and stress granules." Mol. Biol. Cell (2007) 18(4):1385-1396.
Nonis et al., "Ataxin-2 associates with the endocytosis complex and affects EGF receptor trafficking" Cell Signal (2008) 20(10):1725-1739.
Parkinson's Disease—Symptoms and causes—Mayo Clinic. Downloaded on Jul. 16, 2018 from https://www.mayoclinic.org/diseases-conditions/parkinsons-disease/symptoms-causes/syc-20376055.
Philips et al., "Rodent Models of Amyotrophic Lateral Sclerosis," Curr Protoc Pharmacol, 2015, 69: 1-21.
Pulst S.M. (ed.) "Inherited Ataxias: An Introduction" Genetics of Movement Disorders. Elsevier, Inc., Amsterdam, published Oct. 3, 2002, pp. 19-34.
Pulst S.M., "Rare mendelian diseases: pathways to therapy development" Oral presentation, American Academy of Neurology Annual Meeting, Philadelphia, PA, Apr. 29, 2014.
Pun et al., "Selective Vulnerability and Pruning of Phasic Motoneuron Axons in Motoneuron Disease Alleviated by CTNF," Nat Neurosci, 2006, 9:408-419.
Ramachandran, P. "RNA interference therapy for the Spinocerebellar ataxias." Thesis, May 2014, University of Iowa, pp. 1-140.
Reynolds et al., "Rational siRNA design for RNA interference" Nature Biotechnology (2004) 22(3):326-330.
Ross et al., "Ataxin-2 repeat-length variation and neurodegeneration." Hum. Mol. Genet. (2011) 20(16): 3207-3212.
Sanghvi et al., "Heterocyclic Base Modifications in Nucleic Acids and Their Applications in Antisense Oligonucleotides" Antisense Research and Applications (1993) pp. 273-288.
Satterfield et al., "Ataxin-2 and its *Drosophila* homolog, ATX2, physically assemble with polyribosomes." Hum. Mol. Genet. (2006) 15(16):2523-2532.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al., Antisense oligonucleotides for the treatment of spinocerebellar ataxia type 2 (SCA2), 5th Ataxia Investigators Meeting (AIM) meeting abstract presented Mar. 20, 2014.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Scoles et al., "ATXN2 Is Regulated by a Promoter Associated Antisense Long Noncoding RNA (lncRNA)" Neurology (2013) 80: P05030.
Seth et al., "Short Antisense Oligonucleotides with Novel 2'-4' Conformationally Restricted Nucleoside Analogues Show Improved Potency Without Increased Toxicity in Animals." J Med Chem (2009) 52:10-13.
Shen et al., "Research on (CAG)n mutation detection of Spinocerebellar ataxia type 2" Chinese J Int Med (2000) 39(4): 259-261.
Shibata et al., "A novel protein with RNA-binding motifs interacts with ataxin-2." Hum. Mol. Genet. (2000) 9(9): 1303-1313.
Takei et al., "Edaravone and its Clinical Development for Amyotrophic Lateral Sclerosis," Amyotrophic Lateral Sclerosis and Frontotemporal Degeneration, 2017, 18:5-10.
Van Blitterswijk et al., "Ataxin-2 as potential disease modifier in C9ORF72 expansion carriers" Neurobiology of Aging (2014) 35: e13-e17.
Van Damme et al., "Expanded ATXN2 CAG repeat size in ALS identifies genetic overlap between ALS and SCA2." Neurology (2011) 76(24):2066-2072.
Woolf et al. "Specificity of antisense oligonucleotides in vivo" PNAS (1992) 89:7305-7309.
Yamanaka et al., "Transcription factor sequestration by polyglutamine proteins." Methods Mol. Biol. (2010) 648:215-229.
Zangemeister-Wittke et al., "A novel bispecific antisense oligonucleotide inhibiting both bcl-2 and bcl-xL expression efficiently induces apoptosis in tumor cells" Clin Cancer Res (2000) 6: 2547-2555.
European partial search report for 21187734.5 dated Mar. 4, 2022, 18 pages.
Extended EP Search Report for 19841474.0 dated Apr. 18, 2023, 6 pages.
Extended EP Search Report for 21187734.5 dated Jul. 25, 2022, 20 pages.

* cited by examiner

COMPOSITIONS FOR MODULATING ATAXIN 2 EXPRESSION

SEQUENCE LISTING

The present application is being filed along with a Sequence Listing in electronic format. The Sequence Listing is provided as a file entitled BIOL0239USC1SEQ_ST25.txt created Apr. 17, 2019, which is 232 Kb in size. The information in the electronic format of the sequence listing is incorporated herein by reference in its entirety.

FIELD

Provided are compositions and methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 by inhibiting expression of Ataxin 2 in an animal.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935) and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., *Development,* 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein CIN85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating such neurodegenerative diseases. It is therefore an object herein to provide methods for the treatment of such diseases.

SUMMARY

Provided herein are methods, compounds, and compositions for modulating expression of Ataxin 2 (ATXN2) mRNA and protein. In certain embodiments, compounds useful for modulating expression of Ataxin 2 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, Ataxin 2 mRNA levels are reduced. In certain embodiments, Ataxin 2 protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such Ataxin 2 related diseases, disorders, and conditions are neurodegenerative diseases. In certain embodiments, such neurodegenerative diseases, disorders, and conditions include spinocerebellar ataxia type 2 (SCA2), amyotrophic lateral sclerosis (ALS), and parkinsonism.

Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: ataxia, speech and swallowing difficulties, rigidity, tremors, ophthalmoplegia, saccadic slowing, peripheral neuropathy, atrophy, dystonia, chorea, and dementia.

In certain embodiments, methods of treatment include administering an Ataxin 2 antisense compound to an individual in need thereof. In certain embodiments, methods of treatment include administering an Ataxin 2 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and"

means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-$OCH_2CH_2$—$OCH_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Ataxin 2", it is implied that the Ataxin 2 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Ataxin 2" means the mammalian gene Ataxin 2 (ATXN2), including the human gene Ataxin 2 (ATXN2). Human Ataxin 2 has been mapped to human chromosome 12q24.1.

"Ataxin 2 associated disease" means any disease associated with any Ataxin 2 nucleic acid or expression product thereof. Such diseases may include a neurodegenerative disease. Such neurodegenerative diseases may include spinocerebellar ataxia type 2 (SCA2), amyotrophic lateral sclerosis (ALS), and parkinsonism.

"Ataxin 2 mRNA" means any messenger RNA expression product of a DNA sequence encoding Ataxin 2.

"Ataxin 2 nucleic acid" means any nucleic acid encoding Ataxin 2. For example, in certain embodiments, an Ataxin 2 nucleic acid includes a DNA sequence encoding Ataxin 2, an RNA sequence transcribed from DNA encoding Ataxin 2 (including genomic DNA comprising introns and exons), and an mRNA sequence encoding Ataxin 2. "Ataxin 2 mRNA" means an mRNA encoding an Ataxin 2 protein.

"Ataxin 2 protein" means the polypeptide expression product of an Ataxin 2 nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having an Ataxin 2 associated disease" means identifying an animal having been diagnosed with an Ataxin 2 associated disease or predisposed to develop an Ataxin 2 associated disease. Individuals predisposed to develop an Ataxin 2 associated disease include those having one or more risk factors for developing an Ataxin 2 associated disease, including, growing older, having a personal or family history, or genetic predisposition of one or more Ataxin 2 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Ataxin 2" means reducing the level or expression of an Ataxin 2 mRNA and/or protein. In certain embodiments, Ataxin 2 mRNA and/or protein levels are inhibited in the presence of an antisense compound targeting Ataxin 2, including an antisense oligonucleotide targeting Ataxin 2, as compared to expression of Ataxin 2 mRNA and/or protein levels in the absence of an Ataxin 2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-$CH_2$—O-2') LNA, (B) β-D-Methyleneoxy (4'-$CH_2$—O-2') LNA, (C) Ethyleneoxy (4'-$(CH_2)_2$—O-2') LNA, (D) Aminooxy (4'-$CH_2$—O—N(R)-2') LNA and (E) Oxyamino (4'-$CH_2$—N(R)—O-2') LNA, as depicted below.

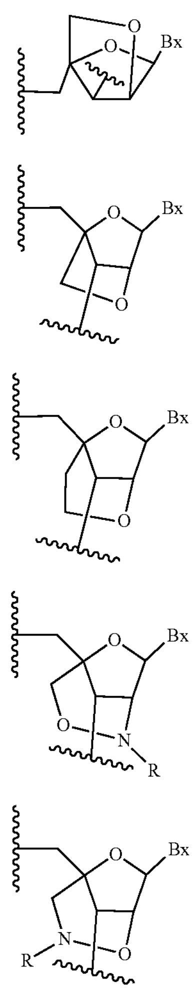

(A) (B) (C) (D) (E)

As used herein, LNA compounds include, but are not limited to, compounds having at least one bridge between the 4' and the 2' position of the sugar wherein each of the bridges independently comprises 1 or from 2 to 4 linked groups independently selected from —$[C(R_1)(R_2)]_n$—, —$C(R_1)$═$C(R_2)$—, —$C(R_1)$═N—, —C(═$NR_1$)—, —C(═O)—, —C(═S)—, —O—, —$Si(R_1)_2$—, —$S(═O)_x$— and —$N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —$[C(R_1)(R_2)]_n$—, —$[C(R_1)(R_2)]_n$O—, —$C(R_1R_2)$—$N(R_1)$—O— or —$C(R_1R_2)$—O—$N(R_1)$—. Furthermore, other bridging groups encompassed with the definition of LNA are 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—$N(R_1)$-2' and 4'-$CH_2$—$N(R_1)$—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicylic sugar moiety having an ethylene bridging group in this position, the term ethyleneoxy (4'-$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Ataxin 2 is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods, compounds, and compositions for inhibiting Ataxin 2 mRNA and protein expression. Certain embodiments provide methods, compounds, and composition for decreasing Ataxin 2 mRNA and protein levels.

Certain embodiments provide antisense compounds targeted to an Ataxin 2 nucleic acid. In certain embodiments, the Ataxin 2 nucleic acid is the sequence set forth in GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

Certain embodiments provide methods for the treatment, prevention, or amelioration of diseases, disorders, and conditions associated with Ataxin 2 in an individual in need thereof. Also contemplated are methods for the preparation of a medicament for the treatment, prevention, or amelioration of a disease, disorder, or condition associated with Ataxin 2. Ataxin 2 associated diseases, disorders, and conditions include neurodegenerative diseases. In certain embodiments, Ataxin 2 associated diseases include spinocerebellar ataxia type 2 (SCA2), amyotrophic lateral sclerosis (ALS), and parkinsonism.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 11-165.

In certain embodiments the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1, SEQ ID NO: 2, or SEQ ID NO: 3.

In certain embodiments, the compound is a single-stranded modified oligonucleotide.

In certain embodiments, at least one internucleoside linkage of the modified oligonucleotide is a modified internucleoside linkage.

In certain embodiments, at least one modified internucleoside linkage is a phosphorothioate internucleoside linkage.

In certain embodiments, each modified internucleoside linkage is a phosphorothioate internucleoside linkage.

In certain embodiments, at least one internucleoside linkage is a phosphodiester internucleoside linkage.

In certain embodiments, at least one internucleoside linkage is a phosphorothioate linkage and at least one internucleoside linkage is a phosphodiester linkage.

In certain embodiments, at least one nucleoside comprises a modified nucleobase.

In certain embodiments, the modified nucleobase is a 5-methylcytosine.

In certain embodiments, at least one nucleoside of the modified oligonucleotide comprises a modified sugar.

In certain embodiments, at least one modified sugar is a bicyclic sugar.

In certain embodiments, the bicyclic sugar comprises a a chemical link between the 2' and 4' position of the sugar 4'-CH2-N(R)—O-2' bridge wherein R is, independently, H, C1-C12 alkyl, or a protecting group.

In certain embodiments, the bicyclic sugar comprises a 4'-CH2-N(R)—O-2' bridge wherein R is, independently, H, C1-C12 alkyl, or a protecting group.

In certain embodiments, at least one modified sugar comprises a 2'-O-methoxyethyl group.

In certain embodiments, the modified sugar comprises a 2'-$O(CH_2)_2$—$OCH_3$ group.

In certain embodiments, the modified oligonucleotide comprises:

a gap segment consisting of 10 linked deoxynucleosides;

a 5' wing segment consisting of 5 linked nucleosides; and a 3' wing segment consisting of 5 linked nucleosides;

wherein the gap segment is positioned between the 5' wing segment and the 3' wing segment and wherein each nucleoside of each wing segment comprises a modified sugar.

In certain embodiments, the modified oligonucleotide consists of 20 linked nucleosides.

Certain embodiments provide compositions comprising any compound described herein or salt thereof and at least one of a pharmaceutically acceptable carrier or diluent.

Certain embodiments provide methods comprising administering to an animal any compound or composition described herein.

In certain embodiments, the animal is a human.

In certain embodiments, administering the compound prevents, treats, ameliorates, or slows progression of an Ataxin 2 associated disease, disorder or condition.

In certain embodiments, the Ataxin 2 disease, disorder or condition spinocerebellar ataxia type 2 (SCA2), amyotrophic lateral sclerosis (ALS), and parkinsonism.

Certain embodiments provide use of any of the compounds or compositions of described herein for the manufacture of a medicament for treating a neurodegenerative disorder.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be “antisense” to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an Ataxin 2 nucleic acid is 12 to 30 subunits in length. In certain embodiments, an antisense compound targeted to an Ataxin 2 nucleic acid is 12 to 25 subunits in length. In certain embodiments, an antisense compound targeted to an Ataxin 2 nucleic acid is 12 to 22 subunits in length. In certain embodiments, an antisense compound targeted to an Ataxin 2 nucleic acid is 14 to 20 subunits in length. In certain embodiments, an antisense compound targeted to an Ataxin 2 nucleic acid is 15 to 25 subunits in length. In certain embodiments, an antisense compound targeted to an Ataxin 2 nucleic acid is 18 to 22 subunits in length. In certain embodiments, an antisense compound targeted to an Ataxin 2 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to an Ataxin 2 nucleic acid is 12 subunits in length. In certain embodiments, an antisense compound targeted to an Ataxin 2 nucleic acid is 13 subunits in length. In certain embodiments, an antisense compound targeted to an Ataxin 2 nucleic acid is 14 subunits in length. In certain embodiments, an antisense compound targeted to an Ataxin 2 nucleic acid is 15 subunits in length. In certain embodiments, an antisense compound targeted to an Ataxin 2 nucleic acid is 16 subunits in length. In certain embodiments, an antisense compound targeted to an Ataxin 2 nucleic acid is 17 subunits in length. In certain embodiments, an antisense compound targeted to an Ataxin 2 nucleic acid is 18 subunits in length. In certain embodiments, an antisense compound targeted to an Ataxin 2 nucleic acid is 19 subunits in length. In certain embodiments, an antisense compound targeted to an Ataxin 2 nucleic acid is 20 subunits in length. In certain embodiments, an antisense compound targeted to an Ataxin 2 nucleic acid is 21 subunits in length. In certain embodiments, an antisense compound targeted to an Ataxin 2 nucleic acid is 22 subunits in length. In certain embodiments, an antisense compound targeted to an Ataxin 2 nucleic acid is 23 subunits in length. In certain embodiments, an antisense compound targeted to an Ataxin 2 nucleic acid is 24 subunits in length. In certain embodiments, an antisense compound targeted to an Ataxin 2 nucleic acid is 25 subunits in length. In certain embodiments, an antisense compound targeted to an Ataxin 2 nucleic acid is 26 subunits in length. In certain embodiments, an antisense compound targeted to an Ataxin 2 nucleic acid is 27 subunits in length. In certain embodiments, an antisense compound targeted to an Ataxin 2 nucleic acid is 28 subunits in length. In certain embodiments, an antisense compound targeted to an Ataxin 2 nucleic acid is 29 subunits in length. In certain embodiments, an antisense compound targeted to an Ataxin 2 nucleic acid is 30 subunits in length. In certain embodiments, the antisense compound targeted to an Ataxin 2 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to an Ataxin 2 nucleic acid may be shortened or truncated. For example, a single subunit may be deleted from the 5' end (5' truncation), or alternatively from the 3' end (3' truncation). A shortened or truncated antisense compound targeted to an Ataxin 2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an Ataxin 2 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2 and 4'-$CH_2$—O—$CH_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Ataxin 2 include, without limitation, the following: GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Ataxin 2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Ataxin 2 mRNA levels are indicative of inhibition of Ataxin 2 expression. Reductions in levels of an Ataxin 2 protein are also indicative of inhibition of target mRNA expression. Phenotypic changes are indicative of inhibition of Ataxin 2 expression. Improvement in neurological function is indicative of inhibition of Ataxin 2 expression. Improved motor function and memory are indicative of inhibition of Ataxin 2 expression.

Hybridization

In some embodiments, hybridization occurs between an antisense compound disclosed herein and an Ataxin 2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Ataxin 2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Ataxin 2 nucleic acid).

Non-complementary nucleobases between an antisense compound and an Ataxin 2 nucleic acid may be tolerated provided that the antisense compound remains able to specifically hybridize to a target nucleic acid. Moreover, an antisense compound may hybridize over one or more segments of an Ataxin 2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Ataxin 2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Ataxin 2 nucleic acid, or a target region, or a target segment or target sequence thereof. As used herein, "fully complementary"

means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Ataxin 2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Ataxin 2 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

MODIFICATIONS

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Ataxin 2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.,* 2009, 74, 118-134); and 4'-$CH_2$—C—(═$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U S. A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(═O)—, —C(═$NR_a$)—, —C(═S)—, —O—, —$Si(R_a)_2$—, —S(═O)—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

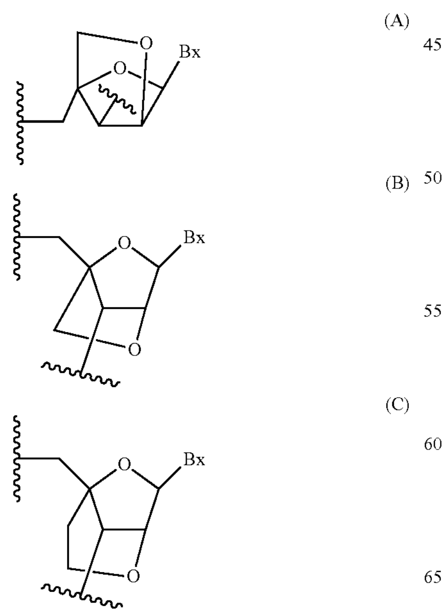

-continued (D)

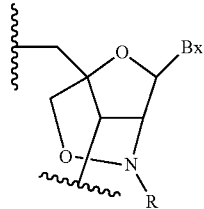

(E)

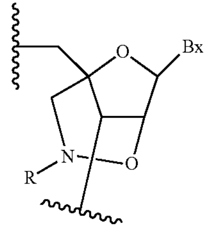

(F)

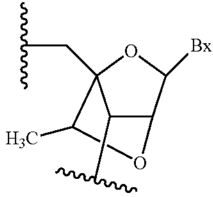

(G)

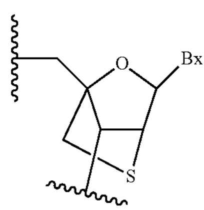

(H)

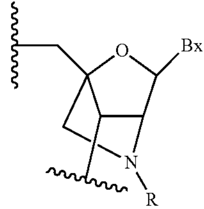

(I)

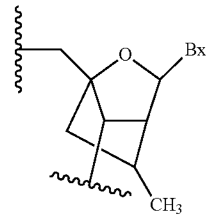

(J)

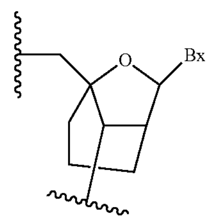

wherein Bx is the base moiety and R is independently H, a protecting group or $C_1$-$C_{12}$ alkyl.

In certain embodiments, bicyclic nucleosides are provided having Formula I:

I

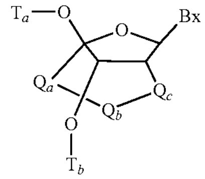

wherein:

Bx is a heterocyclic base moiety;

$Q_a$-$Q_b$-$Q_c$- is —$CH_2$—$N(R_c)$—$CH_2$—, —C(=O)—$N(R_c)$—$CH_2$—, —$CH_2$—O—$N(R_c)$—, —$CH_2$—$N(R_c)$—O— or —$N(R_c)$—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

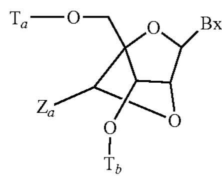

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

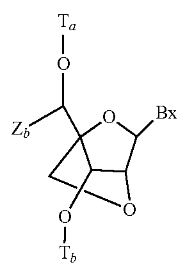

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

IV

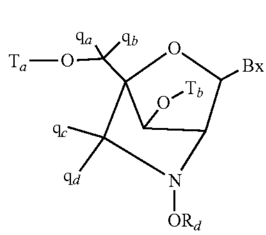

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

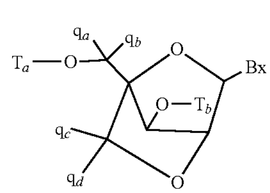

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ of are each, independently, hydrogen, halogen, $C_1$-$C_{12}$ alkyl, substituted $C_1$-$C_{12}$ alkyl, $C_2$-C12 alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

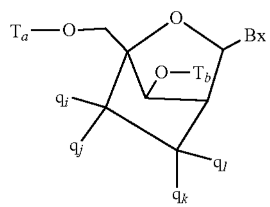

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

VII

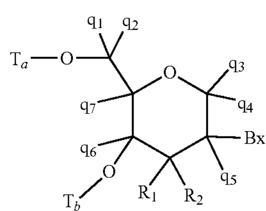

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an Ataxin 2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an Ataxin 2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Ataxin 2 nucleic acids can be tested in vitro in a variety of cell types. Cell types used for such analyses are available from commercial vendors (e.g. American Type Culture Collection, Manassus, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of an Ataxin 2 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an Ataxin 2 nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of Ataxin 2 nucleic acids can be assessed by measuring Ataxin 2 protein levels. Protein levels of Ataxin 2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Ataxin 2 and produce phenotypic changes, such as, improved motor function and cognition. In certain embodiments, motor function is measured by walking initiation analysis, rotarod, grip strength, pole climb, open field performance, balance beam, hindpaw footprint testing in the animal.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Ataxin 2 nucleic acid expression are measured.

Certain Indications

In certain embodiments, provided herein are methods, compounds, and compositions of treating an individual comprising administering one or more pharmaceutical compositions described herein. In certain embodiments, the individual has a neurodegenerative disease. In certain embodiments, the individual is at risk for developing a neurodegenerative disease, including, but not limited to, spinocerebellar ataxia type 2 (SCA2), amyotrophic lateral sclerosis (ALS), and parkinsonism. In certain embodiments, the individual has been identified as having an Ataxin 2 associated disease. In certain embodiments, provided herein are methods for prophylactically reducing Ataxin 2 expression in an individual. Certain embodiments include treating an individual in need thereof by administering to an individual a therapeutically effective amount of an antisense compound targeted to an Ataxin 2 nucleic acid.

In one embodiment, administration of a therapeutically effective amount of an antisense compound targeted to an Ataxin 2 nucleic acid is accompanied by monitoring of Ataxin 2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to an Ataxin 2 nucleic acid results in reduction of Ataxin 2 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to an Ataxin 2 nucleic acid results in improved motor function in an animal. In certain embodiments, administration of an Ataxin 2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Ataxin 2 are used for the preparation of a medicament for treating a patient suffering or susceptible to a neurodegenerative disease including spinocerebellar ataxia type 2 (SCA2), amyotrophic lateral sclerosis (ALS), and parkinsonism.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Ataxin 2 in HepG2 Cells by MOE Gapmers Antisense oligonucleotides were designed targeting an ataxin 2 nucleic acid and were tested for their effects on ataxin 2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and ataxin 2 mRNA levels were measured by quantitative real-time PCR. Human primer probe set RTS3642 (forward sequence ACCAAAGAGTAGTTAATGGAGGTGTTC, designated herein as SEQ ID NO: 5; reverse sequence AGAAGGTGGGCGAGAGGAA, designated herein as SEQ ID NO: 6; probe sequence CTGGCCATCGCCTTGCCCA, designated herein as SEQ ID NO: 7) was used to measure mRNA levels. Ataxin 2 mRNA levels were adjusted according to total RNA content, as measured by RIBOGREEN®. Results are presented as percent inhibition of ataxin 2, relative to untreated control cells.

The chimeric antisense oligonucleotides in the Tables below were designed as 5-10-5 MOE gapmers. The gapmers are 20 nucleosides in length, wherein the central gap segment is comprised of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. “Start site” indicates the 5'-most nucleoside to which the gapmer is targeted in the human gene sequence. “Stop site” indicates the 3'-most nucleoside to which the gapmer is targeted human gene sequence. Each gapmer listed in the Tables below is targeted to either the human ataxin 2 mRNA, designated herein as SEQ ID NO: 1 (GENBANK Accession No. NM_002973.3) or the human ataxin 2 genomic sequence, designated herein as SEQ ID NO: 2 (the complement of GENBANK Accession No. NT_009775.17 truncated from nucleotides 2465000 to 2616000). Some oligonucleotides do not target either SEQ ID NO: 1 or SEQ ID NO: 2, but instead target a variant gene sequence, SEQ ID NO: 3 (GENBANK Accession No. BX410018.2). ‘n/a’ indicates that the antisense oligonucleotide does not target that particular gene sequence with 100% complementarity.

TABLE 1

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564118 | 606 | 625 | CCGGCTCGCACGCCGGGCGG | 57 | 2596 | 2615 | 11 |
| 564119 | 612 | 631 | CATACACCGGCTCGCACGCC | 63 | 2602 | 2621 | 12 |
| 564120 | 637 | 656 | GGCTTCAGCGACATGGTGAG | 78 | 2627 | 2646 | 13 |
| 564121 | 880 | 899 | CGACCTCTGCCCAGGCCGGG | 67 | n/a | n/a | 14 |
| 564122 | 935 | 954 | TGCATAGATTCCATCAAAAG | 90 | 47454 | 47473 | 15 |
| 564123 | 959 | 978 | AAGTATATGAACCATCCTCA | 67 | 47478 | 47497 | 16 |
| 564124 | 997 | 1016 | TTCACTTGTACTTCACATTT | 85 | 48696 | 48715 | 17 |
| 564125 | 1084 | 1103 | TCTGTACTTTTCTCATGTGC | 88 | 49258 | 49277 | 18 |
| 564126 | 1090 | 1109 | CTGGATTCTGTACTTTTCTC | 89 | 49264 | 49283 | 19 |
| 564127 | 1123 | 1142 | CTCTCCATTATTTCTTCACG | 92 | 49297 | 49316 | 20 |
| 564128 | 1168 | 1187 | TCTTTAAACTGTACCACAAC | 86 | 49342 | 49361 | 21 |
| 564129 | 1210 | 1229 | GAGTCAGTAAAAGCATCTCT | 84 | n/a | n/a | 22 |
| 564130 | 1264 | 1283 | CAGGGCTCCAGGTCCTTCTC | 83 | 76401 | 76420 | 23 |
| 564131 | 1270 | 1289 | GCATCCCAGGGCTCCAGGTC | 86 | 76407 | 76426 | 24 |
| 564132 | 1363 | 1382 | TCTTCATTATATCGAAACAT | 84 | 80718 | 80737 | 25 |
| 564133 | 1477 | 1496 | GCTAACTGGTTTGCCCTTGC | 98 | 81637 | 81656 | 26 |
| 564134 | 1556 | 1575 | GTATTTTTCTTCCTCACTCC | 82 | 81716 | 81735 | 27 |
| 564135 | 1562 | 1581 | TGCTGTGTATTTTTCTTCCT | 89 | 81722 | 81741 | 28 |
| 564136 | 1748 | 1767 | GAAATCTGAAGTGTGAGAAG | 61 | 83359 | 83378 | 29 |
| 564137 | 1789 | 1808 | CCTCCATTAACTACTCTTTG | 90 | 83400 | 83419 | 30 |
| 564138 | 1795 | 1814 | GGAACACCTCCATTAACTAC | 66 | n/a | n/a | 31 |
| 564139 | 1807 | 1826 | GGCGATGGCCAGGGAACACC | 95 | 85303 | 85322 | 32 |
| 564140 | 1844 | 1863 | GTAGCGAGAAGGTGGGCGAG | 88 | 85340 | 85359 | 33 |
| 564141 | 1862 | 1881 | AGAGTTGGGACCTGACTGGT | 84 | 85358 | 85377 | 34 |
| 564142 | 1868 | 1887 | TGGAAGAGAGTTGGGACCTG | 84 | 85364 | 85383 | 35 |
| 564143 | 1963 | 1982 | GGAGCTGGAGAACCATGAGC | 91 | 85459 | 85478 | 36 |
| 564144 | 1969 | 1988 | GAGACAGGAGCTGGAGAACC | 86 | 85465 | 85484 | 37 |
| 564145 | 2101 | 2120 | TTGTGGGATACAAATTCTAG | 56 | 88211 | 88230 | 38 |
| 564146 | 2185 | 2204 | GGAACCCCACTGACCACTGA | 70 | n/a | n/a | 39 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564147 | 2401 | 2420 | TCTTGAAGCCTGGAATCTTT | 61 | 91671 | 91690 | 40 |
| 564148 | 2560 | 2579 | AACCTAAAATCATTCTTAAA | 21 | n/a | n/a | 41 |
| 564149 | 2596 | 2615 | AGTTGATCCATAGATTCAGA | 74 | 112905 | 112924 | 42 |
| 564150 | 2704 | 2723 | CTGGTACAGTTGCTGCTGCT | 91 | 113013 | 113032 | 43 |
| 564151 | 2710 | 2729 | CTGCCACTGGTACAGTTGCT | 85 | 113019 | 113038 | 44 |
| 564152 | 2899 | 2918 | TTTGCATTGGGATTCAATGT | 76 | 114859 | 114878 | 45 |
| 564153 | 2938 | 2957 | GAAGGCTTTGGCTGAGAGAA | 66 | n/a | n/a | 46 |
| 564154 | 2944 | 2963 | GTAGTAGAAGGCTTTGGCTG | 71 | n/a | n/a | 47 |
| 564155 | 2995 | 3014 | TGACCCACCATAGATGGGCT | 38 | 115850 | 115869 | 48 |
| 564156 | 3097 | 3116 | GGTATTGGGTATAAAGGTTG | 57 | n/a | n/a | 49 |
| 564157 | 3103 | 3122 | GTCATAGGTATTGGGTATAA | 76 | 116339 | 116358 | 50 |
| 564158 | 3331 | 3350 | GGATGCTGAGACTGATAATG | 54 | n/a | n/a | 51 |
| 564159 | 3337 | 3356 | ACATGAGGATGCTGAGACTG | 63 | n/a | n/a | 52 |
| 564160 | 3472 | 3491 | AATTTGGGACATGCATACAT | 23 | n/a | n/a | 53 |
| 564161 | 3490 | 3509 | GTCTCCTTGTTGTATGGTAA | 76 | 136963 | 136982 | 54 |
| 564162 | 3658 | 3677 | TGAACAGGACTGGGTGCAGG | 41 | 144433 | 144452 | 55 |
| 564163 | 3715 | 3734 | GACTGCTGCTGTGGACTGGC | 69 | 145447 | 145466 | 56 |
| 564164 | 3903 | 3922 | CTGACTGTACATGAGCCTGA | 50 | 147818 | 147837 | 57 |
| 564165 | 3909 | 3928 | CCATTCCTGACTGTACATGA | 69 | 147824 | 147843 | 58 |
| 564166 | 3927 | 3946 | CAGTTGGATGAGAAGGAACC | 58 | 147842 | 147861 | 59 |
| 564167 | 3933 | 3952 | CATGGGCAGTTGGATGAGAA | 29 | 147848 | 147867 | 60 |
| 564168 | 3971 | 3990 | ACCGCCGGGTGGCTGTGTCG | 40 | 147886 | 147905 | 61 |
| 564169 | 3993 | 4012 | TTTGAGCGAGGGCGGCCTGG | 19 | 147908 | 147927 | 62 |
| 564170 | 4005 | 4024 | GCTGTAGTGCACTTTGAGCG | 73 | 147920 | 147939 | 63 |
| 564171 | 4017 | 4036 | AGACTGGAATGGGCTGTAGT | 58 | 147932 | 147951 | 64 |
| 564172 | 4029 | 4048 | GCGCTGTTGTCGAGACTGGA | 74 | 147944 | 147963 | 65 |
| 564173 | 4035 | 4054 | GGAAATGCGCTGTTGTCGAG | 69 | 147950 | 147969 | 66 |
| 564174 | 4064 | 4083 | GGCTTGTACTGAAGGGTGCG | 23 | n/a | n/a | 67 |
| 564175 | 4070 | 4089 | GTGGTGGGCTTGTACTGAAG | 35 | n/a | n/a | 68 |
| 564176 | 4076 | 4095 | CTGTTGGTGGTGGGCTTGTA | 22 | 148827 | 148846 | 69 |
| 564177 | 4082 | 4101 | CAACTGCTGTTGGTGGTGGG | 39 | 148833 | 148852 | 70 |
| 564178 | 4088 | 4107 | GCCTTACAACTGCTGTTGGT | 62 | 148839 | 148858 | 71 |
| 564179 | 4106 | 4125 | TTCGGTTCCTCCAGGGCAGC | 72 | 148857 | 148876 | 72 |
| 564180 | 4166 | 4185 | TTCTAGTTTTCTGTGCTTCC | 72 | 148917 | 148936 | 73 |
| 564181 | 4367 | 4386 | AATAAATAACTTCCAGTTTC | 59 | 149118 | 149137 | 74 |
| 564182 | 4429 | 4448 | GAATCACTCTTGTTACTTCT | 78 | 149180 | 149199 | 75 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564183 | 4435 | 4454 | CAGCAAGAATCACTCTTGTT | 85 | 149186 | 149205 | 76 |
| 564184 | 4551 | 4570 | TTTATAAATAATAATCCGTC | 4 | 149302 | 149321 | 77 |
| 564185 | 4593 | 4612 | AAGTTGAACCACTGTAGACA | 60 | 149344 | 149363 | 78 |
| 564186 | n/a | n/a | ATCGGCCACCACCCGCGCGC | 55 | 3683 | 3702 | 79 |
| 564187 | n/a | n/a | CAAAGGGTTAATTAGGATCT | 66 | 85057 | 85076 | 80 |
| 564188 | n/a | n/a | CCCAAAGGGTTAATTAGGAT | 94 | 85059 | 85078 | 81 |
| 564189 | n/a | n/a | AGGACAGTCATTTGATTTGT | 72 | 85166 | 85185 | 82 |
| 564190 | n/a | n/a | CTTTGAGGACAGTCATTTGA | 70 | 85171 | 85190 | 83 |
| 564191 | n/a | n/a | CTGACAGAACAAATGATATG | 17 | 85284 | 85303 | 84 |
| 564192 | n/a | n/a | TATTGGGTATAAAGGCTTGA | 31 | 116331 | 116350 | 85 |
| 564193 | n/a | n/a | GGTATTGGGTATAAAGGCTT | 78 | 116333 | 116352 | 86 |
| 564194 | n/a | n/a | CTCTTTTACGCATACAGGCA | 74 | 147789 | 147808 | 87 |
| 564195 | n/a | n/a | AGGAAGGCCAACTGAGTCCT | 70 | 148258 | 148277 | 88 |

TABLE 2

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564158 | 3331 | 3350 | GGATGCTGAGACTGATAATG | 61 | n/a | n/a | 51 |
| 564196 | 70 | 89 | GGTCAGACGGAAGCAGAACG | 9 | 2060 | 2079 | 89 |
| 564197 | 218 | 237 | CCACCTGGCTGCGGCGAAGC | 12 | 2208 | 2227 | 90 |
| 564198 | 392 | 411 | GCCGTTGCCGTTGCTACCAA | 80 | 2382 | 2401 | 91 |
| 564199 | 616 | 635 | GGCCCATACACCGGCTCGCA | 79 | 2606 | 2625 | 92 |
| 564200 | 636 | 655 | GCTTCAGCGACATGGTGAGG | 81 | 2626 | 2645 | 93 |
| 564201 | 732 | 751 | GGACATTGGCAGCCGCGGGC | 83 | 2722 | 2741 | 94 |
| 564202 | 929 | 948 | GATTCCATCAAAAGAAATCG | 67 | n/a | n/a | 95 |
| 564203 | 969 | 988 | CAACTGATGTAAGTATATGA | 45 | 47488 | 47507 | 96 |
| 564204 | 1053 | 1072 | CCAAATCACACTTCGGACTG | 74 | n/a | n/a | 97 |
| 564205 | 1073 | 1092 | CTCATGTGCGGCATCAAGTA | 79 | 49247 | 49266 | 98 |
| 564206 | 1138 | 1157 | CATTTGAACAAAATACTCTC | 71 | 49312 | 49331 | 99 |
| 564207 | 1219 | 1238 | CTGATAGCAGAGTCAGTAAA | 72 | 76356 | 76375 | 100 |
| 564208 | 1521 | 1540 | GGGCCACTCGAGCTTTGTAC | 88 | 81681 | 81700 | 101 |
| 564209 | 1628 | 1647 | AGGAATATATTTATTTTCCC | 52 | 83239 | 83258 | 102 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564210 | 1693 | 1712 | CCCATACGCGGTGAATTCTG | 91 | 83304 | 83323 | 103 |
| 564211 | 1713 | 1732 | TGGAGCCCGATCCAGGCTGG | 77 | 83324 | 83343 | 104 |
| 564212 | 1733 | 1752 | AGAAGTGGATCTTGATGGCA | 54 | 83344 | 83363 | 105 |
| 564213 | 1957 | 1976 | GGAGAACCATGAGCAGAGGG | 83 | 85453 | 85472 | 106 |
| 564214 | 2002 | 2021 | GGCCCTTCTGAAGACATGCG | 85 | n/a | n/a | 107 |
| 564215 | 2079 | 2098 | CACTGGATATGGAACCCCTC | 84 | 88189 | 88208 | 108 |
| 564216 | 2099 | 2118 | GTGGGATACAAATTCTAGGC | 94 | 88209 | 88228 | 109 |
| 564217 | 2177 | 2196 | ACTGACCACTGATGACCACG | 67 | 88287 | 88306 | 110 |
| 564218 | 2215 | 2234 | CTGGGTCTATGAGTTTTAGG | 67 | 91099 | 91118 | 111 |
| 564219 | 2291 | 2310 | TGGAATAATACCAGCTTGGG | 84 | 91175 | 91194 | 112 |
| 564220 | 2311 | 2330 | GGCATGGCAACAGCTTCAGT | 81 | 91195 | 91214 | 113 |
| 564221 | 2331 | 2350 | TAGGAGATGCAGCTGGAATA | 71 | 91215 | 91234 | 114 |
| 564222 | 2397 | 2416 | GAAGCCTGGAATCTTTAGCC | 69 | n/a | n/a | 115 |
| 564223 | 2426 | 2445 | CCCTGCAGGAGAGTTCTGCC | 75 | 91696 | 91715 | 116 |
| 564224 | 2582 | 2601 | TTCAGAAGTAGAACTTGGCT | 76 | 112891 | 112910 | 117 |
| 564225 | 2652 | 2671 | CAATTTTGTCTTTGATCAAA | 56 | 112961 | 112980 | 118 |
| 564226 | 2757 | 2776 | TGTTACTAAGTATTGAAGGG | 53 | 113066 | 113085 | 119 |
| 564227 | 2787 | 2806 | AAGTGACCTCAGGTCCCCTC | 83 | 113096 | 113115 | 120 |
| 564228 | 2883 | 2902 | ATGTTGATTTCCTAACTTGC | 53 | 114843 | 114862 | 121 |
| 564229 | 3019 | 3038 | GTATAAACTGGAGTTGGCTG | 75 | 115874 | 115893 | 122 |
| 564230 | 3039 | 3058 | GTGCAAAACAAACAGGCTGA | 79 | 115894 | 115913 | 123 |
| 564231 | 3059 | 3078 | GACTGGATACATCATATTTG | 18 | 115914 | 115933 | 124 |
| 564232 | 3082 | 3101 | GGTTGCACGCCTGGGCTCAC | 74 | n/a | n/a | 125 |
| 564233 | 3102 | 3121 | TCATAGGTATTGGGTATAAA | 50 | 116338 | 116357 | 126 |
| 564234 | 3122 | 3141 | TTGATTCACTGGCATGGGCG | 77 | 116358 | 116377 | 127 |
| 564235 | 3180 | 3199 | GATGATGCTGGTCTTGCCGC | 49 | 130944 | 130963 | 128 |
| 564236 | 3373 | 3392 | ATCATTCTAGCATTACCCTG | 61 | 131454 | 131473 | 129 |
| 564237 | 3408 | 3427 | ATACTAAACCAGGCTGGGCG | 71 | 131489 | 131508 | 130 |
| 564238 | 3464 | 3483 | ACATGCATACATCGCATGCG | 32 | n/a | n/a | 131 |
| 564239 | 3505 | 3524 | TAGAAAGAAGGGCTTGTCTC | 67 | 136978 | 136997 | 132 |
| 564240 | 3545 | 3564 | CGCATACTGCTGAGCAAGGG | 79 | 144320 | 144339 | 133 |
| 564241 | 3597 | 3616 | TAGCTGAAGGCTGAGGGTGT | 43 | 144372 | 144391 | 134 |
| 564242 | 3630 | 3649 | CACCATGTTGGCTTTGCTGC | 81 | 144405 | 144424 | 135 |
| 564243 | 3650 | 3669 | ACTGGGTGCAGGATGACTTC | 36 | 144425 | 144444 | 136 |
| 564244 | 3729 | 3748 | CGTGGTAAATGGCTGACTGC | 50 | 145461 | 145480 | 137 |
| 564245 | 3772 | 3791 | TTGGAGGCAGGTGTCATGGA | 36 | 145504 | 145523 | 138 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564246 | 3938 | 3957 | TGGCGCATGGGCAGTTGGAT | 67 | 147853 | 147872 | 139 |
| 564247 | 3994 | 4013 | CTTTGAGCGAGGGCGGCCTG | 29 | 147909 | 147928 | 140 |
| 564248 | 4021 | 4040 | GTCGAGACTGGAATGGGCTG | 54 | 147936 | 147955 | 141 |
| 564249 | 4225 | 4244 | ATTCCTATTGGATGTTACAA | 65 | 148976 | 148995 | 142 |
| 564250 | 4252 | 4271 | ATCTTCCACTGCAAGTGAAC | 77 | 149003 | 149022 | 143 |
| 564251 | 4306 | 4325 | TATGGAATTATGGAATAGCC | 65 | 149057 | 149076 | 144 |
| 564252 | 4433 | 4452 | GCAAGAATCACTCTTGTTAC | 77 | 149184 | 149203 | 145 |
| 564253 | 4581 | 4600 | TGTAGACAGTGATCACCTCA | 77 | 149332 | 149351 | 146 |
| 564254 | n/a | n/a | GGCCAAGGCCCACTTGTCTC | 54 | 3485 | 3504 | 147 |
| 564255 | n/a | n/a | CACTGCGGCCTCGAACAGCA | 81 | 3709 | 3728 | 148 |
| 564263 | n/a | n/a | AAATTCCTCATTTTCTTTTC | 68 | 26924<br>27239 | 26943<br>27258 | 149 |
| 564264 | n/a | n/a | GTTATAGTAATCTGTAATCA | 71 | 36133<br>36239 | 36152<br>36258 | 150 |
| 564265 | n/a | n/a | AGGATTGTAAAATGATACAG | 47 | 65107<br>65148 | 65126<br>65167 | 151 |
| 564266 | n/a | n/a | GTAGGATTGTAAAATGATAC | 64 | 65109<br>65150 | 65128<br>65169 | 152 |
| 564267 | n/a | n/a | TTATATATGTAAATTATATC | 9 | 95228<br>95288 | 95247<br>95307 | 153 |
| 564268 | n/a | n/a | AACCACTGATTTATACACTT | 88 | 95260<br>95320 | 95279<br>95339 | 154 |
| 564269 | n/a | n/a | TTAAAAACCACTGATTTATA | 17 | 95265<br>95325 | 95284<br>95344 | 155 |
| 564270 | n/a | n/a | ATATAGCACTCTGCTGTATT | 83 | 99282<br>99340 | 99301<br>99359 | 156 |
| 564271 | n/a | n/a | TACCAAGCTTGTGGCTTGGG | 32 | 137342<br>137420 | 137361<br>137439 | 157 |
| 564272 | n/a | n/a | TTATACCAAGCTTGTGGCTT | 52 | 137345<br>137423 | 137364<br>137442 | 158 |

TABLE 3

Inhibition of ataxin 2 mRNA by 5-10-5 MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564256 | 311 | 330 | CCTCGATGTTCCACAGGCGC | 83 | 159 |
| 564257 | 715 | 734 | GAGTTCACCTGCATCCAGGG | 81 | 160 |
| 564258 | 736 | 755 | TCCAGTTCCCTCATTGGCTG | 27 | 161 |

TABLE 3-continued

Inhibition of ataxin 2 mRNA by 5-10-5 MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564259 | 771 | 790 | GGTTCCATCCATTAGATACG | 52 | 162 |
| 564260 | 791 | 810 | TTAAACGAAACATATCTTTG | 10 | 163 |

TABLE 3-continued

| Inhibition of ataxin 2 mRNA by 5-10-5 MOE gapmers targeting SEQ ID NO: 3 | | | | | |
|---|---|---|---|---|---|
| ISIS No | SEQ ID NO: 3 Start Site | SEQ ID NO: 3 Stop Site | Sequence | % inhibition | SEQ ID NO |
| 564261 | 815 | 834 | GCCCCTGCGCCATAATTTTT | 3 | 164 |
| 564262 | 835 | 854 | ATAAACTGCTTTCAACGGTG | 2 | 165 |

Example 2: Dose-Dependent Antisense Inhibition of Human Ataxin 2 in HepG2 Cells by MOE Gapmers Gapmers from Example 1 exhibiting significant in vitro inhibition of ataxin 2 mRNA were selected and tested at various doses in HepG2 cells. Cells were plated at a density of 20,000 cells per well and transfected using electroporation with 0.625 μM, 1.250 μM, 2.500 μM, 5.000 μM and 10.000 μM concentrations of antisense oligonucleotide, as specified in the Table below. After a treatment period of approximately 16 hours, RNA was isolated from the cells and ataxin 2 mRNA levels were measured by quantitative real-time PCR. Human primer probe set RTS3642 was used to measure mRNA levels. Ataxin 2 mRNA levels were adjusted according to total RNA content, as measured by RIBOGREEN®. Results are presented as percent inhibition of ataxin 2, relative to untreated control cells.

The half maximal inhibitory concentration ($IC_{50}$) of each oligonucleotide is also presented. Ataxin 2 mRNA levels were significantly reduced in a dose-dependent manner in antisense oligonucleotide treated cells.

TABLE 4

| Dose response assay | | | | | | |
|---|---|---|---|---|---|---|
| ISIS No | 0.625 μM | 1.250 μM | 2.500 μM | 5.000 μM | 10.000 μM | $IC_{50}$ (μM) |
| 564133 | 89 | 95 | 98 | 98 | 97 | <0.6 |
| 564188 | 52 | 72 | 81 | 88 | 90 | <0.6 |
| 564127 | 42 | 62 | 65 | 85 | 91 | 0.8 |
| 564150 | 39 | 63 | 74 | 86 | 91 | 0.8 |
| 564143 | 37 | 60 | 76 | 84 | 94 | 0.9 |
| 564122 | 25 | 53 | 69 | 85 | 88 | 1.3 |
| 564126 | 23 | 48 | 61 | 78 | 89 | 1.7 |
| 564144 | 12 | 35 | 53 | 71 | 85 | 2.4 |
| 564135 | 22 | 35 | 53 | 73 | 86 | 2.1 |
| 564125 | 33 | 44 | 64 | 78 | 85 | 1.5 |
| 564129 | 31 | 42 | 54 | 71 | 77 | 1.9 |
| 564216 | 50 | 67 | 82 | 86 | 94 | <0.6 |
| 564210 | 33 | 48 | 72 | 80 | 94 | 1.3 |
| 564208 | 30 | 40 | 67 | 75 | 87 | 1.6 |
| 564268 | 35 | 52 | 69 | 81 | 85 | 1.2 |

Example 3: Antisense Inhibition of Human Ataxin 2 in a SCA2 BAC Mouse Model

Gapmers from Example 1 exhibiting significant in vitro inhibition of ataxin 2 mRNA were selected and tested in vivo in a SCA2[Q22]-BAC mouse model. This mouse model was created in the Pulst laboratory (University of Utah, Salt Lake City), using mice of FVB/B6 hybrid background, for the study of spinocerebella ataxia type 2 (SCA2). These mice possess the entire 176 kb human ATXN2 gene region, including the 16 kb upstream sequence and the 2.5 kb downstream sequence.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 μL mark with either normal saline (0.9%) or antisense oligonucleotide (250 μg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 μL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 μL, consisting of 15 ng cDNA, 2 μL of each primer (0.3 μM final), and 10 μL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis.

The results from the RNA analysis for mouse and human ataxin 2 are presented in the Table below. As indicated, some of the ISIS oligonucleotides decreased human ataxin 2 mRNA in the brains of the mice.

TABLE 5

| Percent inhibition ofataxin 2 mRNA compared to the saline (0.9%) control in SCA[Q22]-BAC mice | | |
|---|---|---|
| ISIS No | Human ataxin 2 | Mouse ataxin 2 |
| 564122 | 10 | 15 |
| 564127 | 46 | 65 |

TABLE 5-continued

| Percent inhibition ofataxin 2 mRNA compared to the saline (0.9%) control in SCA[Q22]-BAC mice | | |
|---|---|---|
| ISIS No | Human ataxin 2 | Mouse ataxin 2 |
| 564133 | 60 | 62 |
| 564150 | 21 | 53 |
| 564188 | 9 | 23 |
| 564216 | 21 | 55 |

Example 4: Antisense Inhibition of Human Ataxin 2 in an ATXN2-Q127 Mouse Model

Gapmers from Example 1 exhibiting significant in vitro inhibition of ataxin 2 mRNA were selected and tested in vivo in an ATXN2-Q127 mouse model. This mouse model (Hansen, S. T. et al., Human. Molecular Genetics 2012. 1-13) expresses the full-length-mutant $ATXN2^{Q127}$ complementary DNA under the regulation of the Purkinje cell protein-2 (Pcp2) promoter. This model shows an early-onset progressive motor impairment phenotype accompanied by the formation of diffuse cytoplasmic aggregates in cerebellar Purkinje cells.

Treatment

Groups of 3 mice each were administered normal saline (0.9%) or anti sense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 μL mark with either normal saline (0.9%) or antisense oligonucleotide (250 μg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 μL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 μL, consisting of 15 ng cDNA, 2 μL of each primer (0.3 μM final), and 10 μL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis. All mRNA levels were normalized to the housekeeping gene, actin.

The results from the RNA analysis for mouse and human ataxin 2 are presented in the Table below. As indicated, some of the ISIS oligonucleotides decreased human ataxin 2 mRNA in the brains of the mice.

qPCR analysis of the marker for microgliosis, AIF/Iba1, to measure inflammation, was also performed. The results are presented in the Table below.

TABLE 6

| Percent inhibition of ataxin 2 mRNA compared to the saline (0.9%) control in ATXN2-Q127 mice | | |
|---|---|---|
| ISIS No | Human | Mouse |
| 564133 | 64 | 52 |
| 564127 | 62 | 49 |
| 564216 | 46 | 40 |
| 564210 | 39 | 48 |

TABLE 7

| Percent Iba1 mRNA level increase compared to the saline (0.9%) control in ATXN2-Q127 mice | |
|---|---|
| ISIS No | Iba1 |
| 564133 | 9 |
| 564127 | 49 |
| 564216 | 16 |
| 564210 | 96 |

Example 4: Dose-Dependent Antisense Inhibition of Human Ataxin 2 in an ATXN2-Q127 Mouse Model ISIS 564133 was tested in different doses in the ATXN2-Q127 mouse model.

Treatment

Groups of 3 mice each were administered normal saline (0.9%) or ISIS 564133 via intracerebroventricular injections dosed at 50 μg, 100 μg, 200 μg, 250 μg, or 300 μg. The mice were administered in the same manner as described in the studies above and monitored daily.

RNA Analysis

After 7 days, the mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for mouse and human ataxin 2 are presented in the Table below.

TABLE 8

| Percent inhibition of ataxin 2 mRNA compared to the saline (0.9%) control in ATXN2-Q127 mice | | |
|---|---|---|
| Dose (μg) | Human ataxin 2 | Mouse ataxin 2 |
| 50 | 60 | 47 |
| 100 | 84 | 35 |
| 200 | 85 | 67 |
| 250 | 79 | 62 |
| 300 | 73 | 41 |

Example 5: Time-Dependent Antisense Inhibition of Human Ataxin 2 in an ATXN2-Q127 Mouse Model ISIS 564133 was administered and mRNA level reduction was tested in different time points in the ATXN2-Q127 mouse model.

Treatment

Groups of 3 mice each were administered normal saline (0.9%) or ISIS 564133 via intracerebroventricular injections dosed at 200 μg. The mice were administered in the same manner as described in the studies above and monitored daily.

RNA Analysis

After 9 days, 18 days, 27 days, and 84 days, groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for human ataxin 2 are presented in the Table below. Western analysis of the corresponding protein samples was performed and confirmed the qPCR results.

TABLE 9

| Ataxin 2 mRNA levels in ATXN2-Q127 mice | |
|---|---|
| Time Point | ATXN2 expression relative to actin |
| saline (0.9%) control | 8.4 |
| 9 days | 2.9 |
| 18 days | 0.9 |
| 27 days | 1.4 |
| 84 days | 2.7 |

Immunohistochemical staining of cerebellar Purkinje cells on day 7 was performed using rabbit anti-oligonucleotide antibody generated in-house. The results demonstrated that ISIS oligonucleotide localized in cerebellar Purkinje cells of ATXN-Q127 mice.

Example 6: Effect of Antisense Inhibition of Human Ataxin 2 in an ATXN2-Q127 Mouse Model ISIS oligonucleotide was administered in the ATXN2-Q127 mouse model and wild-type mice. On day 3, motor performance was evaluated using the rotarod test.

Groups of ATXN2-Q127 mice were administered normal saline (0.9%) or ISIS 564133 at 50 μg, 100 μg, or 200 μg via intracerebroventricular injections in the same manner as described in the studies above. Groups of wild-type mice were administered normal saline (0.9%) or ISIS oligonucleotide at 200 μg via intracerebroventricular injections dosed in the same manner as described in the studies above. Groups of ATXN2-Q127 mice were administered normal saline (0.9%) or ISIS 546127 or ISIS 564216 at 200 μg via intracerebroventricular injections dosed in the same manner as described in the studies above. After 6 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20%.

TABLE 10

| Rotarod performance test in ATXN2-Q127 mice | | | |
|---|---|---|---|
| Strain of mice | Number of mice | Treatment | Latency to fall (seconds) |
| WT | 10 | saline (0.9%) control | 199 |
| | 10 | ISIS 564133 (200 μg) | 189 |
| ATXN-Q127 | 8 | saline (0.9%) control | 127 |
| | 15 | ISIS 564133 (50 μg) | 149 |
| | 16 | ISIS 564133 (100 μg) | 141 |
| | 9 | ISIS 564133 (200 μg) | 100 |
| ATXN-Q127 | 15 | saline (0.9%) control | 130 |
| | 13 | ISIS 564127 (200 μg) | 150 |
| | 15 | ISIS 564216 (200 μg) | 156 |

Example 7: Effect of Antisense Inhibition of Human Ataxin 2 in an ATXN2-Q127 Mouse Model ISIS oligonucleotide was administered in the ATXN2-Q127 mouse model and wild-type mice. Cerebellar expression of ataxin 2, as well as several Purkinje cell (PC) genes, was assessed.

Groups of ATXN2-Q127 mice were administered normal saline (0.9%) or ISIS 564133 at 200 μg via intracerebroventricular injections dosed in the same manner as described in the studies above. Groups of wild-type mice were administered normal saline (0.9%) or ISIS 564133 at 200 μg via intracerebroventricular injections dosed in the same manner as described in the studies above. After 5 weeks, the mice were euthanized and cerebellar expression of various gene mRNA levels was assessed.

RNA Analysis

Groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin. RNA levels of human ataxin 2, murine ataxin 2, Pcp2, Calb1, Rgs8, and Fam107b were measured. Transcription changes in several of these PC-specific genes have been demonstrated to progressively decrease in models of SCA2 (Hansen, S. T. et al., Hum. Mol. Genet. 2013. 22: 271-283).

The results from the RNA analysis are presented in the Table below and demonstrate that treatment with ISIS oligonucleotides targeting ataxin 2 increased the expression levels of all the PC-specific genes compared to the transgenic control group.

TABLE 11

PC-specific mRNA levels in ATXN2-Q127 mice

| | WT | ATXN-Q127 | |
|---|---|---|---|
| | saline (0.9%) control | saline (0.9%) control | ISIS 564133 (200 μg) |
| human ataxin 2 | 0.21 | 3.57 | 1.31 |
| murine ataxin 2 | 0.79 | 0.84 | 0.6 |
| Pcp2 | 0.77 | 0.36 | 0.48 |
| Rgs8 | 1.45 | 0.25 | 0.35 |
| Calb1 | 1.14 | 0.5 | 0.71 |
| Fam107b | 1.41 | 0.7 | 0.9 |

Example 8: Effect of Antisense Inhibition of Human Ataxin 2 in an ATXN2-Q127 Mouse Model ISIS oligonucleotide was administered in the ATXN2-Q127 mouse model and wild-type mice. Motor performance was evaluated using the rotarod test.

Groups of ATXN2-Q127 mice (7.5 weeks of age) were administered normal saline (0.9%) or ISIS 546127 or ISIS 564216 at 200 μg via intracerebroventricular injections dosed in the same manner as described in the studies above. After 5 weeks and 9 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20% on week 5 and about 27% on week 9.

TABLE 12

Rotarod performance test in ATXN2-Q127 mice. (mean latency to fall, in seconds)

| Weeks after injection | | ISIS 564127 | ISIS 564216 | Saline control |
|---|---|---|---|---|
| Week 5 | DAY 3 | 137 | 145 | 123 |
| | DAY 4 | 140 | 141 | 119 |
| | DAY 5 | 155 | 154 | 131 |
| Week 9 | DAY 3 | 131 | 149 | 104 |
| | DAY 4 | 125 | 139 | 104 |
| | DAY 5 | 134 | 139 | 112 |

Example 9: Effect of Antisense Inhibition of Human Ataxin 2 in an ATXN2-Q127 Mouse Model ISIS oligonucleotide was administered in the ATXN2-Q127 mouse model. Motor performance was evaluated using the rotarod test.

Seven week old ATXN2-Q127 mice were subjected to the rotarod test, then divided into two groups of 30 mice each, such that average rotarod performance, average weights, and sex composition were equal across both groups. At 8 weeks of age, one group of mice received normal saline via intracerebroventricular (ICV) injection and one group received ISIS 564216 at 210 μg via ICV injection, dosed in the same manner as described in the studies above. Five weeks later (13 weeks of age), the mice were again subjected to the rotarod test. Six weeks post injection (14 weeks of age), the mice received a second ICV injection, identical to the injection received at 8 weeks of age. Five weeks later (19 weeks of age, 11 weeks after the first ICV injection), the mice were subjected to a third rotarod test.

Rotarod Test

The accelerating rotarod test was performed on the Rotamex rotarod. Rotarod testing was conducted over five days. On the first day, mice were acclimated to the technician by being handled by the technician three times, 5 minutes each time. On the second day, mice were introduced to the rotarod three times, 10 minutes each time at a speed ranging from 0 to 10 RPM. On each of days 3-5, mice were placed on the rotarod at a speed of 0 RPM, then the rotarod was accelerated to 40 RPM over 6 minutes, and this was done for each mouse three times. The three total trials per day were used to calculate a mean value of "latency to fall" per day, in seconds. Latency to fall is defined as the amount of time before the animal falls from the rotarod. It was recorded automatically, when the mouse no longer interrupted infrared beams directed above the rotarod. The time to first passive rotation (when mice stop walking and hold on and revolve with the rod) is also automatically recorded, and generally reflects the latency to fall time.

The results from the rotarod test are presented as the average for each treatment group in the Table below. As shown in the Table below, treatment with ASO improved rotarod performance.

TABLE 13

Rotarod performance test in ATXN2-Q127 mice

| Treatment | Weeks after 1$^{st}$ injection | Weeks after 2$^{nd}$ injection | Testing day | Latency to fall (s) |
|---|---|---|---|---|
| Saline | 5 | n/a | 3 | 218.5 |
| | | | 4 | 240.9 |
| | | | 5 | 236.5 |
| Isis No. 564216 | 5 | n/a | 3 | 240.6 |
| | | | 4 | 257.9 |
| | | | 5 | 259.6 |
| Saline | 11 | 5 | 3 | 216.2 |
| | | | 4 | 198.7 |
| | | | 5 | 212.1 |
| Isis No. 564216 | 11 | 5 | 3 | 194.4 |
| | | | 4 | 226.0 |
| | | | 5 | 242.8 |

What is claimed is:

1. An oligomeric compound comprising a modified oligonucleotide consisting of 12 to 30 linked nucleosides, wherein the nucleobase sequence of the modified oligonucleotide comprises a portion of at least 12 contiguous nucleobases, wherein the portion is complementary to:

(i) an equal length portion of nucleobases 1693-1767 of SEQ ID NO: 1;

(ii) an equal length portion of nucleobases 1789-1826 of SEQ ID NO: 1;

(iii) an equal length portion of nucleobases 1844-1887 of SEQ ID NO: 1;

(iv) an equal length portion of nucleobases 2291-2350 of SEQ ID NO: 1;

(v) an equal length portion of nucleobases 3082-3141 of SEQ ID NO: 1;

(vi) an equal length portion of nucleobases 3903-3946 of SEQ ID NO: 1;

(vii) an equal length portion of nucleobases 4005-4054 of SEQ ID NO: 1; or (viii) an equal length portion of nucleobases 4429-4454 of SEQ ID NO: 1;

wherein the modified oligonucleotide comprises at least one modification selected from a modified sugar moiety and a modified internucleoside linkage.

2. An oligomeric compound comprising a modified oligonucleotide consisting of 12 to 30 linked nucleosides and having a nucleobase sequence comprising at least 12 contiguous nucleobases of any of the nucleobase sequences of SEQ ID NOs: 29-35, 49, 50, 57-59, 63-66, 75, or 76, wherein the modified oligonucleotide comprises at least one modification selected from a modified sugar moiety and a modified internucleoside linkage.

3. The oligomeric compound of claim 1, wherein the modified oligonucleotide is at least 95% or is 100% complementary to an equal length portion of an Ataxin 2 RNA transcript.

4. The oligomeric compound of claim 3, wherein the Ataxin-2 RNA transcript has the nucleobase sequence of SEQ ID NO: 1, SEQ ID NO: 2, or SEQ ID NO: 3.

5. The oligomeric compound of claim 1, wherein the modified oligonucleotide consists of 12 to 25, 12 to 22, 13 to 30, 14 to 20, 14 to 30, 15 to 25, 15 to 30, 16 to 30, 17 to 30, 18 to 22, 18 to 30, 19 to 21, 19 to 30, or 20 to 30 linked nucleosides.

6. The oligomeric compound of claim 1, wherein the modified oligonucleotide consists of 20 linked nucleosides.

7. The oligomeric compound of claim 1, consisting of a single-stranded modified oligonucleotide.

8. The oligomeric compound of claim 1, wherein at least one internucleoside linkage of the modified oligonucleotide is a modified internucleoside linkage.

9. The oligomeric compound of claim 8, wherein at least one modified internucleoside linkage is a phosphorothioate internucleoside linkage.

10. The oligomeric compound of claim 9, wherein at least one internucleoside linkage of the modified oligonucleotide is a phosphodiester internucleoside linkage.

11. The oligomeric compound of claim 9, wherein each modified internucleoside linkage is a phosphorothioate internucleoside linkage.

12. The oligomeric compound of claim 1, wherein at least one nucleoside of the modified oligonucleotide comprises a modified nucleobase.

13. The oligomeric compound of claim 12, wherein the modified nucleobase is a 5-methylcytosine.

14. The oligomeric compound of claim 1, wherein at least one nucleoside of the modified oligonucleotide comprises a modified sugar moiety.

15. The oligomeric compound of claim 14, wherein the modified sugar moiety is a 2'-substituted sugar moiety.

16. The oligomeric compound of claim 14, wherein the modified sugar moiety is a bicyclic sugar moiety.

17. The oligomeric compound of claim 16, wherein the bicyclic sugar moiety comprises a 4'-CH(R)—O-2' bridge wherein R is H, $C_1$-$C_{12}$ alkyl, or a protecting group.

18. The oligomeric compound of claim 17, wherein R is methyl.

19. The oligomeric compound of claim 17, wherein R is H.

20. The oligomeric compound of claim 15, wherein the modified sugar moiety is a 2'-O-methoxyethyl group.

21. The oligomeric compound of claim 1, wherein the modified oligonucleotide comprises:

a gap segment consisting of 10 linked deoxyribonucleosides;

a 5' wing segment consisting of 5 linked nucleosides; and a 3' wing segment consisting of 5 linked nucleosides;

wherein the gap segment is positioned between the 5' wing segment and the 3' wing segment and wherein each nucleoside of each wing segment comprises a modified sugar moiety.

22. A pharmaceutical composition comprising the oligomeric compound of claim 1 or a salt thereof, and a pharmaceutically acceptable diluent.

23. The pharmaceutical composition of claim 22, wherein the pharmaceutically acceptable diluent is phosphate-buffered saline (PBS).

* * * * *

SEQUENCE LISTING

```
<160> NUMBER OF SEQ ID NOS: 165

<210> SEQ ID NO 1
<211> LENGTH: 4712
<212> TYPE: DNA
<213> ORGANISM: Homo sapiens

<400> SEQUENCE: 1

acccccgaga aagcaaccca gcgcgccgcc cgctcctcac gtgtccctcc cggccccggg     60

gccacctcac gttctgcttc cgtctgaccc ctccgacttc cggtaaagag tccctatccg    120

cacctccgct cccacccggc gcctcggcgc gcccgccctc cgatgcgctc agcggccgca    180

gctcctcgga gtcccgcggt ggccaccgag tctcgccgct tcgccgcagc caggtggccc    240

gggtggcgct cgctccagcg gccggcgcgg cggagcgggc ggggcggcgg tggcgcggcc    300

ccgggaccgt atccctccgc cgcccctccc ccgcccggcc ccggcccccc tccctcccgg    360

cagagctcgc ctccctccgc ctcagactgt tttggtagca acggcaacgg cggcggcgcg    420

tttcggcccg gctcccggcg gctccttggt ctcggcgggc ctccccgccc cttcgtcgtc    480

ctccttctcc ccctcgccag cccgggcgcc cctccggccg cgccaacccg cgcctccccg    540

ctcggcgccc gcgcgtcccc gccgcgttcc ggcgtctcct tggcgcgccc ggctcccggc    600

tgtccccgcc cggcgtgcga gccggtgtat gggcccctca ccatgtcgct gaagccccag    660

cagcagcagc agcagcagca gcagcagcag cagcagcaac agcagcagca gcagcagcag    720

cagcagccgc cgcccgcggc tgccaatgtc cgcaagcccg gcggcagcgg ccttctagcg    780

tcgcccgccg ccgcgccttc gccgtcctcg tcctcggtct cctcgtcctc ggccacggct    840

ccctcctcgg tggtcgcggc gacctccggc ggcgggaggc ccggcctggg cagaggtcga    900

aacagtaaca aaggactgcc tcagtctacg atttcttttg atggaatcta tgcaaatatg    960

aggatggttc atatacttac atcagttgtt ggctccaaat gtgaagtaca agtgaaaaat   1020

ggaggtatat atgaaggagt ttttaaaact tacagtccga agtgtgattt ggtacttgat   1080

gccgcacatg agaaaagtac agaatccagt tcggggccga aacgtgaaga aataatggag   1140

agtattttgt tcaaatgttc agactttgtt gtggtacagt ttaaagatat ggactccagt   1200

tatgcaaaaa gagatgcttt tactgactct gctatcagtg ctaaagtgaa tggcgaacac   1260

aaagagaagg acctggagcc ctgggatgca ggtgaactca cagccaatga ggaacttgag   1320

gctttggaaa atgacgtatc taatggatgg gatcccaatg atatgtttcg atataatgaa   1380
```

```
gaaaattatg gtgtagtgtc tacgtatgat agcagtttat cttcgtatac agtgccctta   1440

gaaagagata actcagaaga atttttaaaa cgggaagcaa gggcaaacca gttagcagaa   1500

gaaattgagt caagtgccca gtacaaagct cgagtggccc tggaaaatga tgataggagt   1560

gaggaagaaa aatacacagc agttcagaga aattccagtg aacgtgaggg gcacagcata   1620

aacactaggg aaaataaata tattcctcct ggacaaagaa atagagaagt catatcctgg   1680

ggaagtggga gacagaattc accgcgtatg ggccagcctg gatcgggctc catgccatca   1740

agatccactt ctcacacttc agatttcaac ccgaattctg gttcagacca aagagtagtt   1800

aatggaggtg ttccctggcc atcgccttgc ccatctcctt cctctcgccc accttctcgc   1860

taccagtcag gtcccaactc tcttccacct cgggcagcca cccctacacg gccgccctcc   1920

aggccccccct cgcggccatc cagacccccg tctcacccct ctgctcatgg ttctccagct   1980

cctgtctcta ctatgcctaa acgcatgtct tcagaagggc ctccaaggat gtccccaaag   2040

gcccagcgac atcctcgaaa tcacagagtt tctgctggga ggggttccat atccagtggc   2100

ctagaatttg tatcccacaa cccacccagt gaagcagcta ctcctccagt agcaaggacc   2160

agtccctcgg ggggaacgtg gtcatcagtg gtcagtgggg ttccaagatt atcccctaaa   2220

actcatagac ccaggtctcc cagacagaac agtattggaa ataccccccag tgggccagtt   2280

cttgcttctc cccaagctgg tattattcca actgaagctg ttgccatgcc tattccagct   2340

gcatctccta cgcctgctag tcctgcatcg aacagagctg ttacccccttc tagtgaggct   2400

aaagattcca ggcttcaaga tcagaggcag aactctcctg cagggaataa agaaaatatt   2460

aaacccaatg aaacatcacc tagcttctca aaagctgaaa acaaaggtat atcaccagtt   2520

gtttctgaac atagaaaaca gattgatgat ttaaagaaat ttaagaatga ttttaggtta   2580

cagccaagtt ctacttctga atctatggat caactactaa acaaaaatag agagggagaa   2640

aaatcaagag atttgatcaa agacaaaatt gaaccaagtg ctaaggattc tttcattgaa   2700

aatagcagca gcaactgtac cagtggcagc agcaagccga atagccccag catttcccct   2760

tcaatactta gtaacacgga gcacaagagg ggacctgagg tcacttccca aggggttcag   2820

acttccagcc cagcatgtaa acaagagaaa gacgataagg aagagaagaa agacgcagct   2880

gagcaagtta ggaaatcaac attgaatccc aatgcaaagg agttcaaccc acgttccttc   2940

tctcagccaa agccttctac taccccaact tcacctcggc ctcaagcaca acctagccca   3000

tctatggtgg gtcatcaaca gccaactcca gtttatactc agcctgtttg ttttgcacca   3060

aatatgatgt atccagtccc agtgagccca ggcgtgcaac ctttataccc aatacctatg   3120

acgcccatgc cagtgaatca agccaagaca tatagagcag taccaaatat gccccaacag   3180

cggcaagacc agcatcatca gagtgccatg atgcacccag cgtcagcagc gggcccaccg   3240

attgcagcca ccccaccagc ttactccacg caatatgttg cctacagtcc tcagcagttc   3300

ccaaatcagc cccttgttca gcatgtgcca cattatcagt ctcagcatcc tcatgtctat   3360

agtcctgtaa tacagggtaa tgctagaatg atggcaccac caacacacgc ccagcctggt   3420

ttagtatctt cttcagcaac tcagtacggg gctcatgagc agacgcatgc gatgtatgca   3480

tgtcccaaat taccatacaa caaggagaca agcccttctt tctactttgc catttccacg   3540

ggctcccttg ctcagcagta tgcgcaccct aacgctaccc tgcacccaca tactccacac   3600

cctcagcctt cagctacccc cactggacag cagcaaagcc aacatggtgg aagtcatcct   3660

gcacccagtc ctgttcagca ccatcagcac caggccgccc aggctctcca tctggccagt   3720

ccacagcagc agtcagccat ttaccacgcg gggcttgcgc caactccacc ctccatgaca   3780
```

```
cctgcctcca acacgcagtc gccacagaat agtttcccag cagcacaaca gactgtcttt   3840

acgatccatc cttctcacgt tcagccggcg tataccaacc caccccacat ggcccacgta   3900

cctcaggctc atgtacagtc aggaatggtt ccttctcatc caactgccca tgcgccaatg   3960

atgctaatga cgacacagcc acccggcggt ccccaggccg ccctcgctca aagtgcacta   4020

cagcccattc cagtctcgac aacagcgcat ttcccctata tgacgcaccc ttcagtacaa   4080

gcccaccacc aacagcagtt gtaaggctgc cctggaggaa ccgaaaggcc aaattccctc   4140

ctcccttcta ctgcttctac caactggaag cacagaaaac tagaatttca tttattttgt   4200

ttttaaaata tatatgttga tttcttgtaa catccaatag gaatgctaac agttcacttg   4260

cagtggaaga tacttggacc gagtagaggc atttaggaac ttgggggcta ttccataatt   4320

ccatatgctg tttcagagtc ccgcaggtac cccagctctg cttgccgaaa ctggaagtta   4380

tttatttttt aataaccctt gaaagtcatg aacacatcag ctagcaaaag aagtaacaag   4440

agtgattctt gctgctatta ctgctaaaaa aaaaaaaaaa aaaaaatcaa gacttggaac   4500

gcccttttac taaacttgac aaagtttcag taaattctta ccgtcaaact gacggattat   4560

tatttataaa tcaagtttga tgaggtgatc actgtctaca gtggttcaac ttttaagtta   4620

agggaaaaac ttttactttg tagataatat aaaataaaaa cttaaaaaaa atttaaaaaa   4680

taaaaaaagt tttaaaaact gaaaaaaaaa aa                                 4712
```

<210> SEQ ID NO 2
<211> LENGTH: 151001
<212> TYPE: DNA
<213> ORGANISM: Homo sapiens

<400> SEQUENCE: 2

```
tcccaaagtg ctgggattac aggcgtgagc caccacactg gccaaaactt gttcttaaga     60

ttgtattctg ggaccttgat tccaatcaga gaaaagtgat tgtatttttt tatttttatt    120

ttttttagat aaagtttcgc tcttgttgcc caggctggag tgcagtggtg ccctctttgg    180

tcactgtaac ctccgcctcc tgggttcaag cgattctcct gcctcagcat cctgcgtagc    240

tgagatcaca gatgcccacc accacgccca gctaattttt tcgtattttt agtagcgatg    300

gggtttcacc atgttggcca cgctggtctt gaactcctga cctcaggtga tccatccgcc    360

tcggcctccc agagtgctgg gattacaggt gtgagccacc gcgccaggcc aagtgtttgt    420

atttctatta aagaaagaat ataacgggac accattgacg acctgctcca ttgcaggcct    480

ccttgctgtt cctcagactc ccccctcaga gcctttgccc tcgctgtgcc ctccacctgg    540

agcgtttctc cccaggatcc tcatgcccat gctcatttgg gtccctgccc catgtcaccc    600

tctccaggag cttcccctca cagcagccct ggcctgtacc acagccgggt acaggtattt    660

ttttgtttca actggttttt tagttccagt ttcctttagg ttactttatt tatttattta    720

tttatttatt ttttgagacg gagtctcgct ctgtcgccca ggctggagtg catgatctcg    780

gctgactgca acctccacct cccggattca agcaattctc ctgtatcagc ctcccgagta    840

gctgggatta caggcgccca ccaccacacc cggctaattt ttatattttt ggtagagacg    900

gggtttcacc atgttggcta ggctaggtta atttttaaag ggttttgcaa tggtcccttg    960

atctactttt taccttagat gggaaataaa actgatttcc tacattggca gaatacaatg   1020

atcatttttg cctggactat ctaggaggtt aatttcagtt ggactactga aaactgctgg   1080

ttcaatcatt ctccacgttt atctaagtct ttacctttat ctggacagtt ctaggacatt   1140
```

```
gaggggaatt ttggtgtttc ttcccctatt atttcctgaa gtcatttcac tttaaaaaac   1200
aatagattca ctgctcaaaa aaaaaaaaaa aagttaccta ctttctactt gcttccagtt   1260
taactgcaac acattttaaa aagagtctac tgtgctggct gggtaagtta aattaaaact   1320
tctaaagggt ccaaggtcta aagttcgcac attgttttga ggtcggctct gtctctaccg   1380
agggagatcc cattatccgt agttctacca gtcccaatcc catatatttc ctttagaatc   1440
tcatgaatga ggaaaaagaa gttcaagtga gggaacatag gttcaaatga aggtcagata   1500
cctaaaagag ttttctggtg actgtgcgcg gctggggtgg aaaaagtggg gaaaaggtac   1560
ccagatgtgg gtggccccgg agggttgctc cactccagcc ccggcagggc aggacagcgc   1620
ggcctgcctg gtagatgccc cgagccactg gagcgcctac tgtgtggcgg gcgggggacg   1680
gcaggaaaac ggcaggatgc tgtgtcccct gaatctggca gggttctagg tgctttacac   1740
gtagcaagac acattctccg ccccaaggca ctcgcagtca gtccattttc tgggttgcat   1800
caggtggggg caaactaggt ccccgcagaa gtgaagatgc tgaaggaata cagtaggaga   1860
agaaatgctt ctctcctgtc ctccacacca ggcaggcccc agaggctgag accgacacgc   1920
cctccccgaa gggcagaccc gccttgagga aggcggatcc gggtagggac cgccgcctgg   1980
ccctcacccg acccccgaga aagcaaccca gcgcgccgcc cgctcctcac gtgtccctcc   2040
cggccccggg gccacctcac gttctgcttc cgtctgaccc ctccgacttc cggtaaagag   2100
tccctatccg cacctccgct cccacccggc gcctcggcgc gcccgccctc cgatgcgctc   2160
agcggccgca gctcctcgga gtcccgcggt ggccaccgag tctcgccgct tcgccgcagc   2220
caggtggccc gggtggcgct cgctccagcg gccggcgcgg cggagcgggc ggggcggcgg   2280
tggcgcggcc ccgggaccgt atccctccgc cgcccctccc ccgcccggcc ccggcccccc   2340
tccctcccgg cagagctcgc ctccctccgc ctcagactgt tttggtagca acggcaacgg   2400
cggcggcgcg tttcggcccg gctcccggcg gctccttggt ctcggcgggc ctccccgccc   2460
cttcgtcgtc ctccttctcc ccctcgccag cccgggcgcc cctccggccg cgccaacccg   2520
cgcctccccg ctcggcgccc gcgcgtcccc gccgcgttcc ggcgtctcct tggcgcgccc   2580
ggctcccggc tgtccccgcc cggcgtgcga gccggtgtat gggcccctca ccatgtcgct   2640
gaagccccag cagcagcagc agcagcagca gcagcagcag cagcagcaac agcagcagca   2700
gcagcagcag cagcagccgc cgcccgcggc tgccaatgtc cgcaagcccg gcggcagcgg   2760
ccttctagcg tcgcccgccg ccgcgccttc gccgtcctcg tcctcggtct cctcgtcctc   2820
ggccacggct ccctcctcgg tggtcgcggc gacctccggc ggcgggaggc ccggcctggg   2880
caggtgggtg tcggcacccc agccccctcc gctccgggcc cggcgtcccc tcccccgcgg   2940
cccgcgccgc cgtccccgcc ccgtgacccg ccgggctacc cggggtgggc tgggggccgg   3000
cagcgcgggg gagactcgct cgggcctgag ccccgaggct cggccggtgg gcgcagccgg   3060
ggtcctctgg gattgtcagg cctgtccagc ctcccgcagc atccccgccc cctcccccgg   3120
cggtcaagat ggagggagcg ggcggcctcc cctccccacg cgtgttggga ggggttctcg   3180
ggtagcggcg atggtcagcc ccggctcccc cttccgcacg atcctccgcc cgcagcgtgg   3240
ggatgctcgg gcagctcctc cactcccggt ttaggtgtga acgttggagg ggtctggagg   3300
ctgtggtggc gttttccgga acatgtcccc ctccatgggg gacatctctg gaggggagaa   3360
gttagggccg cgtcccccgt gccggttaaa ggggtaggca ccgggctcct ccggaatcat   3420
cagggtctgt cggggctctc tccccgcccc ctccgagtcc tgggaaagat cggaggacgg   3480
ggtggagaca agtgggcctt ggcccccgca cccctctgcg ttcgtgtccg aggcggcggc   3540
```

```
gggggctccc gaactcccct gaaatcgtgg ggctccatgt ggcctccggc agcgttccac   3600
cctcccccac ctggggaagg gaaggggtgg ggagtgcccg gccccgtccc ggccttcctc   3660
cttcccccgc cagacctctc cggcgcgcgg gtggtggccg atccgcattg ctgttcgagg   3720
ccgcagtgga gaaggcgcct gtggaacatc ggtgggtgag ggctggaccc aggctggacc   3780
ctggagatcc ggggtggcgg tgctggtggc agggggcggg caccctgcgc acttatccca   3840
acccccgccc caatttcgga aatgctagga gagagagatt gcagcagggg acgtggtcgg   3900
gttcctgaag gcagaaaggc gggtgtttac tagcgtcttt ttccctccta agccggggtt   3960
gtagtagggg ctgggggctc agtgttgtcc cggctaactg ggtttgactc gagggtgtgt   4020
ttgtgcagga gggcctgttg gggggtggcgg gcggttgtca gttcgtattt cacgaactaa   4080
gaaaatgctt agtgttcaaa gggagaagga aacgtcaata gactccattc cattgtggcc   4140
ggtgtcctta acttcgggag tgccgccaga gcttaccaag ggcacgcaag tccatttccc   4200
ttgtgcctca agtccatccg tgttgtaggc actactgtgc cttctttagg cctaggccgc   4260
cggcttgacg gcgggtgacc ggcgtcctcc ttaaataggc atcttgggct ttggaaggtg   4320
gaataagagg atttttcatt cacccgagtt ttctttttga aaacacattt tcagcaaccc   4380
atttccaaag aatttttatt tacagcagaa attccccatc aagaggaatc agctggtttt   4440
taaggaattc tgctgccttc aaagggggcg gaaacagtcg gttatttgac tttacacgcc   4500
ccgccccccc ttccccttct ctgagtctga agcatcccaa acactactta gccaaactag   4560
ttcagatgaa gtgatcgttt ccccaagtag ggtaacttca gtttcccttt ttcgttggca   4620
tctagcgaaa aatgaaaaaa tttaaaatac aacttttata gaaaaggatg tattctgttt   4680
ttactttctt aggtattagg aagagatttg gcagataatt caacatgttc aaatatataa   4740
acattaaaac taaggttatt aagttgcatt gactactagg cttaaaaatt agattataag   4800
agaatttgct cctgagtagt ttgagtgatc aaagatattt ggaatgtttt agtaccacaa   4860
ggtctttttt ctgttccttg aggctttaca acaatttaag gttaatttag atttttcctt   4920
gctttaagtt cttttacttg agacctaaat ggcagccctt attctttctg atgaataggt   4980
gaaattttgt ttactgtgtt ggatttgtgt aatgtgaagt tttattcttg aacagatcgt   5040
taatgtactt gtagaattac tttgaatttg aatcactttc ctgcattcct tgtaaataag   5100
tttcagcttc tagaatctcc tcacttaggt ttgtgcgtat caacagtgaa aataagtctc   5160
tgagagcaag ggtgaaaaaa aatgcagcat tcggtttgac aagtttcgag atagcaaaat   5220
atgcttgaaa gtctggaaat tcacatctgc tttaagaaac atttcataat ttgactttgt   5280
gtgtgtgtgt gtgaatagtt tttcatgact ttcagaagtg atttattttg ttctttgtta   5340
tatatatttt tgaaggtggc tgttttagga aagataatgt aatcacaata ttagaacata   5400
attttactgt aatctaattt tgtgtgtgtg tgtgtgtgtg tgtgtgtgtg tgtgtgtgtg   5460
ttttggatgg aatctcactc tgtcgcccag gctggagtgc agtggcctga tctcagctta   5520
ctgcagtctc tgtctcctgg gttcatttaa gtgattctcc agcctcagcc tccccagtag   5580
ctgggattac aggttcgtgc taccacacct ggctaatttt tttgtatttt tagtgaggac   5640
gggattttgc catgttggcc aggctggtct cgaactcctg acctcaagtg atccgcctgc   5700
cttggcctcc caaagtgctg ggattacagg cgtgagctac tgcccctggc caatttttgt   5760
atttttagta gagatggggt ttcaccatgt tggccaggct ggtctcgaac tcctcctgac   5820
ctcaagtgat tcgccagcct cggcctccca aagtgccagg attacaggca ggaatgagcc   5880
```

-continued

```
actgcccccca accatcagtc taattcttat ttttgctttt taccttttca tttttatgta   5940
gtagaggtga ttgtgtatgt tattttgtag ttagcttttt tcccctgaac gttgtattgt   6000
aaatgtaaat tttttttttt ttttttgaga cagagtctcg gtgtttgccc agtctgaagt   6060
gcagtggtac gatctcagct cactgcagcc tctgactcct gggttcaagc gattctccca   6120
cctcagcctc ttgagtagct ggggctacag gaatgttcca ccacgcttgg ctaatttttg   6180
tatttttggt agagacaagg tttcaccatg ttggccagtt tggtctcgta ctaccgacct   6240
caggtgatgc gcccgcctcg gcctcccaaa gtgctgggat tgcaggcgtg agccactgcg   6300
cccggctgta aggtttttac ttaaccattc tattgttggg aattgggttt ccactttttt   6360
gttatagata gtggtgcagt gaacattttt aaatagcttt ttgcttcagt gtaattattt   6420
ccttagagaa agttaccaag agtggtttta ctagttcaga gggcttcagg atttttatgg   6480
ctcttgctag cggtgctcta ttattcttta gaagacttgt attacttcca gtgtcaagaa   6540
ggttgctctt ccatggaatg gtttctttgt agtttgtcaa atattgtggg gaatttttaa   6600
aggaaaaatt gcatttttac tgtcaagtgc atatattatt aagtgctttt gttagttact   6660
ggattattga tatttgagtt taatttggtt cctctgagga tttaataagg taatatatgt   6720
gaagatgttt tgaaacctgt aaccattatt attaatgagg gtacttggtt tatctgtcgt   6780
gctgatagta ctgagtaaag tgcaggaatg aaattcctga ggaactgttc taaagctttg   6840
ttgttgttgt taacctttct ttttcatctg aaagtgtttt ttattagctg ctagcctatg   6900
accaagttat ttttggtaac ttttttgtaa tttcatggca ctattgggaa ttttcgctgg   6960
ttgactcttc ttcttctaca ttcccttccc cattaaaaat aaaaatatgg atttacaatt   7020
gttactctat tcctaaacct aaataaatatg acattagaat tgcttgggat acaggattca   7080
gtctgaataa aatattttc ttttagtgat tttcagctta gtatttttac tgcttctttc   7140
tcttgaggca ttgcaactta aaaattgtgc tgtttagcca ggcgcctgta atcccagcta   7200
cttgggaggc tgaggcagga gcatcacttg agcccaggag gcggaggttg cagtcagctg   7260
agattgtgcc actgcactcc agcctgggag acagagtgag actctatctc aaaaaaaaaa   7320
aaaatgtgct gtgatttaat gtagttgttc atcatgcttc catttaaatt tcagtgagac   7380
tgttcatctt ttgcagttaa atatcttgta gaagggccta aaatatctac gttgaataca   7440
gctttattga agcatctatg tacatggggt ttttgggatg aatcagtgaa taaagcaaac   7500
atattgtcct tttggagttt acattctaat gtgactaggc agacaatgag acattaaatt   7560
accagcctat gtataatagt gtataagagc tatggaatta gaagaaagca gattaaaggt   7620
atagggagtg tggggagggg aatgagttac aattttaaat ggattggggg aacttaattg   7680
aggagctaac atttgagcaa agatttgaag gttgggtatt tagccgtttg ctttttatct   7740
aggttaatta gtcatgtggc ttcattagta atttataagg tttaaatggc atcatccttt   7800
gttattcttt tatgtgcaca ttgatactaa ccatctctga agttagacca aaaaagttaa   7860
ttgacattga gggtcattag aggtaaattg tagatggcta ttactaacca aagagacatg   7920
ttttgttttt cttttgggct tacgtatttt acctaattag tttagttttt gtttcaagta   7980
tgtggagaaa ataaactttt taagtttggg ccaaaacttg ctttggtttt ctttttcttt   8040
ttcttttttt ttttttaaga gaaaaatgta agcctgtagt tgcttaaaga ttccacattc   8100
tgaaacagtg aaaacatggg atcagtcatg gtgttccttt ttttggttaa atgtaaactt   8160
gtattttcag tgttactcta attagcaatg gtttatactt ctacataagg gatgttaact   8220
catattgtag ctatttaata gccatatatt ttgacttaaa ggaggatctc aaggccaggc   8280
```

```
gcggtggctc atacctgtaa tcccagcact ttaggaggct gaggcgggtg gatcacctgg   8340
ggtcaggagt ttgagactag tctggccaac atggtgaaac cccatctct actaaaaata   8400
caaaaattag ccgggcatgg tggtgggcgc ctgtaatccc agcttcttgg gaggctgagg   8460
gaagagaatt gcttgatccc ggaggttgca atgagtgcgg aggttgcagt gagctgagat   8520
catgccatta cactccagcc tgggcaacag agcgagactc tgtctcaaaa caaacaaaca   8580
aacaaaaaaa ggaggatctc attttttgt cctaaatagc tacagccgtg ttagaactgt   8640
caccttagca aagtattgtt tttttacttt gaaacgaatt ttaaggtttt agaagattgt   8700
tctctagaat tacaatttc tgttttgact agtgatagta ttttgatgtt gtgtaaatag   8760
ttgagcatga acaaaaccct attttttttt ttagctattt caagtgattg tgacaacttc   8820
aacggagatg taaacagttt attaacagtc acacctatta tcttttttt tttttttttt   8880
ttttgagacg gagtcttgct ctgtcgccca ggctggagtg cagtggcacg atctctgctt   8940
actgcaacct ttgcctcccg ggttcaagtg attctcctgc ctcagcctcc tgagtagctg   9000
ggtctacatg cgcacaccac cacgcctggc taatttttgt atttttagta gagacagggt   9060
ttcaccatgt tggctagaat ggtctcaaac tcctgacctc aggtgatcca cctgcctcag   9120
cctcccaaag ttctgggatt acaggcatga gccaccgtgc ttggccgctg ccgtatcttt   9180
ttaaatgaaa gtacttgtgt ttttttgtt tttttccaaa ggatatctgg gtcatctatg   9240
atgttactgt taccatctaa gggtttttt gtttgtttt gagacagagt ctctgtcgcc   9300
caggctggag tgcagtggcg tgatcttggc tcactgcaac ctccgcctcc caggttcaag   9360
caattctcct gccttagccc tcccgaatag ctgggattac aggcacccgc caccatgcct   9420
ggctaagttt tgcattttta gtagatatgg agtttcacca tgttggccag gctgctcttg   9480
aactcctgac ctcaggtgat tcgcttgcct cggcctccca aagtgctggg attacaggcg   9540
tgagccaccc ccgcccagcc tcatgagcta aggtgttttt tttttttttg agacagtttt   9600
gctctttccc aggctggagt gcagtggtgc aatctcagct cactgcaacc tctgtttccc   9660
gggttcaagc gattctcctg cctcagcctt ctgagtagct gagattacag gtgcctgcta   9720
ccccactcag ctaatttttg tatttttagc agagacaggg tttcaccatg ttggttaggc   9780
tcatctcgaa ctcctgacct taagcgatcc acctgccttg gcctcccaaa gtgctgggat   9840
tataggcatg agccaccgtg cgcagcctac cctgtctctt aaaaaacagt aacaacaaca   9900
acaacaacaa aaaatcctaa atcttaaaaa tggaaggcaa aaactctaag ctttgagaga   9960
ttaggggact tgcccaaagc aatatttgta ggattttatt acacctctcc ctttatttat  10020
ttttttagag tcaaggtctc cctctgtcac ccaggctgga gtgcagcctc aatctatggg  10080
gccaagcatt tctcctgtct tagcctcctg agtagctgga actacaggtg tacaccagct  10140
ggctaacatt taaatttttt gtagagacag ggtcctgcca tgttgcccag attggtctca  10200
aactcctggg ctcaagtgat cctcctgcct cagcttccca aagtgctgag attacaggtg  10260
tgagccactg caccgagccc cctcccttta tttttatttt taaattttaa gttctggggc  10320
ccctcccttg aaataaatag aaacgtaata tatacacaag atcatgctgt gtattttaag  10380
gcaatggtcc tcaacctttt taacactagg gaccggtttt gtggaagatg gtttttccat  10440
aggggcaggg gatgattttg agatgaaact gttccaccgg ccgggcacgg tggctcacgc  10500
ctgtaatccc agcactttgg gaggccgagg cgggcagatc acgaggtcag gagatcgaga  10560
ccatcctggc taacatggtg aaacccccct ctactaaaaa tacaaaaaaa ttagctgggc  10620
```

gcggtggagg gcgcctgtag tcacagctac tccggaggcc gaggcaagag aatggcatga 10680
aacccgggag gcagagcttg cagtgagctg agatagcacc actgtacttc agcctggggg 10740
acaaagtgag actccgtcta aaaaaaaaaa aattgttcca cctcagatca ttatgcattt 10800
gttagattct cataaagagc atacaaccta catctcttgc tatatgcagt tcccagtagg 10860
gtttgtgctt ctataagaac ctaatgctgc acctgatcta acaggtgggg ctcaggtgct 10920
aatgctcaca cagctcctgt tgtgcagtct ggttcctaac aggcctgttt tttttttttt 10980
aattagatgg agtctcgctc tgtcaccagg ctggagtgca gtggcacgat ctcagctcac 11040
tgcaacctct gcctcccggg ttcaagcgat tctcctgcct tagcctccca tgtagttggt 11100
actacaggcg cacactgtga tgcccagcta atttttgtat tttagtaga gacggggttt 11160 caccatgttg gccaggatgg tgtcgatctc ctgaccttgt gatccgccca acagcctccc 11220
aaagtgctgg aattacaggc gtgagctgct gcgtccggcc ccctaacagg cttgttttat 11280
ggaatacagt cacggacagt acttgccctt caggatatct ttttgtaacc ttgattttgg 11340
cttgctaaaa taggaggtct attttctttt ctttgttttt aatgtatgtg gttctgtact 11400
tacgtggtgt gaaatctaca taaatgttaa atccttggtt atttatttat tttgagacag 11460
agtctcactc tgtcacccag tctggaaagc agtggcataa tctcggctca ctgtaacctc 11520
cacttcccag gttccagtga ttctcctgcc tcagcctcct gagtagctgg gattacaggc 11580
atgcaccact acacctggca aatttttgta tttttttta gtagagatgg ggtttcacca 11640
tgttggccag gctcgtcttg aactcctgac cttaggtgat ctgcctgtct tggcctccca 11700
aagttttggg attacagcat gagccactgc gcctcgcctt attttttga gacaggttct 11760 agctctgtca cccaggcggg agtgcagtgg tgccatcatg gctcattgca acctcgagtt 11820
ctcaggccca agtgatcctc ctatctcagc ctcctgagta gctgggacca caggcatgcg 11880
ccactatgcc cagcaaaatt tttgtttcac tctgttgcct agggtggggt gcagtggcag 11940
gatatcggct cagtgcaacc tctgcctctt gcgttcaaat gattctcatg cctcagcctc 12000
ccgagtagct gggattatag gcatgcgcca ctacacctgg ctaattttg tattattggt 12060 agagatgggg ttttatcatg ttggccaggc tggtctcgaa ctcccgacct caggtgatcc 12120
atataccttg gcctcctgaa gtgctggaat tacaggcata agccactgcg cctagctttt 12180
ttgtttgttt ttattttgta gggacagaga ttttacctgt tgcccaggat ggccttgaat 12240
tcctgacctc aaacaatttg ccctccttgg cctcccaagg tgctgggatt acaggtgtga 12300
gccactatgc ctggctggtt ttttaaatta ttattattgt ttgtgtgtgt gtgttgcagg 12360
atcttaccct gtcacccagg ctggaatgca gtgatgtgat ctcggcttac tgcaacctcc 12420
gcctcctagg ttcaagtgat tgtcctgcct cagcctcctg agtagctggg ataacagctg 12480
tgtgccacca tgcctggcta atttttgtat tttagtaga gatggggttt catcatgttg 12540
gccaggctgg tctcgaactc ctgaccttag atgatccacc cgcctcgtcc tcccaaagtg 12600
ctgggattac aggtgtgagc caccgtgacc agtttggttt agtttttttt tttttttttt 12660
tttttttttt tttttgagaa atctcgctct gtcgcccagg ctagagtgcg gtgacacaat 12720
ctcagctcac tgcaagctcc acctcccagg ttcatgccat tctcctgcct cagcctcccg 12780
agtagctggg actacatgcg cccgccacca tgcccggcta atttttttta tgcattttaa 12840
gtagagatgg ggtttcactg tgttagccag gattgtctca atctcccgac ctcttgatct 12900
gcccgcctcg gcttcccaaa gtgctgggat tataggcatg agccaccgcg tccggcctgg 12960
tttggtattt tttttatgag tctgggttgt ttatgaaaac ttgtcacagc tgttaacctt 13020

```
aactttttttt ttttcttttt tttccgagac ggagtctcgc tctgtcacct aggctggagt  13080
gcagtggtgc gatctcggct cattgcaacc tctgcctccc aggttaaagc gatttttctg  13140
cctcagcctc ctgagtagct gggactgcag gcacgcacca tctcgcctgg ctaatttttg  13200
tattttagta gagatggggt ttcaccatat tggccaggct ggtctggaac ttctggcctc  13260
aagtgatcca cctgccttgg cctcccatgc ctggcaacct taacttttta tttgctggta  13320
attatttgtg tttgcattca tgtgaaaatt tgaaattctc attaacattt aaagattctt  13380
acatagattg cttgtaattt taaccctgaa gttgtgtcaa gtgactttac aatgtcaatt  13440
tgttttattt atttatttat ttatttattt atttattttt gtgataggat ctggctctgt  13500
tgctaaggct ggagtgcagt gttgcaaata cggctcactg caacctctgt ctcccgggtt  13560
caagccatcc tcccacctca gcctcccaag tagttggaac tactggtgcg ccccacagtg  13620
cctgcctagt tttttgtat tttcagtaga tgtggagttt tgccatgttg atcttgaact  13680
catggcctcg agtgatccac cccacttagg cctcctaaca tgctggtgtt acaggtgtga  13740
gccactgtgt ccagcccgaa aatgtcagtt tcgtgccatg attaatagct aactacattt  13800
tgggaatgta ataaaatttc attctataat gaagtctttg taaaactcat tagttgtggt  13860
atgaggcttg tcggcaatat aagtgaacgt ggtttatttt tattaactgt atcagaactt  13920
tagaatgttg gtctcctgaa accattgcct tgagaggctt tattgaacag tgttgccaat  13980
gatcagtttt tttttaaatt tccttttttt tgagactgag tcttaccctg ttggccaggt  14040
tggagtatag tggtatggtc atggctcact gcagcctcaa catcctgggc tcaagcagtc  14100
ctcctacctc agtctcccga gtagctggaa ctacaggtgt atgccaccat gcctggcttt  14160
tgtatatttt gtagagacag ggtttagcca tgttgcccag gctggtctca aactcttaaa  14220
ttcaaatgat ccacccacct agttttccca aagtgcttta attacatgtg tgaggcaccg  14280
tggctggcca ggtcaaatat ttttcattga cgtttttcat attgcttttt aaagtcatgt  14340
taaaatattc ttaataattt ttctaagtgg aattaatctt gattataatt ttagtttttt  14400
ataaagggcg ggttttgaaa caagtactgc atttttcttt tcgggtttat aaacatttgc  14460
tgtggacttt gtgcagttaa ctattttcat tcctgaaaca catttcgaaa tcaggaattg  14520
aagactaaat gtcttttcac tgaagcttga gcagatttta gaaaggggag ttcttttttt  14580
tttttttttt tttggtagaa atgggggtct tgttatgttg cccaggctgg cctccaactt  14640
ctgggcttaa actgtcctcc tgctttagcc tctggtctgg agagttcttt atggcctctt  14700
tgagaacttt tactttacac atgattctat ctagctttct tttctgatgt acatattggc  14760
agcaagtaga aaagcaatgt tttcagaggc agatatatta acagcaatga gaaataacag  14820
tagcgtgata gaaagttgaa agacttagct gggtgcggtg gctcacgctt gtaatcccag  14880
cactttggga ggccaaggag ggtggatcac ttgaggtcag gagttcgaga ccagtctggc  14940
caacatggtg aaaccctgtc tctactgaaa aacagaaaaa gggccgggcg tggtggctca  15000
cccctgtaat cccagcactt tgggaggttg aggagggcgg attacaaggt caagagattg  15060
agaccattct ggccaacagg gtgaaacccc atctctacta aaaatacaaa aaaattaaat  15120
gggcgtggtg atgtgtgcct gtagtcccag ctactcggga ggctgaggca ggagaattgc  15180
ttgaacccgg gaggcagagg ttgcagtgag ccgagatcgg gccactgcac tgacgacaga  15240
gggagactcc gtctaaaaaa aaaaaaaaaa aaaaaaaacc agacttgggg ctgggcgggc  15300
gcctgtaatc ccagctactt gggaggctga ggcaggagaa tcgcttgaac ccgggaggtg  15360
```

```
aaggttgcag tgagctcaga ttgtgccact gtgccccagc ctgggccaca gagcagagtg  15420
agactctgtc tcaaaaaaaa aaaaaaagtt tggaagactg gtggctgggc atggtggctc  15480
acacctgtaa tcccaacact ttgggaggct gaagcaggca gattacctga gcccaggagt  15540
tcaagtccag cctgggcaac acagggaaac cccatctcaa caaaaaatat taatacaaaa  15600
aatttagcca gtcatggtcg tgcacttctg tagtctcagc tacttgggag gctgaggcag  15660
gtggttcact taagtctgga tgtcgaggtg agccatgatt gcaccactgc actccagcct  15720
gggcgttaaa atgagacctt atctcaaaaa aacaaagcaa agagcctggg aactactaaa  15780
atgggaacta ctaaaaaaca gacacaagag ctcaacaagt ataccattct gggaggtttt  15840
ttttttttt ttttttttt tttttgagat ggagttttgc tcttgtcacc caggctggag  15900
tgcaatggcg ccatctctgc tcactgtagt tccgcctccc aggttcaagc agttctcctg  15960
cctgactcct gagtagctgg gagtacagat attggtcaca caccgggtta atttttgtat  16020
ttttagtaga gacggggttt ccccattttg gccaggctgg tctcgaactc ctgacctcag  16080
gtgatccgcc tgcttcagcc tcccaaagtg ccgggaccac aggcgtgagc caccgcacct  16140
ggcttttttt ttttgacata gaatcttgtt ctgttgccca ggctggagtg caatggtaca  16200
atcttggccc actgcaacct ctgcctccca gcttctagcg attttcctgc ctctgactcc  16260
tgagtagctg ggattacggg tgcccgccac cacacccgga taatttttgt atttttagta  16320
gagatggggt tttgccatat tggccaggcc ggtcttgaac tcctgacctc agatgatcca  16380
cctgcctagg cctcccaaag tgccgggatt acaggcgtga gccaccactc ccggcctggg  16440
agttttgact gtaagtttat agctgtatat cttaggccct aagggcatta ctgttttata  16500
gcacagtgta gttagttaat gtgctcataa tggtgactca taacaccagg ttaaatgatt  16560
ttttatatct cccaaagaag tatttttcaa tctgcagatc atgacccctt agtagattgt  16620
gaaacacatt agtggattat gacaagcatt tttagaaaaa tgaaaaagaa taagaagtgt  16680
taggatgcat tgcattattg aaataattgt ttttgagatg gagtttcgct cttagttgcc  16740
gaggctggag tgcaatggcc cgatctgcct cccgggttca agtgattctc ctacctcagc  16800
ctcctgagta gctgggatta cagacatgct ccaccatgcc tggctaattt tgtatttagt  16860
tttagtagag atggggtttc tccatgttgg tcaggctggt cttgaactcc tgacctcagg  16920
tgatccactt gcctcggcct cccaaagtgc tggggataca ggcatgaacc cctgtgcccg  16980
gcctaatttt tgtattttta gtagagatgg ggtttcacca tgttggccag gatagtcttg  17040
atctcttgac ctcgtaatct gcccacctcg actcccaaag tgctgggatt acaggtgtga  17100
gccactgcac ccagctgcca agaattgttt taagctttgg tttgagttaa tgtatatata  17160
ccgcattgta attcaaaatg taatttttgg ccaactctgg gcacattgcc tatggactag  17220
tcctgctctg ccacgagcag caacagttca atgaattttt tttttttttt tttttttttt  17280
tttttttttg agacagggtc tctgtcacca aggctagaat gtagtggtgc agtctcggct  17340
cactgcaacc tctgtttcct gggctcaagc gatcctccca cctcagcctc ctgagtagct  17400
gggagtacag gagcacgcta ccatgcctgg ctaatttttg tatttttga agagatgagg  17460
ttttgccatg ttgttcaggc tagtcttgaa ctctggagct cagatgatcc acccaccttg  17520
gtgtccagaa atgctgggat tacagggatg agccaccgtg cctagccaaa aattttttttt  17580
taagtaattt tttattgata tagtcaaaaa agttactgct ttagagccag agaaacgcag  17640
taaaaggatt gagaaagagt tttgaggtta tatctaagct agggttgtca gatttggcaa  17700
atagaaatac aggacactca gttaaatttg aatttttgat gaacattgac cagtttttta  17760
```

gtataattgt gtattaaatt gcatagaaaa aagttattta tctaaagttg aaatttaact 17820
gagcatcttg tattttatct ggcaactcca gtctaagctg gaatcatggt tcactgtttt 17880
ttttttttt ttttttttt gagtcggagt cttgctgtgt tgcccaggct ggagtgcaat 17940
ggtgcgatct tggctcactg caacctccac ctcctgtgtt caagtgattc tcctgcctca 18000
gcctcctgaa tagttgggat tacaggcacc caccaccatg cccagctaat tttatattt 18060
ttagtagaga cggggtttc gccatgttgt tcaggctggt cttgaactcc tgacctcagg 18120
tggtccgccc acctgggcct cccaacgtgc tgggattaca ggcatgatct accgtgcctg 18180
gccatggttc actcttcagt aactaaaatt taagctctat gaaagcagga actttgtttt 18240
gttcactatt gattgtatcc ctatttcttg aatggttggc acttaactgc ttggtcacat 18300
gtttgaatgg gcaagttact cagccactct caggcttagt ttatttacct attaaaagag 18360
aaagaatatc ttccttggct gggcgcggtg gctcacgcct ataatcccag cactttggga 18420
ggctgaggcg ggtggatcac gaggtcagga gatcgagacc aacctgggca acattgtgaa 18480
acctcatctc tactaaaata gaaaaaatta gctgggcatg gtggtgcgca tctgtagtcc 18540
cagctactcg agaggctgag gcaggggaat cgcttgaacc caggaggtgg aggttgcagt 18600
gagccaagat tgtgccactg cactccagcc tgggcgacag aacgagactc tgtctccaaa 18660
aaaaaaaaaa aaacaaacaa aaaaaaaaac tgagatactg gccgggcgcg gtggctcgtg 18720
cctgtaatcc cagcactttg gaaggccgag gcgggtggat cacgaggtca ggagatcgag 18780
accgtcctgc ctaacatggg gaaaccctgt ctctactaaa aatacaaaaa attagccagg 18840
cgtggtggcg ggcgcctgta atcccagcta cttgggaggc tgaggcagga gaatggcgtg 18900
aacccgggag gcagagcttg cagtgagcgg agatggtgcc actgcactcc agcctgctgg 18960
gcgacagagc gagactccgt ctcaaacaaa caaacaaaca aacaaaaaaa ctgagatact 19020
aaagtcttaa tattttctgt ttttatgtat ttattttttg agatgggatc ttgctgtatt 19080
gcccaggttg gagtacagta ttgtgatcat ggcttattgc agcctttaac tcctgggttc 19140
aagtgatcct cccacctcag cctcctgagt agctgggacc acaggcacat gcaacatcac 19200
accctgcagt tctttttttt tttttgagac accgtctcgc tttgtcaccc aggctgcagt 19260
gcgtggtgca atttctgctc actctaacct ccacctcccg agttcaagca gttctgcctc 19320
agcctcctga gtagcttggg accacatgtg tgtgccatca tgcctggtta atttttttgta 19380
tttttagtag tgacagggtc ttaccatgtt gcccaggttg gtctcaaact cctgagctca 19440
agtgatctgc ccgccttcgc ctcccaaagt gtctgcgccc tacaatttaa aaaaattttt 19500
gtagagacag tctcactgtt acccgggctg gttttgaact tctgccctca agtactcctc 19560
ttgccttggc ctcccaaagt attgaaatta aggccatgag gcagcacacc cagcctaaat 19620
tcttcttatg ttctgttctt ggcacatagt agatgttcaa caatgtagag tcaaacgcat 19680
ttggagttgg aatggctctg gtgttttttt tttttttta aaccagaaac acgtgcagtt 19740
tattgaatgc cattgtagaa aagtgtgtga ggataaacgg ctgatagaga acttggctct 19800
gggggcaggg cgaggaatgg agggtggatg gagtacatgg gaatcagatc acgggcagag 19860
ctcctggcct agataatgcc tcctgatctg ttgatagact tgaaagatca acactgggat 19920
gatgctgagc agaatggtcg taatgatgcg cacaatcagg gcccagatgt tcaggcactt 19980
ggcggtaaag gcataggcct gggccctgat caggtcgcca accatcttct tgtccctaga 20040
cttcacggag taggccaatg ctatgaagcc caggcagcag gagttcatga agtgggtgtt 20100

```
gaacagggac cagacgacat ggtcgggcac ggagttctcg ctgtggatgg ggatcacggt  20160
ggacattggg ggagcagggt tgtggggtgc ccccagcaca gccacctctt gctcctcctt  20220
gagcatctca tagttagggg gatggccgat gttggcagga gtgaagaggt ttggacattg  20280
tggttcatgg tgtccaggga agaccagctg tggtcgggtt gctggggtgg ttctcagtgg  20340
gcccctccct ttccctggta gtttggattt ctctggctct ggtggttttt tagtactcat  20400
tctatttacg ggtgaagaaa ttgagaccaa gagggttatt taccagagta tctcatcatt  20460
ggctgcataa ctggcattag aatctgatgt acttttattt ctaatacatt tctttttttt  20520
tttttttttt tgagatggag tctcgctctg ttgccgagcc tagagtgcag tggggcaatc  20580
ttggctcctt gcaacctcca cctcctgggt tcaagctatt cctgtctcag cctcccaagt  20640
agctgggact acaggcacct gccaccacag ccggctaggt tttgtatttt agtagagatg  20700
gggtagcacc atgttggcca ggctggtctc gaactcatga cctcaggtga tccacctgcc  20760
tcggcctccc agtgctggga ttataggcat gagccaccat gcctggcctt tctttgtcgt  20820
ttcctttctt tctcttcatc cctcctctcc tttttttcccc tccccgctgc ctcctcctgt  20880
cttcccttct ttccttcctt tctctccttt ttattttttc ctttcttttt ctttctctgt  20940
ctctcccaac ccttcctctc tccctccctc cctccccttc tctctccccc cctccctccc  21000
cttctctctc cccctcccct tttgttccta agagacaggg tctccttatg ttgctgaggc  21060
tgaccttgaa ctcctgagcc cagatgattc tgcctcctta gtagctggga ctacacccac  21120
ctcccgttcc gttgtcatct tttttttttt tttctttttt ggagacagaa tcttcctctg  21180
ttgctcaggg tggagtgtag tggcacgatc atagcttact gtaactgtgt aacctcgaat  21240
tcttgggctc aagcaatcat cccatcatcc cacctcagct tgctgagtac ctggggctac  21300
aggtgtgtac caccatgtcc ggctaattac ttttcttatt tttaattttt cggagatagg  21360
atcttgctct gttgcccagg ctggtgtcaa actcctgggc tcaagtgaaa ctcttgcctt  21420
ggcctcccaa agtgttggga gggattacag gcatgagcca ctgcacccag cctcctcttt  21480
cttcccattt aactcctaac cacaccgaac tttctgtctg cagagaggag cattggtcag  21540
cagttcacaa aatggctagg tgtgatggcg tgcacccata gtcccagcta cttggggagc  21600
tgaggtggga ggatcgctgg agcccaggag ttcaaggccc tgggcaacac agcaagacct  21660
tatctctggc tgggcccagt ggctcacgcc tgtaatccca gcactttggg aggctgaggt  21720
gggtggatca cctgaggtca ggagttcgag accagcctgg ccaacatggt gagaccctgt  21780
gtctactaaa agtacaaaaa ttagccaggc acggtggcgc gctcctgtaa tcccagctac  21840
tcgggggggc tgagacagga gaatcacttg aacccaggag gaggaggttg cagtgaacca  21900
agaacacgcc actgcactcc agcctgggtg acatagtgag actcttatct caaaaaaaaa  21960
aaaaaaaggt cgtctgtact attgcatgtt agtagtttct ttctgcttat tgttgagtag  22020
tagtctattg tatgcatgta ccagtttgtt catctagtgg tggacattga gttagcaggt  22080
tttggctatt aaaaataaag ctggaggccg ggtgcgatgt ctcacgcctg taatcccagc  22140
attttggaag gccgaggcag gcggatcacc taaggttggg agtttgagac cagcctgacc  22200
aacatggaga aaccccatct ctactaaaaa tacaaaatta gccaggcgtg gtggcgcatg  22260
cctgtaatcc tagctactca ggaggctgag gcaggagaat cgcttgaacc cgggaggcag  22320
aggttgtggt gagccaagat tgcaccattg cactccagcc tgggcatcaa gagtgaaact  22380
ccgtctcaaa aaaataaata aataaagctg gtatgaatat ttatgtacag gttttgtgtg  22440
aacatatgat tttatttctc ttggttggaa tgcatagaaa tgagattgct gggttttgtg  22500
```

```
gcaagtgttt atttttccag ggtacatata atcctgtgag tgtttattta attttaaaag  22560
taattgctaa actgtttgct aaagtgactg ctatattttc tttccctagc agtgtatgaa  22620
tttttttttg aggcagggtc ttgctctgtc acccagggtg gagtgcagtg gtgcgatatt  22680
gtctgactgc aacattgacc tcctgggctc aagtgatcct cctgcctcag cctcctggct  22740
gggaccacag gcatgtacca ccacacctgg tagtttgctt tgatttttag tagagaagag  22800
gtctcactat gttgccctgg gtggtgttga actcctgggc tcaagtgatt catctacctc  22860
agcctcccaa agtgctggga ttatagatat gagcccctgt gcctggcctc attgtggttt  22920
taatttgcat ttccctaatg cccagtgata ttgagcattt tttcatgtgt ttatttgaca  22980
ttcataccat ctttggtgat gagaaactat gtttatgcat tgcttaatga tggggatgtg  23040
ttttgagaaa ttttttcggt gatcttatca ttgtacaaat atagagttta cttacacaag  23100
cctagatggt atacctacta gacacatagg ctgtcgtaca gagtattact cttaggctac  23160
aaatctgtat agcatgttgc ggtactgaac actgttggca gatgtaacat aatgttaagt  23220
atttgtgaat ctaaacatat ctaaacatag aaaaggtgag taaaaataca gcgtaaaaga  23280
taaaagtggt atatctgaat aggtcactta ccatgaatgg agcttgcagg acaggaagtt  23340
gcttgggatg agtcatttat cagtggtgtg tgaatgtgca ggcctaggac attactgtat  23400
gctactgtag acaaacactg aacagttagg atacactaaa ttgataaata tctttcttat  23460
tttgtttttt gagatggagt ctcgctctat cgcccaggct ggagtgtagt ggcgtgatgt  23520
tggctcactg cagtctctgc cttctgggtt caagcgattc tcctgcctca acctcctgaa  23580
tagctgggat tacaggtgcg tgccaccaca cctggctaat ttttgtattt ttagtagaga  23640
cgggggtttc accatgttgg ccaggctggt ctcgaactcc tgacctcagg tgatccaccc  23700
gccgtggcct cccaaagtgc tgggattaca gatgtgagcc accgcacctg gccagagatg  23760
aggtcttgct gtattgccca gggcgttgaa ctcctgggct ccagcaatcc tcccacctca  23820
gcttcccacg tagctgggac tgtgggtgca cgccatcatg cctagccgtt ttgtgaactg  23880
ttgaccaatg ctcttttctg cagacagaaa gttcactgtg gttaggagtt aagactttta  23940
acctctgacc tcaagtgatc tgcccacctt gacctcccaa agtgctggga ttacaggtgt  24000
gagccatcac gcctggtcaa aaatatcttt ctttaagagt aaatttacct taacttactg  24060
gttgatcatt gtatataggt ctgttgttaa ttgaaacatg cgggccgggc ccggtggctc  24120
atgcctgtaa tcccagcact ttgggaggcc gaggcgggtg gatcacaagg tcaggagatc  24180
gagaccatcc tggctaacac ggtgaaaccc cgtctctact aaaaatacta aaaattaacc  24240
gggtgtggtg gcgggcgcct gtaatcccag ctactcggga ggctgaggca ggagaatggc  24300
gtgaacccgg gaggcggagc ttgcagtgag ccgagatcgt gccactgcac tccagcctgg  24360
gcaacagagc gagactctgt ctcaaaataa ataaataaat aaataaataa ttgaaacatg  24420
cggtgcatgt gtttatttgc gatctgactt gtttggaaat atttgcatta tcttccttct  24480
agatttagag catcttgaca gtaggaacaa gtgttttgta caactttgta tgcttagtaa  24540
gttatcaatt aacttgtcgt ggccaggcgc agtggctcac gactgtaatc ccagcacttt  24600
gggaggccga ggcgggcaga tcacctgagg tcaggagttc gagaccagcg tggccaacgt  24660
ggtgaaaccc tgggtttgtt tgtttgttta tttatttatt tattttttgg agacggagtc  24720
tcgctctgtc gcccaggctg gagtgcagtg gcgtgatctc ggctcactgc aacctccgac  24780
tcccaggttc atgccattct cctgcctcag cctcccaagt agctgggact acaggagccc  24840
```

gccaccatgc ctggctaatt tttttatttt tagtagagat ggggtttcgc cgtgttatct 24900
gggatggtct cgaactcctg actttgtgat ccgcccgcct cggcctccca aagttctggg 24960
attacaggcg tgagccacca cacctggcct accctgtgtt tattacaaat acacaaattg 25020
gccatttgtg cgtggctcat ctacagtctc agtgactcag aaggctgagg caggagaatc 25080
tcttgaaccc gggaggcaga ggttgcagtg agcagagatc gtgccactgt acttcagcct 25140
gggtgacaga gtgagactgt gtctcaaaat aataataata atttgttgaa tatgtgactg 25200
ttggtttaat ttttattttt atgagatgga gtctcactct gttgcccagg ttggagtaca 25260
gtggcgtgca gtggcgcaat cttagctcac tgcaacctcc gcctcctgtg ttcaggtgat 25320
tcagcctccc aagtacctga gactacagac gtgcactacc gtgcctgact aatttttgta 25380
tttttagtag aaatggggtt tcaccatgtt ggtcagcctg gtctcaaact cctattctca 25440
agtgatccgc ctacctcgac cttccaaagt ggcggaatta taggtgtgag ccgtggtgcc 25500
cggccagact attggtttgg tttggtgtga tgttatgtta tgttatgtta tgttatgtta 25560
tgttatgtta tgttatgtta ttttaagaca gagtttgtct cttgtcgccc aggctggagt 25620
gcagcggcat gatctcggct tactgcaacc tccgcctccc aggttcaagt gattctcctg 25680
tcttagcctc ccaagtagct gggattacag gcgcccacca ccgtgcctgg ctaatttttg 25740
tatttttagt agagacaggg tttcaccatc ttggccaggc tgttctggaa ctcctgacct 25800
catgatccac ccgccttggc ctcccaaagt gctgggatta caggcgtgag ccactgcgcc 25860
tggctgacta ttggttttat tattaagcag tagtagttga ccctgtcatg tagaaagcat 25920
ggcatttata ggcataccac gtttaatttc ctccccttt tttatttttg gagtacctcc 25980
tgcttgtgag gcttgggaat acagtagtga ataagccaga tgaggtctct ctctttttgg 26040
agcttatgtg gtagtataga ctaggcagaa agttctcatt gcccctgcca ccttatggca 26100
ttgaggtgtt tgagatgctg atgtttactt ctgtctcata aaatcttgaa aggagttctt 26160
ttagatgaag aggaaaacaa aatcagaaga atgggcctgg gtcatgtctg taaacctccc 26220
cacgtcatgg ggaggctgaa atgggaaggg ccaggagttc aagaccaggc tgagaaacat 26280
aacaagaccc catctctaca aaaaatattt tttaattaat gggggatggc agcacacacc 26340
tgtagtcgca gctactacga ggctgaagcg agaggattgc ttgagctcag gagttaaaga 26400
ttgcaggagc tatgatcaca gcactgcgct ccagcccctc ttatcagcag tctggtatgt 26460
tgctaagggt cttgttcttt ttagtgcttc agggacagcc actggctatg cccagaaata 26520
agtatgtttg agaagctttc tgacctcagc ttgaaaaatt gattagggtc ataattaaaa 26580
agggagggaa acaggattga gtgaaccgga cgctaccgtg agtttattct cccagggcat 26640
acataatctc atgtgattac cacatagccc tgttagataa tctgttatcc tgtcctcatt 26700
ttacccatga ggaaatgaag gcccagagag gttaaatgac ctattcaaat tcactcagaa 26760
ggtggcagag atgagttact atcattgtat tttggatctc tggaaagaaa gaaaactagt 26820
gatggtatta aaaaatgtta ttaatagttt cttttaatca accaggaact tgagtcacta 26880
gcttctctgg gtgaaggact atacttcaac agtatgaaaa acggaaaaga aaatgaggaa 26940
ttttggctgg gcacagtggc tcacacctgt aattctagca ctttgggaag ccaagggagg 27000
agggtcgctt gagctcagga attcaagatc agcctaggca acatagtgag gccccatctc 27060
tacaaaaata aattagctgg gcatggtggt gcatgcgtat agtctcagct acttgggagg 27120
ctgactcagg agggtcactt aaacccagga attggaggtt gcagtgagct atgattgcgc 27180
cactgtatac catcccaggc gacagagtga gaccctatcc ccccaccgcc aaaaaaaaga 27240

```
aaagaaaatg aggaatttac atttgtgaca gatacggaat tcagggaatt tagttgttca  27300
tagtctataa atgctataag aagtctccat accttttttt tttttttttt ttttttttgg  27360
agacagagtc ttgctctgtc gcccaggctg gagtgcagtg gtgcgatctt ggctcactac  27420
aagctctgcc tctcgggttc acgccattct cctgcctcca cctcccgagt agctgggact  27480
acaggtgccc gccaccacgc ccggctaatt tttttgtatt tttggtagag atgaggtttc  27540
actgtgttag ccacagatcc cgacctcatg atctgtctgc ctcagcctcc caaagtgctg  27600
ggattgcagg cttgaatcac cgcacccggc cggaagtctc catacttttt aacccaatct  27660
aaaatggtaa ggaaatatat aagaatgtct atttattatt aaatttttttc tatataaaac  27720
atttcagaaa ataaagacta gcatttctga gccaagtggt agtagtggcc atttttctg  27780
gaaaaaaaaa aaaaaagaaa gaaaaaacac atttagctat ctatgatgtg aaaagatgaa  27840
cattttattt aggtaataaa tgttatgtca taaaatacca tttattgtgt gcctattagg  27900
tttcaggaga gctgtgccaa gagcattact tgtatatctt ttaagcctta caacagccca  27960
gcctgtcagg ctggtagtgc catatctgtt ttacagatga ggaagtgatg gattggagaa  28020
attaaggaaa ttgcctttag gtcaaagaga taggaagtga caaagctgag atttttaacc  28080
ttgtgagatt tcaaagtctt tgctttttaa taactgttcc attgcttcta atatagagat  28140
atgacaaaaa caagtaaaaa tcagtgaaga aggctgggag cagtcgctta tgcctgtaat  28200
cccagcagtt tgggaggccg aggcgtgtgg atcgcctgag gtcaggaatt tgagaccagc  28260
ctggccaaca tgacaaaact ccgtctctac taaaaataca aaaaagttag ccaggcgtgg  28320
tgacaagcac ctgtaatccc agctactcag taggctgagg caaggagaat cgcttgaacc  28380
tgggaggtgg aggttgcagt gagctgagat cgctccattg cactccagcg taggcaacaa  28440
agcaagactc cgtctcaaaa aataaataaa taaataaata aaaataataa caataatgaa  28500
gaaaacaatc cggtgattat tgtcagcaat aaaatttctt caatcaacca tgctttagtc  28560
ctggcagttc tctatcagtg agtttcaatc aaaaagtttg tttataattt tttttttttt  28620
aaaattttga aatttggaaa caacatcata aatgatggtt agttttctgc agctccctat  28680
tttggcagat agtctgttgt tactcataat taatttgaac taaaaagtag tgttgtacga  28740
tatcatgggc tgtgaatgtg tttgtgactt gatctgagaa cccacacacc acttaggatg  28800
cttctgtagg aaaattagag tatggaactc acttgcccac gctttccctg tctcagtcca  28860
tgttggtagg ctgcaaagtc tggggctaga aggacactga acaagacttc agcagtacat  28920
gttagtcttc cagagggaag gaatataata gttgagagaa taattccttt cctctgtgac  28980
tttaggcaaa ttcttggcta tgctgttatt tatttgggcc aaacaatatc aggaggttgt  29040
acattttatt cttaattact gcgatacatt aattttatcc atgggtttaa cctagcctac  29100
cttttgctgt tagacttcaa ctctacttgt gttgggttac ccctctgctt aaaaatcacc  29160
ctattcccaa gcctgaggga gtctaccttc aaagctttct atgacctaat ccaaggcctg  29220
tcaaacttcg taaagggcca gatagtaaat ttgttttttt tttttgagat ggagttttgc  29280
tcttgtcacc caggctggag tgcaatggtg ccatcttggc tcactgcaac ctctgcctcc  29340
caggttcaag tgattctcct gcctcagcct ctcaagtagc tggggttata ggcatgtgcc  29400
accacgctcg gctaatttct ttgtatttag tagagatggg ggtttcacca ttttggtcag  29460
gctggtctcg aactcctgac ctcaggtgat ccacctgctg cggcctccca aagtgctggg  29520
attaccagtg tgaaccaccg tgcccagccc gatagtaaat attttaggct ttgcagtcca  29580
```

```
tatacagtcc catttttttg tgtatgtttg cacgttttct ttacatattt taaaagcccc  29640
ttttttttt tttttgagac agagtcttgc tgtgttgctc aggctggagt gcagtggtgc  29700
aatcttggct cactgcaacc tctgcctcct gggttcaggc gattctcctg tctcagcttc  29760
ccgagtaact gggattacag gcacatgctg ccacgcccag ctaatttttg tatttttagt  29820
aaagatgggg tttcgccaca ttggccaggc tggtctcctg atctcaggtg atctgcccac  29880
ctctgcctcc caaagtgctg ggattacagg tgtgagccac cgtgcctgac ctaaaagctc  29940
tttacagtgt aaaaaatatt ctgagcttta agccatgtga aaataggcca tgggcatttg  30000
ctgaccccta atagaactcc attttacctt tctgatcatg tttcccatta actcttcaaa  30060
aatatgacct ccatttaaat caagatggtc tccttcctca ctgcttgtgg aggtccagtg  30120
cccagtgtct gcctcttgct tgctcctcca tcattgttct gccattcgag atcctcatac  30180
ttacccttta agatctagcc caaattttcc atgaaactaa ttctaataat taaaaacttc  30240
ctgtagaact taactttgtc tagtacaagt tagctttctt attcagtagt agcttactat  30300
aaattacaag aataaaaaga ttaccatttt ccctcacact gttttgtgga gaatgcctaa  30360
agttactttt tctttttaca ggtcagtatt cctatttggc atcctaatcc cctttcccaa  30420
atctgaattt tgggatttga agcttgcatt tgagattatg atttgtcttc cttgttgtac  30480
acaggagcag ggactttaca attagtattc gcatccctgc tccttcatac ttcgtgatgt  30540
aaggcaagtt attttcactt atgcttaagt ttcttcccct gtaaaaaggg gatggaagag  30600
gattaaatga attaaacatg taacacgctt aaagcaatgc ctggcaagta ataagtgctc  30660
agtaactttt agctgttctt attagcatgt ttggaaacca gtagaaacta caccagcaag  30720
ttaaggttga aaagtggtat tgatgggctt ggggtagtac agtatgaatg gctacagttt  30780
agcgtttcat taagtttgta tattcattaa ttcattacac atttgatgct gtcagactag  30840
gacagagaca aagatgaatg aaacattatc tctgcttcca ggttacccag tgtagtagag  30900
aaggcaggca tgcagatagt ttaaattggt agcactggga ggggactgcc atgggtgggc  30960
agtgaagaaa aagggcttca aaataatgag agttgagatg gatcttcaag gaagataagc  31020
agttttcagt aaggccatga agagaggagg aagttccagg cgggaagagt ttgtgctaaa  31080
gtacagggat tgctatacac atggtgtatg tagaaaaaat ttggttcaca gtgtgataga  31140
agaattggag gggtcctca ctgaaagtaa ggaaacacat ttggaagaat atgtttcagt  31200
tagaaaatga aatgagctta aagtaaacgc taataaggtt tttaaaatgt aaaatttcaa  31260
cgtatttaga aagagaacag ctggatgaat cttatgtacc tgtcactcag ctttagcagt  31320
tatcagtaaa tggccaacgt tgtttcagct atactcccct ctcctccact gatagtcttt  31380
tgaaggggaa tacaattgtt ttgtggcctc cagaaaggga taagtttatg agcaacgggt  31440
agatcgttgg gagagacttg agtttcctgt caggaagcat tcttggtgca taagtcagag  31500
gtgatatgaa tgccgtggaa gggggtggct tactgtctgg agaactcgag aagatgggaa  31560
tgggcactgt ccagtattgt ggctacttcc acacatggtt ctttaaattt aaaattatgt  31620
tgattaaaat ttaaatattt cagttcctca gccatactaa tcgtatttca agtgcttagc  31680
tgccacatgt gcctaatggc tgcaatattg gacagcatga cataggacat cttcatcatt  31740
gtacaaagtt ctcttggaca gcatgggact agagccctaa gatccttttc tacctgagtt  31800
gtttggattt tttggtgtgt ctaggttgga tctagttgtt catggcttca tgaccaagcc  31860
ttttatccct ttctctagag ggactcaagg ggtaaaggca ctgaaggggt aaaacttcat  31920
atgaagagtg tggtggtggt ggtggtgttt taagacaggg tctcgctctg tcactcaggc  31980
```

```
tggagtccag tggcatgatc ctggctcact gcagcctcga cttcctgggc ttaagtgatc  32040
ctcccacctc agctcccaag taactggaac tgtaggcatg agccaccaca cctgcctaat  32100
ttttaaaact ttctgtagag acgagatttc gccatgttgt ccaggctggt ctcaaattcc  32160
tggactcacc ttggcctccc agagtgctgg gattgcaggt gtgggccact gcgactggcc  32220
tttttttct cctttactac tctagtgtat gctggaatat gaggaaataa ttatattagc  32280
tagcagttat taaacactta ataacatacc aggcactgtt ttaagctatg cgatctgtat  32340
ggaatattac ttaatttcca caaccttatg aaaagatact atttttttc ttttgagaag  32400
gtactatttt catcttcatt tcatagatgt tgaaattgaa acacagagag ctgaagtcac  32460
aggattaagg ccacagagct gagaagtgat ggagccggaa tttgaaccca agcaattaat  32520
gctgatatta gttcttgtgt gaatggtaat tgttttgaaa caatgatcct agatgattat  32580
atgaccggat taatctggca gttgttctgt gtgaatttag agttgccttc ccacctcagt  32640
ttcctaaaaa caaaacaaaa caaaacaaaa caaaaaaaac tctagcttca ctgtgtttgg  32700
gttgtcatgg cctacccct cttgccacct catttgactc aacttttag ggagaaaata  32760
ttcaatacgt ggtataggat ttccctttct aataataatg taaacaacaa caagaagtct  32820
gaaattggaa gaacaaaatg actcacctaa gtgagttaac cttaagaggt ggaacttgat  32880
ttctagattt tagttaattg tctaactgat gtactaaata ttagttactt aagtattaaa  32940
acgggtagac ataatagttg gggagctgct gtagaggggg tagtttgaga aggcttcttt  33000
caggaggtga catttaagtt ggtaactaac aagaaagggg cagccatgtg aatagctgga  33060
gggaagagca ttcttacagt tttactggaa gggggttaga ggtatgtggt acccttatgc  33120
caaagaaaat tagttacttc tatacaacca gtctgattct agaaacctgg atcaatgaaa  33180
tattttgatt atataaaaaa atctgttacc caggtcttgt tgaaatagca ttagaaacta  33240
ctgaaggaca tatagaggag gagtgttgaa aaatggtgat ggatgagcag aatggtgaaa  33300
aataaaaaga catgaagctc tataattata ttgtatggtg acagtaccaa tagagattgc  33360
atgtttttc tccccagttt tttttttgt tttgtttttt gtttttgaga cagagtctca  33420
ctgtgtcact caggctggag tgcattgtcg tgatattggc ttactgcaac ctctgcttcc  33480
tgggttcaag cgattctcct gcctcagcct cctgagtagc tgggattaca ggcatgtgcc  33540
accacgcccg gctaattttt gtatttttat ttgagagggg atttcaccat gttggcaagg  33600
ctggtcttga gttcctgacc tcagataatc cacctgcctc agcctcccaa agtgccggga  33660
ttacaggtgt gagccactgc gcccggcctc ccccagttgt tgaaacaata atggaaggta  33720
attttattct tagattattt aatgtttttc agttatcagg atgtgttaga ttgtttgtgt  33780
atattgtttt gcttgttaat taagtaacac agtgaataag acagacaaac atacgaaaat  33840
gtacatttat tttattttt tgagacagtc tgttgcccag gctggagtgc agtggcccaa  33900
tctcggccca ctgcaacctc tgcctcctga gttgaagcga ttctcttgtg tcagcctcat  33960
gagtagctgg ggccatgggt gcacgccacc atacccggct aatttttata tttttagtag  34020
agatggggtt tcaccatatt ggccaggctg gtctcgaatt cctgacctca ggtgatctgc  34080
ccgccttggt ctcccaaagt gctgggacta caggcatgag ccactgtgcc aggccatttc  34140
atttttggaa cgttcttttt ttttttgaa atggggtctc gctctgtctc ccaggctgga  34200
gtgcagtggc tcaatctcag cttactgcaa cctctgcctt ccgggttcaa gtgattctcc  34260
tgcctcagcc tcctgagtat ctgggactac aggtgcatgc caccacgcca ggctaatttt  34320
```

```
tgtattttta gtagagacgg ggtttcacca tattggtgag gctggtcttg aactcctggc  34380
ttcgtgatct gcccgcctca acttcgcaaa gtgctgggat tacaagtgtg agccaccacg  34440
cccggcctgt ttctggaata ttcataatct tttgttgtca tttcaacagt gctcacagca  34500
gcttcaccag gtgtagattc catcttaaga aaccactttc tttgcttatc catgagaagc  34560
aacacctcat ctattcaagt tttatcatga gattgcagca attcagttac atcttctgac  34620
cccacttcta attttagttc tcttgctttt ttaccacatc tgcagttact tgctctactg  34680
aagtcctgaa cccctcaaaa tcattcatga gtattagaag caatttcctg gttgggcacg  34740
gtggctcatg cctgtaatcc cagtactttg ggaggccaag gagggcggat cacctgaagt  34800
caggagttca agaccagtct ggcaaacgtg gtgaaacccc gtttctacta aaaatacaaa  34860
aattagcggg gatgtggtgg cgggcgccta taatcccagc tacttgggag actgaggcag  34920
gagaatcgct tgaacctggg aggtggaggt tgcagtgagt tgagattgtg cccttgcact  34980
ccagcctggg caacaggagc gaaactctat cttaaaaaaa aaaaaaaaga aaagcaattt  35040
cctctaaaac tcctgttaat gttgatgttt taacctcctc ccatgctcat ggatggcatt  35100
ctcagtggca tctagaatgg tgaatacttt ttagaaagtt ttcaatttat tttgccatca  35160
gagaatggct atgaatggca gtagtagcct tacagaatgt atttcttttt tttttttct  35220
ttttttttga gatggagttt tttttgctct tgtcacccag gctggagtgc agtggcatgc  35280
tatctcggct caccgcaacc tccgcctccc gggttcaagc aattctcctg cctcagcctc  35340
ctgagtagct gggattacag gcatgcacca ccatgcccac ctaattttgt atttttagta  35400
gaggcggggt ttctccatgt tggtcaggct ggtcttgaac tcccgatctc aggtgatctg  35460
cctgcctcgg ccttccgaag tgttgagatt acaggcgtga gccaccgcgc ccggccgtat  35520
ttcttaaata aaatggctta aacgtcaaaa ttatcccttg atccctgggc tatggactga  35580
ttcttgtgtt agcagttatg aaaacattta tgtccttgta cattcccatc atagcttttt  35640
gtcaatgaga agtaattttt tttttttttt tgagacagaa tctcactctg tttcccagcg  35700
tggagtgcag tggcatgatc tcagctcagt gcatcctaca actctgaggt tcaagcaatt  35760
ctcgtgcctc agcttactga gtagctggga ttacaggcgc ccaccaccac gtctggctaa  35820
tttttgtatt tttagtagag atggggtttc acgatgttgg ccaggctggg ctcgaactcc  35880
tggcttcaag tgatccacct gccttggcct cccaaagtgc tgggattgta ggtgtgagcc  35940
actatgcctg gcctaattgg cctaatttca atattgttat atctcaggga atagagaggc  36000
acgaggagaa agagagacaa gctgactgct ggttcgtgga gtagtcataa cacacaacat  36060
ttattaagat tgctgtctta tatggaccgt ttgtggtgcc ttaaaagaaa tcagggtaac  36120
atcaacgatt actgattaca gattactata acagatacaa taataattgt aaattattat  36180
ttacaattgt aaaatacaat cttttcttta ttatttacaa ttattgtaaa atacaatctg  36240
attacagatt actataacgt atacaataat agtggaaaag tttgaaaata ttgtgagatt  36300
tatgagaatg tgacacaggc gcaaagagag cacatgttac tggaaatacg gcactaatgg  36360
acttgcccga ctcggggttt ccacagacgg tcagcttgtc aaaaatgcag catctgtgaa  36420
tttcaataaa gcaaagcaga ataaaatgag gtatgcatgt attgccatca catgtacact  36480
agtaaaatac gttttttttt tcagtaggtg gatcaacctc aaattttaat ataaagcatt  36540
acttaaagga gaatatgggg acattcatga catttcttat atgtacataa aacttcatga  36600
aaataattta atgctatcca gcagtttatt ttagaagtac tggaggctag gcatggtgtc  36660
ttatgcctgt aatcccagca ctttgggagg ctgaggtagg aggatcactt gagttcagga  36720
```

```
gctggagacc agcttgggca atatagtgcg accccatctc tacaaaagag aaaagaagta  36780
ctggagtgtt gcagctctta cagaatttgt ctagcaggtt ttccagtctt taccagaaat  36840
gcccccatgc agaagtagta aatactgatt catgtaaaat aataaacaac tttatctttc  36900
agtttttaaa agacagggtc ttgtaacgtt gcccagactg gcctttaatt cctgggctca  36960
agcgatcctc tcacctgagc cttttgagta gctgagacta caggctgcac ctctgcacct  37020
ggctctgctt gatttttaat tgttgtattg ctgttgcagc tatgtttttt tttttcttca  37080
gtgtgaggat gggcaaactt tttatgtaaa gtctcaggta ataagtattt taggctctag  37140
ggccatatag cttctctgtt gcatatcctt tttttttttt tccatttccc ctcaaattcc  37200
ttttaccata agcaactctt gaggaacata aaaatcattc ttagcccaga agccagacca  37260
aaacaggttg tgggctgtag tgtcctgacc cctgatttaa agattgatag ctttgaaatg  37320
gaaagtttta actttctttt tttttctttc ccttgttctg attgggctgt taattcatta  37380
ggtatttact cagtgtgtat catatgaggc atgattcctc tgctaatttt ggtagtggta  37440
gaaagatact tttgccaagc ttggttgtta ggttttcatt tgtccaagag ttcctgacca  37500
agtgtgaatg gatgttgaaa tcaaggtgtt tctttggcca cacaatgtgc ctttgggggc  37560
tatatctatg tgcttctggt accttctttt aattttcaca aagacactgc ttgccgacca  37620
cactgttttg tctaatgtgg ggctatgacc ccctggaaga ggcatcattt tctgattttc  37680
acagaagcat aatatggtca ggtgatggtc ctgagtagtg ggtatatgac agatacacta  37740
gtaattataa tacagatcta aactggagag ttgaaaacag catcgtatat ttgattgaga  37800
taatcgaagg aagacttcct gaaaagatgg catttgagtt tcaaggctga gtaggattaa  37860
gtattattat ttaaaaaatg ccttggacaa tgcattaaat agagttaaca aatcacatca  37920
cttatagtct ccaattaaaa acattttact taaacataat tttagacttt tagaaaaatt  37980
gcaaagatat tataaagaat tctcctatat atctcacctg tattcttcaa gtaacatttt  38040
accatattca ccttaacatt ttctctgtat tggtaattgt atatgtaaga tttaatataa  38100
aataaaaatt cttattaaac atatgagaga catgatgcct ctttagccct aaatacttca  38160
acttgtatgt actaataaca agggcattct atttcaaaac cacagtacag ttgtcaaaat  38220
aaggaaatta ataattgtgt caaactgtta ttctgtttat agaccttcta atgtccttta  38280
aaacaatcaa caaatcaaca tttttctggt caagaaccag taaatatgta tattctacat  38340
atatatatac acatatatat acacacatat attctacata tatatgtgga atatacgtat  38400
ttactccctc tgtccaagaa ccaatccagg attgttacct tcggttatca tgtatctttg  38460
gtctccttta atccaaagca gtttctttgt cttttatgac ttgacacttt tgaagattac  38520
aggttatttt gtagactgtc cctcaactag ggtttatctg aggtttcctt atgattagat  38580
tcagatattt atttttggca ggaatacaac agaaatgatt tgtgtgtttt tctcattgca  38640
tgatatcaga aagtgcattg tatatattta tcccattact ggggttgtta actttgatca  38700
cttggttaga gttgtgtcta ctaagtttct tcactataaa gttatttttc acttggtcat  38760
ttcatcagta tcttgtgggg agttactttg tggttatata aatactctgt ttctactttc  38820
ccttactata tttagcttct gtggacactt ttgcctgaaa cagttattta ctatggtgtt  38880
accaagtagt gatgcccttt tcttccatca ttctgtctac attttttttt tttttttttt  38940
tttttgaga tggagtttcg ctcttattgc ccaggctgga gtgcggtggc ctgatcttgg  39000
ctcactgcaa cctctgcctc ccgggttcaa gcagttctcc tgcgtcagcc tcccgagtag  39060
```

```
ctgggattac agacatgcgc caccactcct ggctaatttt gtatgttcag tagagacagg  39120
atttttccat gttggtcagg ctggtctcca actcccgacc tcaggtgatc cacccacctc  39180
agcctcccag agtgctagga ttacaggcgt gagctgccac accaggcctt ctttttctct  39240
tttaagagat agagtcctgc tttgtcacca aggctggagt gcagtggcat gatgatagtt  39300
cactgcagcc tcaaactcct gggctcaagt gaacctccca tctgtagctg ggactacagg  39360
cacctgcata acacctgact gtttttttaaa actattttag agatggggtc ttgcgaagtt  39420
gctcaggatg gtcttgaact ccgggtctta agtggtcctt ctgcctcagc ctctggatta  39480
gttggcatta caggcatgag ccattgtacc tggcaagtgc atattttctt tttttttttt  39540
taaggtggag tctcgaggcc gggcgcagtg gctcacacct gtaatcccag cactttggaa  39600
ggccgaggtg ggtggatcaa gaggtcagga gatcgagacc atcctggcta acatggtgaa  39660
accctgtctc tactaaaaat acaaaaaatt aactgggcat ggtggcacac gcctgtagtc  39720
ccagctactc gggaggctga ggcaggagaa ttgcttgaac ccaggaggtg gaggttgcag  39780
tgagtcaaga tcatgccact gcactccagc ctgagcgaca gaggtagact ctgtctcaaa  39840
aaaaacagaa agacggagtc ttgctctgtc acccaggctg cattgcagtg gcatgaactc  39900
cgcctcctga gttcaagcaa ttcttgtgcc tcagcctccc aagtagctgg gattacagac  39960
atgtgccacc acacgtggct aatttttata gttttagtag aggtggagtt tcaccatgtt  40020
ggctaggctg gtcttgaact cctgacttca ggtgatccac ccgccttggc ctcttgaagt  40080
ggtgggatta tgagtgtgag ccactgtgcc cagccaagtg agtatttgct tatgtagtat  40140
tttaatttta tgattttttt ttctttgaga cggaggtttg ctcttgttgc ccaagctgga  40200
gtacagtggt gccatctcgg ctcactgcag cctccacctc ctgggttcaa gccgttctcc  40260
tccctcagcc acctcctcct gaatagttgg gattataggc gcctgccacc atgcctggct  40320
aatttttttgt atatctagta gtgatggagt ttgagcatgt tgccaggctg gtcttgaacc  40380
tctgacctca ggtgatccac ctgccttggc ctcccaaagt gctgggatta aggcatgagc  40440
caccatgccc ggccagagac tgttcattta tttttttttt ttgaggcgga gtctcgctgt  40500
attgcccagg ctggagtgca gtggcacaat ctcggctcac tgcaagctcc gcctcccaag  40560
ttcacaccat tgtcctgcct tagcctcctg agtagctggg actacaggtg cctgccacca  40620
cgcctggcta attttgtttt tgtattttta gtagagatgg ggtttcagcc cgccttggcc  40680
tcctggagtg ctgggattac aggcgtgagt cagggcgcct ggccaatcat accttctttt  40740
actgcattaa ttatggtttt ctttcgttct taaaacatgt ttatagtgac cacttttgaa  40800
attcttatta agtcagacat ctggttatac aagcaatttc tattgcctac ttctttttcc  40860
agtgggtggg gttatacttt cctgtgtctt agcttgtcgt tttttttttt gttgttgaaa  40920
actggacatt ttaagtaatg tagtaactct ggatacctca ttagcctatg gttgggggtg  40980
gtggttgtta ctgttatttg cttatttgtc taatgactgg ctgaatgatt ttagtgttct  41040
atccttcttc cctccctgta cagtgtgaca cgtctgatgc tagttttctt gggatgcagc  41100
cttgggtatg cctaccatca ctctagaatc acagtgattt tggcatggct ttgtctcttt  41160
tcctgactgt acccagctgt taagctacac taattactag gtgatgctgt gtagtcattt  41220
cttggtgtcc ttgggggatt ggtcccagga cccccccgtt ggatataaaa atttatggat  41280
gctctagtcc ctcataaaat ggcacagtat ttgcatatac cggtgcacat cctcctgtat  41340
gctttgtcat ttctagatta cttataatac ctaatatggt gtaaacacta ggtaaatagt  41400
tgttatatat tttttatttg tcttattttt attgtattta tttttaagtg tttttaatct  41460
```

```
cgagtgattg aatctgagga tgtgaaatct gcagatatgg agggcctgca ttgttttccg  41520
tggagctttg ggcctaaact gctccacaga ctgatctgat caaatttgcg cttctttgaa  41580
gggatagttt ctgagatcag tgtttgaaat ttgttccaat ccacagagga gtcctcccag  41640
ctctctttcc ctagttctgg ccaccaaact agacaactac aatttagcac ttatctccaa  41700
tgattctcct cctaccaagt gcctttgaaa gcatcattaa ctctttcata ccttgttgca  41760
aatgaaattt ctttgggaag agattgtgag ttttttttct cctaaattat ggtgcaatat  41820
aagtaatata ccattttaac aattttaagt gtattaagtg tttttttttt ttgtagtttt  41880
tttttttttg ttttttgaga tagtcttgct ctgtcgccca ggctggagtg cagtggcacg  41940
atctcggctc actggaacct ccacttcccg ggttcaagtg attctctggt ctcagcctcc  42000
ccaaatatct gggattacag gtgtgcacca ccacgcctgg ctaatttttc tatttttagt  42060
agaaacgggg tttcaccata ttggtcaggc tggtcttgaa cttctgagct cgtgatccac  42120
ccacctcggc ctcccaaagt gctgggatta caggccttag ccaccacacc tggcctatgc  42180
attgctttta tatgtatttt aaaattcata agttctcctc ctatgatgtt tttgtcccat  42240
gtgatttatt tgttaaaccg tcatctttgg ccgggcgtgg tagctcacgc ctgtaatccc  42300
agcactttgg gaggctgagg tgggtggatc acaaggttaa gagatcaaga ccatcctggc  42360
caacatggtg aaaccccgtc tctactaaga atacaaaaat tatctgggca tggtgacgcg  42420
tacctgtagt cctagctacc tgggaggcgg aggttgcagt gagccaagat cgtgccactg  42480
cactccagcc tggcgacaga gtgagactct gtctcagaaa aaaaaaaaaa caaaaaaactg  42540
tcatttttta tgttgcattt actgcattct ggatttaaac tgtgaggaac ctcatggtat  42600
cagttaatat attcttccat cttaatgttt ctcgtaaact ggtagatctg taaacttgat  42660
taggtctatc ctattgtatc acatcagaag cagaaggtgc tttttttttt ttttaaggga  42720
aattgtgtga aagtagacag aatggtaaag tgaacccctg cacacctatc acccagcttt  42780
aatagttatc agctcatacc attcttgttt gatttacaac cccattcatt tctcccttct  42840
gtattattat tatttagtta attatttttt gagacagggt tttgctctgt caccaatgct  42900
ggagtgcagt ggcataatca cagctcactg ctgtcttgac ctcctgggct caagtgatcc  42960
tcccacctca ccctaccaag tagcggggac cacaggcgtg tgccaccatg cctggctagt  43020
tttttatttt ttgtagaaac agggttttgc tttgttgccc agactgatct caaactccgg  43080
cactcaagtg atcctcctgc ctcagcctcc taaagtgctg ggattacaag catgagctac  43140
cacattcagc atgtaaattt ctttatatta atttgactgg cattttaagt cacacttgaa  43200
tttcatattt ggcaactatt aaaagcatag agtcctggat attagtgttt tgttaaacct  43260
gatctatcta atcataaata tacttaggtc taaaatatgc tcttggcctt tgtttattgc  43320
ggttcagtat ttgttactat attaaatagt aaaatatttg gtttgagata ctaatgaaaa  43380
gattaaaagt aaagcataac ttgaatggat acaaaaagaa acaagaattt agacttcagt  43440
ggatttcaga gaatactgct tcgatatgct aacattcctg ttgggtgtcc aaccgtgtca  43500
tagatcagtg gaaattagtg gtttctgcac tttactgtac tgttttttta tatgataata  43560
ttttcctggt tgaatgattc gttcttttga gtaaactcca tggtcaaaca attacttttt  43620
attagtcaaa gatgtaacca cataatcact aaaaagaaca gtgtgactta tttaaagggg  43680
attatgtttt taagtctttt atatagcttt gtagggaggc catatgagtt taaggacagt  43740
tcgtggcatt tgttcaaggt tttgtaactt ggcatctcag cagccaccag gataccagat  43800
```

```
catcgttcta agtaagattt aggcatttta gccttcatgt acagactata agtacacccc  43860
cccacacccc taccaaaact gtaaattcaa atgatgtttg aaaaagcata gaatttttgt  43920
taggcgaggt agtttattcc ttgtgataca gttccagaga ggcagcataa cctaggaatg  43980
aaaaacttag acgtggaatc agatacacct ggtttaaata ccagctctac tgctcatgaa  44040
ctggatgatt ttggtcaaga tacttgactg ctgaggttca gtttcctcac ctgtaaagta  44100
gaggtgatag attagacatg ttgcatgtga agtacttagt atggtgtctg gttttgtagt  44160
aagatctata aaagataaat tattagtcat attccttaga cttcaggaat ttatctctgt  44220
gccatgtttg aggcaaacag ttacagaatt agaatgttag aaatgaaagg aatcctagat  44280
gtcatttaat tcaagtccat tgttttctgg atgagagaag aaagtgagga aaagtgacag  44340
agttggagac caagctagga ctggcctcag aatgttaaga gtactcttct agggatcgac  44400
cagtcgtgtt actagacttt ttggatctga attgtgcttt tccttgaatg ttttgaattt  44460
tggcttgagt gttgtgatta ttttattaaa atgagattcc agtcctattg tcatgactaa  44520
tgtttatgag aaatataaca tttcacttta atgatgtttt ttaattattc taaggggcct  44580
aatctttttc agtggaataa gctttaggtt gtattatatt ctataattca cttgaaaata  44640
gaattcatct ttacttgaca gccaaatttt gtgtactgca tcttttctga gggagagagt  44700
tggcaaggaa aggcacttgt tacaacgatc cacacatata gacgcatatt atttagaaat  44760
gaaagtgctt tgaatgattt agcttatttt cagttttttt ttttctgcag ttgtaatcat  44820
atgacctgtt tttctttctt tttttttttt tgagacagag tcttgctctg tcaccccggc  44880
tggagtacaa tggggcggtc tcagctcact gcaacctcca cctcccaggt tcaggcgatt  44940
cttctgcctc agcctcccta gtagctggga ctacaggcgc atgccaccac acctggctaa  45000
ttttttttatt cttagtagag atggggtttc actgtgttag ccaggatggt ctcgaactcc  45060
tgaccttgtg atctgcccac ctctgcctcc caaagtgctg ggattacagg catgagccac  45120
tgcgcccggc ccatatgacc tgtttttctt ttatagatgg gggagaaata tgggaagtga  45180
cttggtgtca gtcatctgtg ttggttaaat caagaatata atccgtgttt tgcttctgaa  45240
tagctcttta taacagtgat tggttacttt gggagtaaag attattattt agagacagag  45300
tcttgctttg tcgcccaggc tagactgcag tggaatgatc gtagcctact gcagcctcag  45360
actcctggac tctggtgatc ctgcctcagc ctcctgagta gctaggacta gaggtgcatg  45420
ccacatgcct ggctataatt attattaatt tacgtttagc attagttttt ttcttccagt  45480
aggctatttt actttattta tttgattttg atgaagtttg attatttcta gtttgcttcc  45540
ttctatgacc cctacctgtt gtgggtctcc aggcaagcag tgcataggta gagccatcct  45600
taggtagcct ttagacttaa tattaggtga gctctcccca cagatagcct ctcctttatt  45660
tgaatggaat tatattttaa gtttggaaat atttttcagc ttatttagcc tgttgaattt  45720
aataaaaata atatttaatc ttttcagagg tcgaaacagt aacaaaggac tgcctcagtc  45780
tacggtgagt aactttaatg ttacttattg ggaaaaatta gtagctaaaa catgatctct  45840
aaccacagac caaatgccaa ggcaaaagat tcccttcttt tgaattttgt catagataac  45900
ttgactgttt aagtatgtta ttagcctata tgtgtttttt taatgactct gtataaaatg  45960
tacaattact tgttgtatta gtccattctt acactgctaa taaagatata cctaagactg  46020
ggtaatttat aaaggaaaga ggtttaattg actcatgctc tgcattgctg gggaggcctc  46080
aggaaactta caatcatggt ggaaggggaa gcaaacacat ccttcttcac atagcgacag  46140
gagagagaag tgctgagcaa agcagggaaa gccccttata aaaccatcag atctcctgag  46200
```

```
aactcactca ctatcatgag agcagcgtag gggaaactgc cccatgatt cagttatctc  46260
cacctggtct tgcccttgac acacgagaat tattataatt aaagataaga tttgggtggg  46320
gacacagaac caaaccatat catttgtaaa tagtattttt gtcacgtgta ataacaagaa  46380
caagtcgctt gttcttttct aaatgactaa gtgcaaatct aagtgaaaaa cctccaaaag  46440
atacgtagaa caccaagagt ggagtctgca gagttcttta tgctttttat tttgaattaa  46500
tgtgcttttt ttctgctgct ttcatttttc tcctttggct ttctggtctt aaattttgga  46560
atgttatcaa tgaaattgaa ccggacatga agggcagaaa ctataagtcc cacatgatgg  46620
aagaaataaa tgagaagcta tcacaaattt ttgagacttt gcctttatta gattgtttta  46680
caagaatcag gaagatatac acgtatatgg tagtaatatg gagtagtgtg gttgatcaga  46740
cttaagcact gtcactgatg ctgatatgct gggagaacct agtcagggtt cttctatgaa  46800
ggtatgacct ggcttcctac cccatttatt tatacttcac ccttcttagg gtacatttct  46860
gtgagtttta acaattgcat acaatcagtg taactaccac cacaatcaag ttaatagaac  46920
agtttcattg cccaccaaaa tccctcaaat cacttttcag tgaaccctcc tctctctcca  46980
accattgatt tgtcttccat ccttacggtt tgtgtccttc ctcctctatg gaagtttact  47040
cttgcttttt tatgtcatgt ttagtcaaaa caccattagt tggtttgact gataacactt  47100
gaaaacctga ccttctgttc cttctgttct ctatggaagc aaaatattaa ataaacaaaa  47160
tcttccctta atacatgtaa gatatcataa acctaactaa acatttgca acaaataata  47220
aacgttagct ttatatgcaa atgtaaatac aggctgagca tccctaatcg gaaatgctcc  47280
aaaatttcat attttgaatt agggatgttc aagcactaag tataatgcaa atatccccaa  47340
atccgaaaaa aatccgcagt ctaaaatact tctggtccca agcattttag atgaggaaga  47400
ttcagtttgt actaatttct aatagttttt ttttttttta atattccaga tttcttttga  47460
tggaatctat gcaaatatga ggatggttca tatacttaca tcagttgttg taagttatta  47520
gattattggg gataaactgc cttgggggta gaataaagta attccatgaa gttaaaatgt  47580
ggataaatga ttgtcaaagt aacattgctt agatcatgtt tagtcaggat gatttagaga  47640
aatagattag aactcctttt atccagtcta atataattca ttgtaaaagt acagttggtc  47700
ctctgcatct gtgggttcca tattcatgga ttcagccaac cttggatcaa aaatatttgt  47760
taaaaaggcc aggcacagtg actcacgcct gtaatcccag cactttggga gtttgaggtg  47820
ggcagatggc ttgagctcac aagtttaaga ccagcctggg caacatggca gaactccgtc  47880
tctacaaaaa gtaaaaaaac tagccgaacg tggtggtacg tgcctgtagt cctagtgact  47940
tgggaggctg acgtgggagg attgtttgag cctgggaggt ggaggtttca ctgagctgag  48000
ataatgcccc tgcactcagc ctggtcaaca gtgccagaca gaccccttct caaaaaaaaa  48060
aatttttttt tttttttttt tttttttttt ttttgagaaa aaagaggcat ggttgcgtct  48120
gaaccaaaga tgtacggacg tttttcttgt cattattcct aaaacaatac agtatgacaa  48180
tttacatagc atttacatta tattaggtat tacaagtaat ttagggatag tttaaagtat  48240
ttgggagaat gtgcttagtt atatgcaaat actattacat tttatgtaag tgacttaagt  48300
attatgtaat tcggtatctg aaggaggtcc tggaaccagt cccctaccaa taacaacaga  48360
tagctgtatt cttgttaacc ctgctgtgtg tgtaaaataa tgttagtagt tgattgtctt  48420
ttgtacatta ttttgtcact taaaatagct ggggtcagaa atgtttgact tcagtattaa  48480
aattcgtact gcaaactctg agtagagcct cctgaagaat ttcaagagtt cagtgtattg  48540
```

```
ttaatgtttt gaaatttttt tattgttttg ttagtgaata cctaatattg aatgaagcct  48600
gatgaggtat aaaaagtaaa atgaaaacaa atatccctgg tgaccgggta gtatactgtt  48660
tctttgataa ataaattata tgtttttagg gctccaaatg tgaagtacaa gtgaaaaatg  48720
gaggtatata tgaaggagtt tttaaaactt acagtccgaa ggtaattttt acttttttc  48780
tttttcttac aaagtaaaag aacattttca tagtcagtgt tttacctagt ttttaaagcc  48840
actttgaatg attttacttc tcagtttcaa atactgatta ttttatagac tggtttgtgt  48900
aatcagagag gcttcttgat gtgtgtgctt attaaaatat ttcaaccatt tttaagcatt  48960
gtgagctaat agagggatgt ggtggtttgt tttttcctct taaaaattat tattaatgta  49020
cttaagacaa accatagaaa caaaaaacat ttagatatga ggatttttaa atgatggaat  49080
ggataataga tcatatgcct gggaaaaagg gtatgattct cttgagatta tttttgtcaa  49140
aggcatataa gaactggtac cttgatgagc taaagaattc ctaacaaatt ttattttgta  49200
aaggtttgga gtacttactt gtgtttttca ttttagtgtg atttggtact tgatgccgca  49260
catgagaaaa gtacagaatc cagttcgggg ccgaaacgtg aagaaataat ggagagtatt  49320
ttgttcaaat gttcagactt tgttgtggta cagtttaaag atatggactc cagttatgca  49380
aaaagaggtg ggttttgatt tcctaaatat gcctcatggt ttattagatt tattcaagca  49440
aagattttca cagtgatctt acaaactttt tttaaagaaa tatctgggct gggtatggcg  49500
gctcattcct gtaatcttag cacttaggga ggctgaggcg ggtggatcac ctgaggtcag  49560
gagttcgaga ccagcctggc caacatggcg aaaccccgtc tctactaaaa atacaaaaat  49620
ttatttttgt gtgtggtggc gtgcgcctat agtcctagct actagggagg ctgagacaga  49680
attgcttgaa cccaggaggc agaggttgca gtgagctgat accgcaccac tgcactccag  49740
cctgggtgac agagcaagac tccgtttcaa aaaaaaaaag aaagaaaaaa gaaatatcta  49800
ctttctagaa tagcccaagt aaggtaattt tttagaaaaa tgagaatgtt aatgcatttt  49860
tgttggaaaa caattagaac tttagagaaa aattaaatag agtttttgtg atctcttaaa  49920
aaattagttt gtaaagcatt ttctacagtt ttgtggtcaa gaatgctact gattatattc  49980
aactgaaaat ttcttgtccc atttggccta caatgcttta gtttataagt gggcatgtgg  50040
caaatctgga aagaaatcaa agtataaggc taaggaagaa aggtagagaa cggttggtag  50100
aaaacaattg tctaatgaaa atgaaaaagg gtgaagaagt agaacatacg tattttaaaa  50160
atattcagag tatgagacaa ggttttgaga atttaaaagc gattatgtag ttatattaaa  50220
aatttagtct ctttttaagt gtccattgat gaacaaagtg ggaattcctg ttactcattt  50280
gcaaggcatt attgagtgtt cagtaacacg ttgcaaggca cttctgggca atcctgaact  50340
tggttctcaa attctttttt tttttttttt tgagacggag tcttgttctg tcccctgggt  50400
ggagtgcagt ggcacgatct cggctcactg cagcctctgc ctcccaggtt caagcgattc  50460
tcctgcctca gcctcctgag tagctgggac tacaggcgtg tgccaccaca ccaagctaat  50520
ttttgtattt tttgtagaga cagggtttca ccatgttggc caggatggtc tcgattgttt  50580
gacctcgtga tccgcccgcc tcggcctccc aaagtgctgg aattacaggc atgagccact  50640
gcacccagcc ggttctaaaa ttcttttatt tatttgtata tgccaaattc tgtagtgaaa  50700
tacgtaattc tgttgtaaat tgtagttcag tacaatttga ttttcactat tcaaatctat  50760
accaaaagct gtttttattg ttgggctgat tcttctacac tgttacttgg aaataataat  50820
ataccaggat tctttctctt agacttagga gtctttctct ttgcttgctt tttcagaggc  50880
taacagtact gggtattctt taactgtctt gatatgctga tgaaagcaca gtgttctgtt  50940
```

```
tttgaatctt ctcaaatgtc cttgtctttg attcacaact ttttgtctta agaggccttc  51000
agcatcccat acaaggaaac aagtcttttt ttagctgcta cctttggagt tgattttgtt  51060
tatgtctagg agcactaaat tatttatact tatactattg aaatattcct ctgttataaa  51120
ttcaaaaatt gactttggaa gataaaattt tagttgaatt taatacatag cactctggaa  51180
agagtattgg ccacaacaaa aaaaaaggtt ccctactcta ttggatacca ggtcatttaa  51240
cagccattta cggtatgcat tgtctttttg tttttatgat gaattgatat ttcccaaatg  51300
tggaagagtg aatattactt tgagatgttt gtgatagtcc attccttgct cctcttcaaa  51360
attaatgtca ttaaattttt attactttat tagatcttca tttctcagat aattttagtt  51420
cattatagaa aggcaagaaa atacagatca gagtgacaac tttgaaaatc tcactctact  51480
cataagggga tgggtgtatt ttgctatata ttacaaaatt agttttcttg atgaggacat  51540
ccactattgg agtaatttca ggtatcttat tttttctttt ctctctcttt tttttttttt  51600
ttttggagac ggagtttcgc tctgttgccc aggctggagt gcagtggcct gatctcggct  51660
caccgcaacc tctgcctcct gggttcaagc gattctcttg cctcagcctc ccgagtagct  51720
ggttactgag gcatgtgcca ccatgcccgg ctaatttttg tatttttagt agagacgggg  51780
tttcactatg ttggccaggc tggtcttgaa ctcctgacct tgtgatcctc ctgccttggc  51840
ctcccagagt gctgggatta taggcgtgag ccaccacgcc tgggcaggta tcttatttca  51900
aaacttacag tggtttagtg aattatacaa ttgcgtccag tgcgtagtat cctgaaaata  51960
gtattaagtc atgtgtttag gacatcaggt ctcttaagct aagactatcc aggcagaaat  52020
tgccctcttc tataaaagaa gaaaagtatt aattaggaag tactatcagt atggagaaaa  52080
ccattttaga attattaatt ggcatggttt ccttcttttt ttttttattt cgagatggag  52140
tctcactcta tttcccaggc tggagtgcag tggtgcgatc tcggctcact gcaacctctg  52200
cctcctgggt ttaagcgatt ctcctgcctc agcctcccga gtagctggga ttataggcac  52260
ataccaccat gccctgctaa tttttttttt tgtttgtatt cttagtacag actgggtttc  52320
accatgttgg ccaggccgca tggttttcct taataacaaa attaaggcat ttattactgc  52380
atctagattt tttttatttt ttattagaga cttactcaga ttactcccaa agtaaaggaa  52440
ggtatggttt aatcaatgct tcttaatgct gggttcacgt ttagtcacct ggggagtttt  52500
taaaaatgtt ctcacttcta gggatcctgg tttaattata attagcctgg gtgaggctct  52560
ggacagtcag ggtgtgagct atgggtttca tgtgatgaga tcccaggagt ggctctgttc  52620
tgtggccttg agaatttgtg ctttctaggc caggtgcggt ggctcactcc tgtaatctca  52680
ctttgggaga ccaaggtggg cagatcattt gaggtcagga gttcgagacc agcctggcca  52740
acatgttgaa accccgtctt tactaaaaaa gtaaaaaatt agcgggacgt gatggcacat  52800
gtctataatc ccagctactt ggggagaggc tgaggcagaa gaatcgcttg aacccgggag  52860
gcagagattg cgagatcatg ccactgcact ccagcctggg caacagaata aaaaaagaat  52920
ttgtgcttta ttttcttgcc tcacagtccc ctttctgtct cagaattggc aactgcctga  52980
aatagtctct gctgttatca tttgatagta cttttccaca tcttgaatgg atagatagag  53040
tgttttttat aatagaagtg gatgaatgat tagagtatac taatatgaca ttgtattttc  53100
ctaaaagata tgaattgatt tcatttctga gcttttataa ttctcttctg taatagtctg  53160
tcaaattatt aaggttgata atattaacta aaatttgagt gcatattcta tgtgccagac  53220
tctgtgctaa cagatttacc tacatttgtt cacataatca tcacaagttg tttctgtagt  53280
```

```
agatacagct attatccacg tcatagatga ggaaacaggc atatttagga aacttgctaa  53340
agtgaggaca caaatctagc ttttctactc taactcatgt tcttaacatt atactgcagt  53400
gacataaatt atgtggtttg gtttgttgtt tatctcagtt gtcataagtc gaattaatgt  53460
ttgtttgttt gttttgagac agagtcttgc tctgtcgccc aggctgggta cagtggcgtg  53520
atcttggcgc actgcaacct ccacctcctg ggttcaagca gttatcttgc ttcagcctcc  53580
ctaataactg ggattacagg cacgtaccac cacacccggg taatttttgt atttttagta  53640
gagatggggt tttaccatgt tggccaggct gatttcaagc tcctgacctt aggtgatcca  53700
cccacctggg cctcccaaat tgctgggatt gtaggcatga accactgtgc ccagccagta  53760
agttccatgg ttgttaaagg atttctccac aaataaagct aaaagtaaaa aaaaaaaaaa  53820
aaaaaaaaaa ttctcaagca atataagatg cagactatta tgttgttcaa gttttttttt  53880
ttttttttta atctttggct ttatttttgg ggaaaccttt tttttctttt ttgttttcct  53940
tgggacggag ttttgctctt gtcgcccagg ctggagtgca atggtgcaat cttcgctcac  54000
tgcaacctcc gccttctggg ttcaagcgat tctcctatct cagcctcccg agtagctggg  54060
attacaggca tgtgccacca tgcccggcta actttgtatt tttagtagag actgggtttc  54120
tccacgttgg tcaggctggt cttgaactcc tgacctcagg tgatccacct gcctaggcct  54180
cccaaagtgc tgggatcaca agcgtgagcc accgcgccca gccagggaaa cctttatttt  54240
gaggcggagt ctcgctctgt cacccaggct ggagtgcagt ggcgtgatct cagctcactg  54300
caacctctgc ttcctaggtt caagcaattc ttctgcctaa gcctcccgag gagctgggat  54360
tataggcgtc tgccaccatg cccagctaat tttatattt ttagtagaga cggggtttca  54420
ccatattggc caggctcttc tcaaattcct gacctcatga tccacccacc ttggcctccc  54480
aaagtgctag gattacaggc gtgagccacc acactcggct gctggggaaa ccttttaaca  54540
tgagtaaggt cagtgtgact tttaagttct tgatgctaac atcattgatt tcaataaagt  54600
ttaaaagtta tattcatgca tatatgcaaa tgaataaaag gctttgaaat agtgacttct  54660
tacggtacag tgaataagtt tcctttggtc tcttgaatgt tatacatgtt ccagtttgat  54720
ttactgagaa actgaaagta cctttacgtc atatgagctg tgagtcacct tggcacattc  54780
ataattagaa gagaccatca gattatcatt ggaaaatcag tttgtattta tcctttattt  54840
gaattccagt gcagacagat ctgaggttct cttcattttg ctaaaacttc ttagggcctt  54900
cagtcgcttt tggctctgta ttcgtgtatc tttggaattg tcctgttatc tctgcttgtt  54960
ttttacttga ttttccatcc atttccagta ttcctttctc ctctattttt ttccttcatt  55020
ttctttctgc tcttcctgtt gcgccattat tcatgttttc ctctttactc caactcaact  55080
atggctttac ttctgtttcc ttattccatt gttcctcata ctttttccta ctgcttcatt  55140
ttctttgcag tattctcagc ctagatgata ggggtcagca aatctgctca tcagtaaata  55200
aattttattg tagcatagct atgcccatgc gtttgtgcat tgtctatggc tgttttgatg  55260
gctgtagcca tagagttgag tagttgtagc tgactgtagg acttgcaaag ccagaaaatt  55320
tgactgtctc tttacagaaa agtttgccag ctcttggcct aaatcatatt ttccgctgca  55380
tttagggctt tttaggactg atcaaaaata catgctatac tggctttggt gaagtaacag  55440
aatgtgctct gtcctttaaa cttacaacta attgcatgct ttgattctaa tactgtataa  55500
tatcctgcga ttcttattca tgaccattct aattggattt agtctgaaga attacttttg  55560
cttaacagat tctttgtcac atttagtgaa aaatcataaa aggggaaggt tggttaatgg  55620
aaaagatctc catcaactaa ccactacctt ccttatctac aaatttatct tcttcctccg  55680
```

```
tgccatcttt tttttttttt ttttcagatg atcttgctct gttgcccagg ctggagtgca  55740
gtgatgcaat cacagctcac tgcagcctcg acttcccagg ctcaggtgat cctctcacct  55800
caacctccta cataactggg actgtatgtg cacatcacta tgcctgacta attttttata  55860
tttatatttt ttgtagagat ggggtttccc tgtattgcac aggctggtct caaactgctg  55920
ggcctaagag tcttcccacc ttggcctccc aaagtcctgg gattacatga gtcaccgcac  55980
ccggcctcat tattattttt cctctggttt tagtagagag gatttttaag ccaacttcaa  56040
tcatgccctt gactctctcc cttctactta cctccttgtt ctctttttct ttttcttttt  56100
ttttagatgg agtctcggtc tgtcacccag gctgaagtgc agtggcgtga tttcagctca  56160
ctgcagcctc agcctcctga gtagctgggg ctataggtgc ctgccaccac gcccggctaa  56220
tttttgtatt tttagtagag atggggtttc accatgttgg ccaggctggt ctcgaactcc  56280
tgacctcaag tgatcacctg cctcagcctc ccaaagtgct gggattacag gcgtgagcca  56340
ccacgcctgg ccatcttttt ttttctcctt gctcttttat accacttctc tgtttctggg  56400
ctcttcaaca tctgcctttc tagttaatct ttccctttag catgaaaacc tattcacttc  56460
ctgctcatcc taaaaaggat tctttttttgt tttgttttgt ttttgttttt gagacagagt  56520
ctcgctcttg cccaggctgg agtgcagtgg cactatcttg gctcactgca agctccgcct  56580
cccgggttca cgccattctc ctgcctcagc ctcccgagta gctgggacta caggcacctg  56640
ccaccacgcc cagctaaatt tttgtatttt tagtagagat ggggtttcac cgtgttagct  56700
aggatggtct cgatctcctg accttgtgat ccatctgcct cggcctccca aagtgctggg  56760
attacaggca tgagccaccg cactgggccc aaaaggattc tttttaatcc tgaattcttc  56820
tagccattat cctgcctaag gctacgatta acctctaact gccaggtcct ttggaatctt  56880
tttctgtctt tattgctgca cttgaatgtt ggtttcaccc tccttcagaa tttcctcttc  56940
tgtatttttt atgtttattg atcattcctt ccctgcctca ttcctgggct tcttttcctt  57000
cacacacccc ttagatgtgt gtccccagtg tttgtttctt tgcctgctgc tcttgccaca  57060
tgacacacac tgccagctac cacacacaag ttccctccta tcatgtgtgt atcattgccc  57120
ttataccatg ttgtattaaa attatatgct tgtctcccct gttacagttt gagctctttg  57180
tgctccaagt aaagacagtg atactgtctt tattatttat tctcatggtc tagtatagtg  57240
ctttggcaca tagtacaggc tcaatataaa tgtgtttgaa taaatgaaat tcagtgcctt  57300
aatacacttt tgtagaagca ttattttatg gaaagaatga aaaagctgta agtggtctta  57360
catatatagt catccagcag atacttagag agctctggga tgtgttcctt gctgtgcttg  57420
ttgctatgga cagtacggag aaatacaaga atctattttg ggtccctttt gagaacctag  57480
tgaaactgtg tacctagtga aactgtatac cctcacccta gaaaaattta cacacatgta  57540
gattttacat gtaattcttt taaaaattaa tttttttttct ttttttaaa gaaacagggt  57600
catgctctgt cactcaggct ggaatgcagt ggtgtgatca tggcttactg tagcctcgac  57660
ctcctggctc aagcgactct cccacctcag cctcccaagt agctggggct acaggtgcac  57720
gccgctatgc ccggctaatt tttaaaaata ttttatagac actggttctc actatgtttc  57780
ccaggctggc ctttacctcc tgggttcaag caatcctcta ccttggcctt caaaagtgat  57840
gggattatag gtgcaagcca ctgtgcccac gctaatgtaa tttcatggtg ttcacagttt  57900
cttcagggag ttcatatacg ccatgtactc tattctaagc atttttagag ttagagatag  57960
caaagcacgt gaataaattc aagaaaaatg gaatgttgta ctgcatgaca ttgaatatca  58020
```

aatggagtca gcgatgcaaa taattgtcta gattttacaa aaaaaattag cctggtgtgc 58080
tggtgtgcgc ctctaatccc agctactcgg gaggctgaga caggagaatc atttgaaccc 58140
agaaggtgga ggttgcaatg agctgagatc gtaccactgc actccagcct gagtgacaga 58200
gcgagactcc atctcaaaaa taaaaaataa aagaattgtg tagattttag tagttggaag 58260
aagttggagt gttaatgtgt aattagagaa cagtgagaaa taaaattcta cagattgttt 58320
tattctggtg tgctgttgtg ttctcatatg gttgtctttt tggtcttgat agtgtatcag 58380
taacagagta cgagtaacaa acagggatct cttctgaacg gcgtgacatt agaaaagctg 58440
tttacggcct caactttgct gtggtttatt aagacacaga tatgtgttca ttctggggcc 58500
aagcagtaac tggagagtgg cacttattga ggccagtatg gaggcagtac agagattatt 58560
gagattaaaa gaaagaaaca ggtggaacgg atctatgtaa tggaaagcta aacagaatag 58620
ttcgtggtac acagtagaaa agcattacat gtttattaag atatggtcat cttccattta 58680
ttaaagttac atgttttata atttttagag tatatagaaa ttctctaccc tatcatgttt 58740
gccaaagtca gaacaataac ttcatttatt aaatataaaa aaaataaaaa cctctagcat 58800
aaaatagaat tttatttgga caaacgataa aaaaatactg tgtggtacta gtaagagtaa 58860
ggttgattca agatacatgg gagcagaatc caaagtgtag aaataggcca ggtgcagtgg 58920
ctcatgcctg taatttcaac acttttggag gctgaggcgg gaggatgagt tcaggagttc 58980
aagactcgcc ttggcaactt ggcaaaaccc catctctaca aaaagtacaa aaattagccg 59040
ggtgtggtgg tgtactcctg taaacccagc tacttggtgg gctgaggtga gaggttcact 59100
tgcagccagt aagtcaaggc tgcagtgagc tgtggttatg ccacggcact ccagctgggt 59160
gacaagcaag accttgtctc aaaaacaaac cagccaggcg tggcggatca cctgaggtaa 59220
ggagttggag accagcctgg ccgacatggc tctactaaaa atacaaaaat tagctgggcg 59280
aggtgacggg cacctgtaat cccagctact tgggaggctg aggcaggaga atcgcttgaa 59340
tccaggagac ggagtttgca atgagccgag atggtggtgc tgcactccag cctgggtgac 59400
agagccagac tctgtctcaa aaacaaaaat aagcatagga catggggata aattgaagat 59460
ttatgaagac acagctgaag gagacataaa agtagatttg gctaaatgga aacatgccat 59520
actttgaatg gaattattta atactacaac gttgtcaatt ttcctcaaat aaatctctaa 59580
agataatata ttcagttttg gccgggcacg ttggctcacg cctgtaatcc cagcactttg 59640
gaaggctgag gtgggccgat cacttgagga cgggagtttg agaccagcct ggccaacatg 59700
gtgaaaccct gtctctacta aaaatacaaa aatcatctgg acatggtggc aggtaccagc 59760
tacttgggaa gctgaggcag gagaattact cgaaccccgt aggtggaggt tgcagtgagc 59820
tgagattgca ctccagccgg gtgactccat ctcaaaaaaa aaaaaatttt tataatatat 59880
atatatatat ccgtttttgt agaaattgac aaaatgattc taaagcttat tagattatgt 59940
gtattaacag aagaactttg gaaatttttt tccacaagag tcataaagga ggacttgccc 60000
tacaaaatat gtcagaatta aaacataact tgtcagctgg gtgcggtggc tcacgcctat 60060
aattccagca ctttgggagg ctgaggcagg cagatcatga ccagcctgac caacatggag 60120
aaaccccgtc tctactaaaa atacaaaatt agccggtcat ggtggcgcat acctgtagtc 60180
ccagctactc gggaggctga ggcaggagaa tcgcttgaac tcgggaggtg gaggttgcag 60240
tgagccgaga tcgcgccatt gcactccagc ctgggcaaca agagtaaaac tctgtttcaa 60300
aaaaaaaaaa aaaaaaaaaa gaattataac tgtcacagtg gctacgtatg gagcatccaa 60360
aactgaattt atgtgggtat tttattaata tgcaatatag cactttaatt ctggaggaaa 60420

```
ggtggattat tcagtaaatg attctgggac attggggaca aattagatac ctacttcaca  60480
ctgataaata aaaccaaata gattaatgag aaaactgtga ttaaacaaaa caacacccag  60540
actacactgg agcaaatctg tgaatttgtt taattttgag tggagaagga ctttataagc  60600
atgactacca gagcaaaaaa atcatgaagt aaaagatcga tacctttgat tataaagaga  60660
ttaaagattt aggccgggtg tggtgctcac gcttgtaatc ccagcacttt gggaggccaa  60720
agcgggtgga tcacttgagg tcaggagttt gagaccaacc tggtcaacct ggtgaaaccc  60780
catctctact aaaaatacaa aaaaattagt caggcatggt agcacatgcc tgtaatccca  60840
gctactcagg aggctaaggc aggagaattg cttgaatttg ggaagtggag gttgcagtga  60900
gccgagattg tgccacatca ctccagcttg ggcgacagag tgactccatc tcaaaaaaaa  60960
aaaaaaaaaa gacttagacg tgtccaaaag taccatacat ttaaaaagac atgccacaaa  61020
ctgggaaaag tagaaaaata gttttaaaaa tgaccagtga atgtatgaaa aggtggccct  61080
cctcacttgt aatgatttaa gaaatgcagt ttatttttat tttattgtat ttttaaagaa  61140
attcagtttt aaagcagtgg aatatgattg tctatcagct tgcgctgaat ggtaaatgtg  61200
agaaagatta ctactactta gtggtactga gggagttgca aaacacttaa cactgctagt  61260
gggatggttt aagtaaaaca agtagcattc ttaaactctc tattaggtaa agaataggta  61320
agtaatgcat atgtttccag gacattttca gtaagactgt ttactgatag ggttgtgtaa  61380
tgctaatata cttactatct agttttagta ttattttttt ctcttgtctt ggatggtttc  61440
aatggagtct tatgcatgca gatatattaa aactagtaat aaagcaagag aaggaatgtg  61500
gataaattat ctctaatttc tattttgttc tatttctatt tcatactcct gggaaagaat  61560
attaagtggg catgtgtact tgaacagttg ttctgttttt tattagaaaa gaatccgaat  61620
ctataaaatg ttttacatat ttgccaggga aacagaaaag atatttgtac agctgtaaga  61680
attggaatta atttcatttt actgactttt ccttaaccta attctgaaca cttttgccat  61740
aggtttgaga ataagttgtt ataaaatgac tactattctt cactaatagt attggcattt  61800
caattcctaa attctgtttt ttgattcttg aacatttctg aatttacttt ttttgtctta  61860
gttcttctac agaatcattt tcttcttttt tcttttttta tttttatttt ttatttttga  61920
gacagagtct tgctctgttg cccaggctgg agtgcagtag cgcgatctcg gctcactgca  61980
agctccgcct cccgggttca tgccattttc tcctgcctca gcctcccggg tagctgggac  62040
tagaggtacc cgccacagcg cccggctaat tttttgtatt tttagtagag acggggtttc  62100
accgtgttag ccaaggtggt ctcaatctcc tgacctcgtg atccatccgc ctcggcctcc  62160
caaagtgctg ggattacagg catgagccat cgcacccggc cttctttttt tctttctctt  62220
taacttctga gctgaaaata gtacctttta taaagaagtg ctcaaacgat gattggactg  62280
atttctcctt atttctctct ttctctctgt ctctttcact ctctttttag aatttttctt  62340
ttttaagtag agacgaggtc ccactatgtt gcccaggctg tcttgaactc ctgagcccaa  62400
gcaatcctct ttgcctcagc ctcccaaagt gctcggatta caggcttaag ctatcacacc  62460
aggcctaggc taatttcata ttttgagatg gcacaaattt ctttcaggta gctagctttt  62520
cctcctcctc cccacttaaa atagatcctg atccagaagc ctaatggaga aaatgaaaac  62580
agaatgttca cccataaaca gtatctttgt attggaatct tttctaaaac ttcttttgat  62640
ctttttagga gatagtgtgg gaatcagcaa tctagtatta cgtacgtgga atctgtcacc  62700
ttgttttttt aaatacagca aacctcatga agtgaatttc catatttttt cttgttcttg  62760
```

```
ttagttttgc accactcagg ctttgctgta gaatttgatg tatatttgat tctgtagagc  62820
atgggctatt gatcttcact cagctttcag aggaatctga ttagtaagtt tgagtttttt  62880
attatttttt agttgatttt gaagtaaaat acagcaccat tttaactgat accatttcta  62940
aacaattttc agttcaaatt ttaagttagc taatttagag cttaagaaaa ttgctttaaa  63000
aacataaaat tactggctgg gtacagtggc tcattcctgt aatctcagca ctttgggagg  63060
ccaaggcaga tgaattgctt gagcccagta gttcaagacc agcctgggca atatggtgga  63120
accccgtttc tacaaaaaaa atacaaaaag tagccagaca cggtggtatg tacctgtagt  63180
cccagctatt cgggtggcag aggtgagagg atcatctgag cgcagggaga ttgaggctgc  63240
agtgagccaa gtgagaccct ggtttcaaaa aaaaaaaggt tactaattgc agtgcctttt  63300
atcttattta atgggcttag tcaaactaag atgatgtatt ttatcttata aatgttttcc  63360
cttgaatttt aactgaagaa tccaatttgt acctctcaca aacagaatgt attagtaagg  63420
aaaataaata ctgcttttta ttacttaaat aggatatatt tttctcttag ggattttttt  63480
tctattttat ctcactttat cgtagtgcta gaaaatttaa tcattcattt gagataggga  63540
gaaaattagg tttttttttt tcttctattt tgagacaggg tctcattttg ttgtccaggc  63600
tggagtgcag tggcgccatc gtagctcacc ataacctcaa actcatgggt tcaggtgatt  63660
caccttagcc tcctgattaa gctgggactg cagatgtgta tcaccactcc tggctaattt  63720
ttgttgttat tttttgtttg atgaggtctc attatgttgc ccaggctggt ctcaaactct  63780
gggcctcaaa tgatcctcct gccccagcct cccaaagtgc tgggattaca ggcatgaacc  63840
tctgctccca gcccattttt taaaatatat tcacagcatt gtgcaaccat cactacaatc  63900
aatttacatt ttcatcaccc tgaaaagaaa ctctgaaccc cttagcagtt cctctctgtt  63960
tgtttcaatt ttccccagct ccaggcaact attgatttat tgtcttcata ggtttgccca  64020
ttctggacat tgcgtattaa tggaatcata taatatatag cctttttttt tctttttttt  64080
ttttgaaaca gagtctcact gtgtcgccca ggctggagcg cagtggcatg attgcagctc  64140
actgcatcct ctgcctccca ggttgaagcg attctcctgc ctcagcctct tgagtagctg  64200
ggactatagg cgcctgccac cacacctact aattttatat ttttagtaaa gacggggttg  64260
caccatgttg gccaggctgg tctcgaattc ctgacctcaa gtgatctgcc cacctcggac  64320
tcccaaagtg ctgggattgc agccatgagc caccgcatct ggccatatat attatgatag  64380
gcttgtttca cttagtatgt ttcttccatg ctgtagcatg tattagtact tctttctttt  64440
tcatggccaa atattccatt atacagttac acaggtacac tacattttgt ttattcatca  64500
gttggtggac attttcattg tttccacctt ttgatttata cataatcctg ctgcgaacag  64560
tgacttttaa agtttttgtg tgggccgggt gtggtggctc atgcctctgt aatcccagca  64620
ctttgggagg ctggggctgg cagatcattt gaggccggga gttcgagacc agcctgccca  64680
acatggtgaa accctgtctc tactaaaaat acaaaaatga gctgggtgtg gtggcgtgca  64740
cctgtaatct cagctactag ggaggctgag gcagagaatc acttgaagct gggaagccga  64800
ggctacagtg agccgagatc acgccactgc actccagcct gggtgacaga gtgaaacttc  64860
atctcaaaaa aaaaaaaaaa aaaaaaaaac tgcgtgtgga cataggtttt caattctcat  64920
gggggtgtgt gtgtatgcat actcatacat acatacacat acctgcaaga taattgctgg  64980
ctcgtatgct aaatctatgt tgaacctttt acataactgt tgggctgttt tgttttcttt  65040
ttattatttt ttgaaaatag agttggggtc tcactgttgc acaggctgat ttcctgggca  65100
tagtggctgt atcattttac aatcctacat agctgtttcc aacgtagctg tatcatttta  65160
```

```
caatcctact agcagtgtct gaggtttctt atgtttttca catcctcacc agcatttgtt  65220
attgtctgtc tctttgatta tacccatcct agtgggagag taagaagtag tatctcactg  65280
tagatttttt ttttctgttt acaactttac tttaaaaatt atatatgcac acatggtaaa  65340
aagttcaaaa cgtgtgtacc aaaagattta acagtgaaaa tagaaaataa gtgtggtcct  65400
tgttttcttc caccaaggca aatattgtta taatctccta aacaacttgt cttccagatt  65460
tctcattttc agtcaatctt gggcattgac ataaagaaat tcttagacat tgcttttatt  65520
agatcatctc atcccttgct caaaatcttc agtggccact gttgtttaca gaataaagtt  65580
gggatgctat acagggccct tcccagtgga acttctcttt ttcaacctta tctctcatta  65640
tttcccaatg tttttttttt tttttttgag acggagtctc gctctgtcgc ccaggctgga  65700
gtgcagtggc gggatctcgg ctcactgcaa gctccgcctc ctgggttcac gccattctcc  65760
tgcctcagcc tcccaagtag ctgggactac aggcgcccgc cactacgccc ggctaatttt  65820
ttgtattttt agtagagacg gggtttcacc gttttagccg ggatggtctc gatctcctga  65880
cctcgtgatc cgcccacctc ggcctcccaa agtgctggga ttacaggcgt gagccaccgc  65940
gcccggccta tttcccaatg ttaatctact tattgaccta ctaagctggc atgttctgtg  66000
tgttagacat caccaacttt gtgccttctt tttttgtttg tttttgagtt ggagtctcac  66060
tctgttgccc aggttggagt gcagtggcgc gatcttggct caccacaacc tctgcctccc  66120
gggttccagt gattctcctg cctgagcctc ccgagaagct gagacgacag gcgcgcgcca  66180
ccatgccctg ctaacttttg tatttttagt agagatgggt ttcactgtgt ttcccaggct  66240
ggtctcgaac tcctgacctt gtgatccacc tgccttgggc tcccaaattg ctgggattac  66300
aggcgtgagc caccgcggcc ccctgtgcct tcttctttta ctcctggatt taatcccaac  66360
gtgaagaatc taccttacta actagagttt tagatacttt ttcaaaacca agcccacatc  66420
tgtccttttt agagtcttct ctgaccttcc ctgctcattg tggtttgttt ttattgcctg  66480
taacaatggc tgttaaactt tacattttaa attaatttat gtttgtatgt atttatttgt  66540
tgagaaaggg tctctctctg tcacccctac tagaatgcag tggcgccatc atggcttact  66600
gcttcctggg ctcaagctgt tctcccattt cagcctcccc atgcaccacc ctacctggct  66660
aatttttttg tttgtttttt ttagtttagt ttttgtagag acagatgtct cactgtgttg  66720
cacaggctga tcttgaactc ctgggctcac ttgatcctcc catctcagcc tccccaagtg  66780
ctgggattac aggtgtgagt caccatgccc agactttaac attttctttt tagtatagaa  66840
taggtcagtt tttttccctc tgatgagatc ccatgctgac tcttagttaa aacaaggctt  66900
tggttggaag aagagctagt gatgtcctag ctccctactt actccacttt cccttgcctt  66960
ctggggtgtc ctgaagacat catagggtgt catgaagtac agttggagaa ccagtggtct  67020
ccatcatgta ccaaacactc atcttcacga agcagtatgt agtgtctttt ttaccggtat  67080
attttctctc tcccaatgca ttaaactttt ctggagttca gaaaacaaat ttatagaatt  67140
aaggaaatgc gtcccccccca accatggtgt ctagtatata tacagtgact tacagataac  67200
aggtgttcaa catatatata ttcctttgat tgatttttga aaagtttaca tgtatatatt  67260
ttttatatac ggggtctcac tctatcactg aggttggagt gtggtgatgc agatcttggc  67320
tcaccgcaac ctcctcctcc caggctcaag tgattctccc acctcagcct cccgagtacc  67380
tgggaccaca ggtgcgcatc accatgcctg gctaattttt tatatttttg gtagagacag  67440
gattttgccg tgttgcccag gttggtttcg aactcctgag ctcaggcagt ccacctgcct  67500
```

```
tggcttccca agtgtgagcc accactgaaa tacttatatt tttaaactta atttatttat  67560
atttattata tttttatgtt tttatatttt aaaaaatatt tttatactca ctagacccaa  67620
ttttatactc ctaaaccagg gaataactgt tttttttct cttacatagg catgatacca  67680
tagacaatga ttaaaattgt aattaccatt catttcttag ttttgtggct gggacactga  67740
tgtcttcaaa tgttagtttg caaatacagt cagccctctc tatccatggg ttacacagct  67800
gtgaattcaa ccaaccatgg atccaaaata tatgggaaat acgctggggc tgtgggtcac  67860
acctgtaatt ccagcactta gggaggctga ggcagatgga tcacctgagg tcaggagttc  67920
aagaccagcc tggccaacat ggcaaaaccc tagctctact ataagtacaa aaaattagct  67980
ggccatggta gtgcacatgt gtaatcccag ctactcgaga ggttgagaca agcaatttgc  68040
ttgaacctga gaagtagagg tttccatgag ctgagattgt gtcactgcac tccagcctgc  68100
gcaacagagt gtgagaagaa aagaaaaaaa actgtctgaa aagaaaaaaa aaaattatat  68160
gggaaatcaa aagcatctat actgaacatg tacagacttt ttttcttgtc attattcctt  68220
aagcagtacc acaactattt ccgtagcatt tactttgtat taggtattat aggtaaccta  68280
gaggtttaaa gtatgcgaga gtatgcaaat actacaccac tttgtatcag ggacttaagc  68340
atccctggat tttggtatcc ctagggggta ttagaaccaa tcccccatag atgctgaagg  68400
acaactgtag tgtgtgttgg aataatttat tttcaaatgg atcatttgga gaacactatt  68460
ctttaggaaa catagcctcc taagttctgt tccatacatc cctttcacct ccacggcgtt  68520
gtagcatcct gctttcatga ctgtgtcatc actcggaagg aactgcttct cttccagaat  68580
gcttttcaag atctactctg accacagcta taaactttac acttctattc tcttcttgcc  68640
cctcacagtg ttctctgttc ctctaagatc ttaaactctg tctactccta atccagcctg  68700
ctgggtgtgg ctggagaaag tcccactggg gggctgatta gttaggaatg tagggtttcc  68760
agctcttgct ggagcctcag aagagttcag cagacttttt tttttttttt tttccttaaa  68820
cctatttctg cagccttgat gaccactcct tccagtccct cacctatttg ctttattcat  68880
ggcagaggct ctttcttcct gcttgtcagt acaaagaggc aggattcttc acctggatct  68940
gtggattctc aaagaatttg tggagagaat tcagggcatt gatgaccttg gatgaagaga  69000
aatttacatc tttatttaca ctaaccttca agtgaaattt agcatttttt gccatttaaa  69060
aatatgggca acaaacaact agtagtatta gcagtattta tgacttaagc acctatagaa  69120
ctcagttaat ttcatatcgc ttgatgttat gggtatctca aattattatt ttatgtatat  69180
atatttttga gatggagtct cgctctgtct cccaggctga gtgcagtggt gcagtctcag  69240
cccattgcaa cctctgcctc ctgggttcaa acgattctcc tgcctcagcc tcctgagtag  69300
ctgggattac aggcgcacac caccacgcct agctaatgtt tgtattttca gtagagaagg  69360
ggtttcacca tattggccag gctggtcacc aactcctgac ctcaagtgat ccgcctgcct  69420
tggcttccaa agtgctggga ttacaggtgt gagccaccgc acccggcctc aaattatttt  69480
tagaaacaga atcttgatat ggtatccgct ctggccttga acttgtgggc tcaggcagtc  69540
ctcccacctc agcctcctga gtagctggga ttataggcat gtgccactgc accaggcttc  69600
aaattattat gtatgttcat cacctcttta aatttataat agttattaaa cctgttactg  69660
gatcttaata tttaatgctt taattaagaa catgtatgtt actatgccaa cagatttttt  69720
tagtttttga taactgcatt tcattgttac ttgttctcat ttgatttcct gtgtatttta  69780
cgaatttaag tacattctga atacggtttc ataggcttcc ctaaaatatt gaaggggccc  69840
atggattaag aaaaaggcta agaatcccta atctagaggc tccccacagt cctcttttgt  69900
```

```
catcataccc ctaccccatt ctagcctgag gagcgtggct ccacctgtgc ccttggtttt  69960
gttgttccag tccatacatc ctgcaccctt aactgtgttt cttatcccca acttgtttct  70020
ttgtgttatt cttcagtatt atagtcttta atataatctg tataatacat ggtgtagtag  70080
tatatgctcg tagtatacaa ttcagttaga acagatgagt attcaatgaa aagataatct  70140
cctctctaac ccccagtccc acttccctgg ggaagcctgt gttcttgtgt acaattcaga  70200
aaatgtttat acacatattt tttatttatt tattttttga gacggagtct cgctctcgcc  70260
aggttggagt gcagtggcgc aatcttggct cactacaacc tccgcctccc tagtagttca  70320
agcaattcaa ggttcaagca attcgcctgc ctcagcctcc cgagtagctg ggactatagg  70380
cgtgtaccac cacgcctacc taatttttgt atttttagta gagacagggt ttcaccatgt  70440
tggccaggat ggtctcgatc tcttgacctc atgatccacc cgcctcagcc tcccaaagtg  70500
ctgggattac agatgtgagc cactgtgccc agcctgttga tttaatttta aacagagttt  70560
cgctcttgtt acccaggctg gagtgcaatg gtgcgatctc ggctcaccgc agcctctgcc  70620
tcccaggttc aagtgattct cctgcttcag cctcccgagc agctgggatt acaggcatgc  70680
accaccatgc acagctatat ttagtagaga tgggggtttc tccatgttgg tcaggctggt  70740
ctcgaactcc ggacctcagg tgatccgccc gcctcggcct cccaaagtga tgggattaca  70800
ggcgtcagcc actgcacccc gcctatacac atttttttgt tttttgtttt tttgagatgg  70860
agtctcgctc tgttgtccag gctggagtgc agtggcgcga tctctgctca ctgcaagctc  70920
tgcctccctg gttcacacca ttctcctgcc tcagcctccc gagtagctgg gattacaggc  70980
gccggccact acgcccatct aactttttgt atttttagta gagatggggt ttcaccgtgt  71040
taaccaggat ggtcttgatc tcctgacctc gtgatctgcc tgactgggcc tcccaaaatg  71100
ctgagattac aggcgtgagc caccgctccc agctatacac gtatttttaa tgccactcca  71160
gtctatgttg gaaccatttt acttcccctt tcttatttc ttcttgtgtt cttgaaggcc  71220
tagatcagct gttgctgata ggctgtcact gtcactttag aaagcccaga gccttttgtt  71280
ccttagaact ttgtttttaa ttgtattgta gcactcattg tattcgattc taaaagattt  71340
gcttcatttc tgtaactagt ctcttacacc caggagctcc tagttcctac aggaaatgct  71400
gggaattgta tcagtcaaat gtgaatcccc acctcgtcca gacttatgag tgcattgtag  71460
gtactcagta agtgctaaaa atgactaaat agtcccactg ataccaatct atatactgat  71520
actttatata gtatatagat tggtccacat ataacgatga cacataatga gaaactgtct  71580
taaaaagttg ttgaaagtgc cgcaggaata ggaattgatc aaaacaatat gattttttag  71640
gtttatatgg aactttgatg tttgagaaaa ggctgattta gttgagaaga aatggttagc  71700
tgaggatttt gatgacttct ctggaagcac atttgagggt ttgtgatgtt aaatctgatg  71760
ttaatgatta tttcatccag ttttatgtca ttttatagtt tttatacatt taagtatatt  71820
tatttctaat gtttaacact accattttag ttatttgacc attattctgg ccctttaaaa  71880
aatgctcaga caagtttgaa tgatttttca gaggcattat tggctcagag gtaaaagagg  71940
aaagattgag aagctgaata tgtactctgt ttcctgggta tggggctggg gatacccaga  72000
agaggttcac acgttggtcg agacatttct ttatgaccac cagcaggtgg catcaccggc  72060
ccaaaatgac taagtttctg cccagaatca gaagagaagg tgttgagagc ccactgctgt  72120
gggggtagca tggaggtggg atacaggggc tggaggtgat acaattttgt ttcttcctcc  72180
aacatcgcct gctagtctag aggcttttat aaattgaaaa actaattctt tatcatctca  72240
```

```
tctgatggtt tttatgtttt tcctttttttc tctctatacc tgtagttcct tcagaaacag  72300
gtaacacttt tctaatagtc acgttgtatt cttgcatctt gttgttacaa tgcttttgtt  72360
tctcaccata ggggatgatg gaaaattaat attctttgac ttatggcatt ggtaaaatct  72420
gcatgcaaat tcccacagtt gcctgtagat tagagccagt tgtttttttc tcaactttgc  72480
aggaatcctg gttacaacat tgtactattt actaccaaca gtgttttttt tttttaaaat  72540
ccagacttgc tgggcatagt ggctcatgcc tgtaatctca gcgacttggg aggctgaggt  72600
gggaggattg cttgagccca gggctgcagt gattgcggca ctacactcca gcatgagtga  72660
caaagacccc atctctgaaa aaacaaaaac aaaaacaaat ttttttttaaa gaaacagaaa  72720
caaaaatcca aacttgtaac cactgtaaaa caaatcagaa tttacgatag tggatattat  72780
taatagtgca gaatggatac ccagatcttg cttcctttct agctaatgat gcaatgttgg  72840
cctgaaatgc attacttata gccagggatt ttctcagcat cctgatgata tagcctcatt  72900
tcgtgctaac tctccacttc tgcacatctt cccctaagtc ctttactcat ctttagaaag  72960
agctactttt ggtgaaattt taaaaccaag gaatatcatt ctttatagaa tcacacttct  73020
gtgttttccc cttccccatt tctgtctcga aagcgacaga ctgctacata acctgtgaat  73080
acttttttttt aaaaaaagtt tggtattgta aacagaagat ttaagattaa aatgtagcat  73140
tgagaaaaat agatttatta ataatgccct cttaacacaa cctaaattct ggtcagtgga  73200
ataaagcctg ggtcctaaag ttttagacgc ttgcttgctt ttccacactg gctcttactt  73260
ggggatcctt ttagaaattt gtttagaata atactgtaaa aacatattta agctactttg  73320
tgtgtacatt tgggatcttt tggtttgaag acggcttgac tcaagacttt ctaaatattt  73380
tcacacacac acacataccc tgtagtgaga aaaaaatccg tttatatggt tctataaaaa  73440
tctctagctg cttcgagctt taatttcttg aatcaaaaga gtattgtttt taatactgag  73500
cttctatcta aataaatgct ttatttactt aaatgtgtgc ttttcaaaaa ctagtatgat  73560
taagacatta acaggatctt agacgtaaag gaacagtcct gttgcttctt ccagaagata  73620
atatgactcg tttggaattt tcctatagtg tagttttttg tctagtgttg tgagaattaa  73680
agggatttca ggatcttaag gtaggttatt atttgatgtt ttcttggaac attttacatt  73740
cttgaaaata cacatggcta aattaatttt tgccagcaat ccacataact ttaagataat  73800
gtagagaaga acgtgattca ggttagtatc aaataaggtc agatttctag tgccatcagt  73860
agctttcagc aaagatgagg tgttggtaag atagcattag tctcttagaa tctcttagag  73920
agattttcca aaattcagcc atttctagtg aatgctccat tccaccccca gctgagtcct  73980
gctgctctgg ggaactccct cagcacactc ttggctctta gaattgctag caatgggagt  74040
agtgctgctg gtggagctgg cagctaagcc cagaggtgga ttaatgcttt tattccctga  74100
tgtacaggta cacacactca tacctaccca cacctagttt gggataagaa gaggttagaa  74160
ttagctaggc ttgaagttcc atgcttaaat ttgctggctc agatttctta ttttggcatc  74220
actttgccca ttagggagac aatgacagtt atagaagcat tgccaaataa aaaatccatc  74280
tggaataacc tcttttgtag gagtattgtg tgtttagttg ttgattcgtc ccttcctcct  74340
cttagtggca acttacagta ctgggaagga acagtggctg ggagcttata ttcctcagca  74400
gagccagatc agcagaagta ttactcctta gttcgtagta ggtggtaccc tatgggtcca  74460
gtcatttaaa tgcaagcctg tatctacaga gcgtttccta gtgccatcat tgcccagtgg  74520
gcctttattt agctgagtct aactcccaac tagagaaaat ttcctgtgcc agacagcagt  74580
atggtcagct aacatgtgga tgctacattt gctttcataa gtcagtactc ttcaataaca  74640
```

```
ttagtagaag agaagaggac acaaagtgag agtgtgttaa taggaagtcc aggtatgcct  74700
gctacctgaa ctttctgaga caggtaatac tgtagggcct gaactttgta gcagagtggt  74760
tatatatgaa gaagtgggtt ctgggagggg ttaaaccact tagaatggct tcatttacta  74820
atggcaagag tttgctggga tattgaccac tgtacataga catgaatatg gaaagttaaa  74880
aacaaaatcc acatatattt ggctgcaagt actccgaagg tatatctaat tagtgcatcc  74940
attaaacaaa agagatattt taggccgggc atggttgctc acacctgtaa tcccagcact  75000
ttgggaggcc aaggtgggtg gatcacctga ggtcaggagt tcgagaccag cctggccaac  75060
atggtgaaac cctgtctctg ctaaaaatac aaacattagc tgggcgtgtt ggtgggcgcc  75120
tgtaatctta gctacttggg aggctgaggc aggagattcc cttgaacctg gaaggtggat  75180
gttgcaggga gccgagatgg tgtcactgca ctccggtctg ggtgaaagag caagctccat  75240
ctcaaaaaag aaaaaaaaaa aaagagatat ttttgatgga ttgatagaaa ttttcttttt  75300
cttttttttt ttgagacagg gtctcactct gtcgccaggc tggagcacag tggcgtgatc  75360
tccattcatt gcaacctcca cctcccgggt tcaaacgatt ctccttcctc agcctcccga  75420
gtagctggga ctacaggcat gtgccaccat gcccaactaa tttttgtatt tttagtagag  75480
agagggtttc accatgttgg ccaggatggt ctcgatctct taacctcatg atccacctgc  75540
ctgggcctcc caaagtgctg gtattacagg catgagccac cacatctggc cagaaatttt  75600
cttggtcact tctgagacat gcagagtaat tacctgtaat ataatttaat gaattatgtc  75660
aatatattaa aatatgcttc atgtgggctg ggcatggtgg ctcatgcctg taatcccagc  75720
actttgggag gccaaggtgg gggtatcact aggtcaggag atcaagacca gcctggctaa  75780
cacggtgaaa ccccgtctac taaaaataca aaaaattatc cgggcgtggt ggtacacacc  75840
tgtagtccca gctactcggg agactgaggc aggagaatcg cttgaacccg ggaggcagag  75900
gttgcagtga gccgagatca cgccactgca ttccagcctg ggcaacagaa cgagactcta  75960
tctcaaaaaa aaaaaaaaaa tgcttcgtgt ggcttaaaat tatatgaaaa gaaaatacct  76020
ttactgatag tcatctgtga ttccatttgc taaattaaac gtgaaagcat acttttactg  76080
aatactatat attccgtatc agtttagata gcagtttatc ttcacataca taagttttaa  76140
gtttaccttt attatagtgc attggtcttt tgttttcatc aacctaaatt atgttcaata  76200
aatgtttctg ttagatttta agttaaacaa ttatgtgaaa ttcatttttc gtaattgttt  76260
tttaacatat gtctttgttg gtaattcacg tgtgtgagtg taactgattg ccagattata  76320
taaactttca accaaaacca ttctttgcag atgcttttac tgactctgct atcagtgcta  76380
aagtgaatgg cgaacacaaa gagaaggacc tggagccctg ggatgcaggt gaactcacag  76440
ccaatgagga acttgaggct ttggaaaatg acgtagtaag taacatcttt gtaattattg  76500
ctagactctg gtcagtatga catcctgtca cttggttgta atttaaatgt gcttttgttg  76560
ttgttgttat tgtagtgagt gtatttagag cagcaggttt gttgtataac tagagacttt  76620
ctcccaagca atatataaag aaaaatgttt gtcattttac ttgtaggggt taagcaggag  76680
tactgtctgt tcttgtggat gctcatgaat tacttctttg tgattaaaat aaataataag  76740
aagtagctta aattaaaatt agaaaccatg ggaaatgccg gtgtgttttg ctttaacacc  76800
cagccaaata aggtagccta aggaaagtgg tgtcttaatt gttgacttca cctagagaag  76860
aggttgaagt aggacatttt aagcctcttg tctgaagaaa aggttgtcat taagataaat  76920
aattaggtta cattggaatt aaagcattac ataaatttct tggtcttaaa tttggattat  76980
```

```
tctccacaaa attcttttat ttctaaaacg cctcttgtca catactagtt ttgtttctct  77040
ctttaatgca ttatctgtac ttgaagtgct tagctgggta tgctggcaca tgcctgcagt  77100
cccagctact tgggaggctg aagcaggagg atcacttgag cccaggagtt ggagtccagc  77160
ctgaatgaca taaggagacc ccttctctaa gaaataaaaa taaaaacaaa tacttaataa  77220
agactctgtc tttaggatag agagcataga gatataaagc aaagtgtctt gccaaaaatg  77280
agtgttatgg taccaatatt tgagtagaat gaagaatctt ccattgagta gaaagagaat  77340
ttgtaacata tctgtgtttg atgtttaagg cataacagct taataatgac actcttcctc  77400
agacaggaag cctgaaatgt cctactttga cctaaagtct agtaataaaa ctggacatac  77460
acaggcaaca tgtcattaat tctcaaactt taacaaatca tatataacct aatataatgg  77520
ttctcaagtc tgtacatcac gtcacctgta tgaaaaatat gaggaaacag agacttcttt  77580
tacactattg gtgaggtgga taaattgata gagtctttct ggagagaatc tggcaatgct  77640
aatcaaaatt taaaatgcac atacactttg ttccagcagt tctatctcta gtaatttatt  77700
tttgccctca tatatccata agacatgcaa ataattatat gtgaagattt ttttttttc  77760
tttttctgca gagacagggt tttaccatgt tgcccagggt gatctggaac tcctgagctc  77820
aggtaatcca cccacctcag cctcccaaag tgctgggatt acaggtgtga gccatcatgc  77880
ctgaccagga tttttttttt tttcagcatt atttcttttg ttgttgttgc tgttgttttg  77940
agagatggag tctcactctg tcacccagac tggagtgcag tggtgcgatc tcggctccct  78000
gtaacctcca cctcctgggt tcaagtgatt ctactgcctc agctttccaa gcagctggga  78060
ctataggcgt gcgccaccac acccagctaa tttttgtatt tttagtagag acggggtttc  78120
accatatgtt ggccaggctg gtcttgaact cctgacctca ggtgatctgc ccacctcggc  78180
ctcccaaagt gctgagatta taggcgtgaa ccaccatgcc tggccatagc attatttcta  78240
atagtgaaaa attggaaaca tgctaagtgt ctatcaatat agcatgagtt agatttatga  78300
tgtcaccatt caattgaaac actacatatc tcccaaaaag aatggtgttc caatatggaa  78360
agatatctaa gatttattaa gagaaaaagc acattgcaga acactgggat cctatttgct  78420
ttttttttc tttttttgag acagagtctt gctctgtcac actgcaacct ccgcctcccg  78480
ggttcaagcg attctcctgc ctcagcctcc tgagtagctg ccaccatgcc cagctaattt  78540
ttgtgttttt agtagagaag gggtttcacc atgtttgtca ggctggtctt gaactcctga  78600
actcgtgatc cacctgcctc agcctcccaa agtgctgcga ttactggcat gagccaccgc  78660
acctggccat gaaatttttt tttttttta aagagctgtt catattctta ttgcctagaa  78720
gatgtctgaa attacaccca agaaactctt tttgagacgg agtcttgctc tgttgtccag  78780
gctggagtgc aatggcgtga tcttggctca ctgaaacctc tgccttccag gttcaagcga  78840
ttctcctgct tcagccttct gagtagctgg gactacaagc gcccgccacc acatctggct  78900
aattttttgt atttttagta gagacagggt ttcaacatgt tggccaggct ggtcccgaac  78960
tcctaatctc aggtgatcca cccaccttgg cctctcaaag tgctgggatt acaggcatga  79020
gccactgcgc ccggctgaaa ctcttttttt ttcttttaag atggagtctc gctctgtcgc  79080
ccagacttga gtgcagtggt gtgatctcag ctcactgcaa gctctgcctc ccgggttcac  79140
accattctcc tgccctagcc tcccaagtag ctgggactac aggctcccgc caccacacct  79200
ggctaatttt ttgtattttt agtagagaca gggtttcacc atgttagcca gcatggtctc  79260
aatctcctga cttcgtgatc ctcctgcctc ggcctcccaa agtgctggga taccaggcat  79320
gagccaccgt gcccggccag aactcttaat agtagttatt tatgcacgct gggattggaa  79380
```

gacatttact ttttactgga tgtctttccg tattgtgtgc tttttttttt ttttttttat 79440
gtagggcata cattacttaa gtaattttaa agcctccata agtaagtgtg atttcctgcc 79500
catgtgtttg gcaaaaggaa ttgcattggt ggtagactta cattatagtc ttacctggag 79560
tagcacagga ggacccaagg ttaataggtg aacttcgagg caagccttag cattgaggtt 79620
gccatcagca ttgcttggtt gatgtgttca ttcttctggg atggattaca acctttactg 79680
gactttatac ttttcaccag taaggcttta aaaaaggagt tgaaacatta gagaataatt 79740
atccaggcag taatattcac tggtaaatag tcttccagcc tgtggcccaa ttggttgatt 79800
cttttacgtt aaagaatgca gcctcagctg ctctgcctat ggagtaggat tcttttattt 79860
actttcttaa taaacttgct tgcccctggc tcccccccac caaaaaaaga aggcagcctc 79920
ccttttgcga atggtaattt cctatagttt cctcgtagaa ttgtggagtt acctatgctg 79980
aggttatagg ttagggtatt gagatccaga gttgccactt ctgaggtgtc acaactgcta 80040
atggtaaaac catttctaaa gcccagttct tgtgactttg tccagtgatt gcctgttcac 80100
cgtttcatgc tgccttccca tttgagcatt cccaggagga aggggaggtt gccagggacc 80160
tagtaccata gtccgacctt ggaatcgttg aatatgaggg aaagcgttgg cttctccctt 80220
ctttctccca aacattggaa gtatttttgg ctgttaaaaa gcaccccttg ttccatgtgg 80280
aatcccttgt ttaaaagaag taaaatatgt acctcctgtc ctccacagac ctgaggacca 80340
gtgtgatctc aagaaggtta caggtaaatg tagatgtctc taactgaaag gtggctttta 80400
caggttagag aaaagagaga accctgatct gaaggctatt ttatgaagta attaaaatgt 80460
tctaaacttt aaaaataact gctcaaataa ttgtgttgta tagttactta tcaactggag 80520
gggctgataa gtatttttct aaaacatttt taaggaaatt ttttcctatt ttctaatttg 80580
ctaattttgc tcaagtagtt tgttagatat tgttaatata gatgttggtt ataactgaat 80640
gaaagggaac aactactttg acattttgaa aaacaagctt cattttcttc tagtctaatg 80700
gatgggatcc caatgatatg tttcgatata atgaagaaaa ttatggtgta gtgtctacgt 80760
atgatagcag tttatcttcg tatacgtaag tttgaaaagt ttgtttttat tttagtgcat 80820
ttgtctttga ttttcatcag cttaatttat gatgaataaa tgtttgttag tttttaagtt 80880
aaacaattac atgaaataat ttttctctta ttaccaactg tgataaattt ccattaaaaa 80940
aagggaataa atgtagtttg cctataccct gtttttatgc tctaaacaaa ttttggtttt 81000
gtcttttttt ttcttttgag agggaatctc gctgtgtctc caggctggag tgcagtggtg 81060
caatctcggc tcactgcaac ctctgcatcc cgggttcaag cgattctcct gcctcagcct 81120
cccgagtagc tgggactata ggcgcgtgct accatgccca tctaatttct gtatttttag 81180
tagagacggg gtttcaccat gttggccagg atagtctcga tctcttcacc tcgtgatcca 81240
cctgcctcgg cctcccaaag tgctgggatt acaggtgtga gccactgtgc ctggccggtt 81300
ttgtcttcta agttgttaaa aaatatctaa atttgcaagg gcagagatta tggtgaacag 81360
tttaaccagt ttttgaaata tgttcctctg gagaaaaggt aacagaaaaa aaagttagaa 81420
ttttgattta taaatacaca gatcactata acttttagtt ttagttttag ttttagtttc 81480
tgtttttacc agtattctaa actctaaact ttcttagtag ttgattatga cagatacata 81540
aactgtggct ttaaaggact cattttgctt ttcttttcct catgtttcag agtgccctta 81600
gaaagagata actcagaaga atttttaaaa cgggaagcaa gggcaaacca gttagcagaa 81660
gaaattgagt caagtgccca gtacaaagct cgagtggccc tggaaaatga tgataggagt 81720

```
gaggaagaaa aatacacagc agttcagaga aattccagtg aacgtgaggg gcacagcata  81780
aacactaggt atttaaagga aatcatgatg cagtattttg gatacacaac tcaaggtctg  81840
tgtgagacgg tgtattgtta ttatatttcc tcttccttta atatagctta ggtagagaat  81900
gcaagtagaa ttggtttaag atctgttaga gaaaaggtta tggtgatctt ggaaaatatg  81960
cttttgagag taagctctgt ggagccaagt gttggtatat cacggtgagc aatccaagat  82020
cttgaagagc ttgttaaaat agttatctgg tgggggacac gtgtaacaat cacagcagta  82080
caatatgatt tgcttggtta aaggcatgtt caaagtacta ggaacataca gaatgaggag  82140
gagctagcat aacctgtaga gtcagagaaa acctcattga ggaggtgaca ttttgtgata  82200
agataatagg gtctttgaca cttagagaag agttgggaga agagtttatc acctgatgaa  82260
aagccatgta caagcatggc tatgagaaaa tttggccagc tcaggagagg gctggttgtt  82320
gcatgtgtct ggaacacagg atctgtgtca ggtgcagcag tggcagttga tagtaggaac  82380
tgaggtcatt aaaggacttg gcatgtcatg ctaaagagca ccctgttgga aggagatggg  82440
gtgaataaac cctggggcat tgaggactgg ctgagacaca gagaacagtt agtgcactga  82500
aatagttcaa ctgtgagaat ttggtaacca cctagttaag ggatgagcct gaggtttatt  82560
tgataactaa gtgacttaat ggatgtactg gtaagagaga gaggaaacat ggagcaagtt  82620
tgaggggaaa aacagtgact ccgtttgtgc agctaattgc atatgtgggc ttgtgggtct  82680
ttcatttatt cataaacgtg ttgagaaata cctgctacct atctagtaaa gtaagagatg  82740
catcctctct taaaggcagt cagcttagag tctggtgatt tgaattgaca tgtccactga  82800
tagatgttga cactgtgaga ctggcggttc agtttgaggt ttcatcagca ttgccgatat  82860
tggagccatg aaaaaccaaa gaacagccag tgagagaaga gatctcagag aaaataaaat  82920
tgagaaagtg aaggacaaaa aatgttgtga agatagacca agattgatgg aatcagccat  82980
agagaggtca agtgggatga gaatgagcac gcatctgtta aactttgtgc ttaggagcag  83040
aatctaaggg aagggacagt ccagaggtta gaactcaggg taagatggaa gaacaggggc  83100
atctgggagt gaggcagttt ggtttagtgt agaacctttt tgtaacaagc attcccttct  83160
gtctagatga cttttagata tgtttcattg gcttggtacc ttttagaata aaatgattta  83220
gaggatctct cattttcagg gaaaataaat atattcctcc tggacaaaga aatagagaag  83280
tcatatcctg gggaagtggg agacagaatt caccgcgtat gggccagcct ggatcgggct  83340
ccatgccatc aagatccact tctcacactt cagatttcaa cccgaattct ggttcagacc  83400
aaagagtagt taatggaggc aagtattttg accagacttg tcaatatcat tgataaaata  83460
gttttctaaa tacttaaaat acttaaaata gtttacataa ctgatatgaa tgtgcacttt  83520
aatgatttgg tgagtagctt tcacttcagc attacttaaa attggctttt gtggatatta  83580
aattagtaaa acattgtata tgtcattgac atatatatta tttagcatga tgaaatattc  83640
atgatgtact aagataaagt gctacattta acccaagaca atcacttggc caaaaacact  83700
tcacatataa agaaattgga aactttgggt aggttctcaa ttttaaaaac actggataat  83760
aaaatttttt agacataatt tatatggaaa attctaacct atgtgcaaca ctgtggttaa  83820
tatagatcaa ttttcattat ttgtttctat attatgctta cttcaagaaa ggatctgagg  83880
taacttataa tacaagacat gatcaagagt catgtgaaga aagtgactag agaaatttgc  83940
ttaaaaaaca acaaaaacaa cccttagtct aagggtggat gttacagttt agcaacttaa  84000
gtaaaagaaa cctgaatctt tagtaggaag acatttttta ctctacctct aaatctaggt  84060
tgaatatatc ttgtaggttg tggatctttt ccataaatca gggatactga acaacagttc  84120
```

```
tatggatggt atggaaatag taatagcaat agtatgttac taactttgtg ggaaaagagt  84180
ggacattcaa ttttagctat ttaaatttgg aaagttagat gaaaatagag aacactaagt  84240
ttccaatttc atttgttttc attgagtctt ttctccagaa ttcctctcca aatggacact  84300
cttgagtatt ttcagtactt aatattgggg gtgaaatttc tttgctcact gaggaaagat  84360
tttagttgtt tataaacaga attttaaagt taaaaaacct gaagggggct gagaaatata  84420
tgatacttaa gtgtgtggaa ccctatggag aggagacctg gactgtttga taagattaag  84480
gtaagtgata tgtaatgtta aatactagct gtatctttac ctaggcatat ccatcagtat  84540
aaatttattt ggtgatgact gctttgtagt tgcagtattt attaagcagt cgcttagata  84600
agtgtttaac tgtataaatt atttagaagg tctccctttt tctagtttaa tgaggtcaag  84660
actttttttt tgaaatagca atgaatatta tcatttgata ctcacaggag tcacaaactc  84720
tagaagagta atgttttatt tctacttaaa tgggacttgc ttaataagat tccaaactga  84780
gttctgggtt caagtgtaaa cctgatgaaa atcatagata attgtaagga accagcattt  84840
ctaattggat ataatagcta ctgcttattt tcgttatgcc tcagagttaa aactaataca  84900
gtaaataatc ttactcctga gtaggaatta ttgtgattta ttatgtgaaa ttatctagtg  84960
tatgttatat tcctttaaac aaccagttac tgagaaacag ttatagaagc aggattaata  85020
ggcaaagtct taactgtctt cttcaatagt gtgtatagat cctaattaac cctttgggaa  85080
cgtgtattca tttaaacaga cttaatctta aggaggttaa agtaaaatgt gaatttatgt  85140
cagttaagtt atgctaaaac ttatcacaaa tcaaatgact gtcctcaaag ggttaaaatg  85200
tacaagaaat catttttgtc attttacttt ttttctgttt actttttttcc ctcatttttt  85260
tctttagttt ttatactttc cttcatatca tttgttctgt caggtgttcc ctggccatcg  85320
ccttgcccat ctccttcctc tcgcccacct tctcgctacc agtcaggtcc caactctctt  85380
ccacctcggg cagccacccc tacacggccg ccctccaggc ccccctcgcg gccatccaga  85440
cccccgtctc acccctctgc tcatggttct ccagctcctg tctctactat gcctaaacgc  85500
atgtcttcag aaggtacaat accacaattt gttcatgttt ttgtttgtct ttgtttaact  85560
cctatgtgag tttataatta caaaatagtt tcctcttcat tatttaataa cctataattt  85620
ctgtgtttta actttagttt attaaaacta tttctattaa ccttttgttc attagagaga  85680
aatttgataa atgtgtgaag ctataaactc tcttgaattg ttgttaaaaa gggggtttat  85740
ctctgcctga taattatgct tctttacagc cccagaaggg tctgccccac agccttcccc  85800
ctccttattt gcactgtata cagtagttaa acaaatgaac tttcttcagc cagtcttgaa  85860
cttaggttca ttttacagct ctttggccaa ggtcctagtg aaccttccta ttggccataa  85920
gcagggatgg tgttttctgg gtcttttttg agagcgacag cccatgtagc tgactttgcg  85980
tgtctgccct tagattaaag tagttgattt ttagaatgcc agaagaattc taaatttaac  86040
tgagtaattt ttttaaagtt agctttgcaa tcttacatag tgaaaggctg ctttaatctg  86100
gaagaagtcc ttgatctgag ataaaattga taaaaacgac atatgaattt gaatatttag  86160
ctatttcttt cctcgtcaaa aataagaata aaatcttgta attcttattc agtatttggc  86220
gctaaatcca tcattgccac atatcaaata cagggatatg ttgtagaaag gtaacattct  86280
aatttaaatg ccacccatat attaaaaacc tgttttctga atcataatgt ccttttgata  86340
ctagttctga atatttgtgt taaaatttta atctgatttg ttcattaaaa ttagttaata  86400
ttgcttatgt tgggactaat aaagttttcc gcacaaaatg tgtttctcct gcttccctgg  86460
```

agaaaactgt attggctact tttaaataaa ttgttaccat ctaagcaggc aggtcatatg 86520
actttgactg aagcatctaa ccttgaagag caagttccac tgattttcaa ggtgacttct 86580
ttgctcaaaa gggccttaat agtggtcact aaatgcaaaa ttctgttgat atttttcttg 86640
tagtccatca tttgagtaag cgatgtttat ttaatgagaa tatattaaat aaaacatgat 86700
cattaatgac tgtgaacatc tttattacat taagatttaa ggactgctca tgtattaact 86760
tcacacagaa atatactttc tgtgtcattc agagatgttg aatatttcca tttgaaaatt 86820
atagtgtata acattagcat tcttctaaag atcatgttcg tgtttaaatt cctgttggaa 86880
gccaggcatg gtggctaacg cctgtaatct cagcactttg ggaggctgag gcaggtggat 86940
cacttgaggt caggagtttg agaccagcct ggccaacatg gtgaaacctc gtctctacta 87000
aaaataccca gctacttggg aggctgaggc aggagaatca cttgaacctg ggaggcagag 87060
gttgcagtga gttgagatcg taccactgca ctccagcctg ggcgacagag acagactctg 87120
tcttataaaa ataaaaataa aataataatt ctattggcaa catatattaa tttgaagttc 87180
taaagagttt ggcagccggg tgagagagtg aggagatttg gctttgacat tagggaagtt 87240
ttcgcttggt gttaacacca gtaggcttct ctgatgaggg ccattctgtc cactctttta 87300
cctgatagat tggtctaatg cacagtagac tgatttagaa agagtagtca ctagtggcat 87360
ggcagaatca ataatgtaga attttgacaa ttcatatagt gctgatttct cccccaaatg 87420
tcagttattt tggtcatcta ttaatagact aatacaagtc atccctttaa tagaattttc 87480
agctcacagc ctgctaagcc taagaaactg cttacaggtt actgcttact gttttaagcc 87540
gagttttaaa attgatgatc atgatagaag agataaataa actaaaattt tagagaaatt 87600
taagaagggt atgtacatat gttttagtgg tatcggggtg tatagggatt aatagtcttc 87660
tgtttaaatt tttttttct aattttagaa gtaatgtaga aaattcgggt cagggaaagg 87720
taaaatatat ggaaagttaa aaatatttta tcatgtagtc ataatttcta gtaacatatt 87780
tctttacaaa taagacatag ttgaaacaga ttgctacagt tcttttaaga gttgacatct 87840
tattgttgat ttcttaccac caacttcatc cctccctttc tttaaaaata aagggaaata 87900
ataaaattta tttataaaac tttgtggcat tccacaaaat aattctgaaa gaattagtat 87960
ggccaaaaaa atatgtatgg tgtttttttt ttttctattt ttaaccaagg aaaaactgta 88020
gagtgagtga gtgtgtgtgc atgtgtgtgt gaatgggtgt atttagcaga aaagtagtac 88080
tgatgaatat catggaattt atgtgatgtt cactgtttct tccttagggc ctccaaggat 88140
gtccccaaag gcccagcgac atcctcgaaa tcacagagtt tctgctggga ggggttccat 88200
atccagtggc ctagaatttg tatcccacaa cccacccagt gaagcagcta ctcctccagt 88260
agcaaggacc agtccctcgg ggggaacgtg gtcatcagtg gtcagtgggg gtaggtaaca 88320
cttgggcata atgatggtac tcattttgtc attacactag atataaagag ggctgagcta 88380
caactctgtt tgaggaagtg taagtatgta tatgttaaaa atagtagaat caccaggaat 88440
tgggaaaccc atatttttat tctgggctct accacttatt catcatatat taaagcaagt 88500
cagacactca ttctgaagtt gagatttcgc agtgagtaaa gtgttaataa ttcttgccta 88560
gtctacatta tgggattgtg atgagattcc tataaggttc ataaatacag atatattgta 88620
aaactataaa gttttgtaaa gtacctctct aatatgaggc aaacacagta tgtaacacta 88680
tttggaggga ccgtatttcc ttatcttttt agcagctttg tttatcagta cattctataa 88740
acatttattt ttggcttaca ttgtagtgtg tttctatagc atctgtatat ggcactaatt 88800
cccaactata tttccataat aaggaatatc aaatacaaat aaagggtcca agttttattt 88860

```
gtgattagca taaggaatat gctgacagca gctataaaag tataaaaatt aggctgggtg  88920
tggtggctca cgcctgtaat cccagcactt tgggaggctg aggtgggcgg atcacaaggt  88980
caggagatcg agaccatcct ggctaacacg gtgaaacccc gtccctacta aaagtacaaa  89040
aaaaattagc cgggcatggt ggcgggtgcc tgtagtccca gctacttggg aggctgaggc  89100
aggagaatgg catgaactcg ggaagcggag cttgcagtta gctgagatca cgccattgca  89160
ctccagcatg ggcaacagag caagactctg tctcaaaaaa aaaaaaaaaa aaaaagttta  89220
aaaactagac gttgacatga ttttacaata aggctgactg cttttgctac tttgccaatc  89280
agtccttagt gctttgttcc cataactgtg gtaagcaaga gcttacaaag aatacttaaa  89340
acaaacaaac aaacaaacaa aaaaaacact ttttctcttt taatcagtcc agagaacctt  89400
taaaagaaac aagatcggcc agttgctgtg gctcatgcct gtaatcccag cactttggga  89460
ggctgaggtg ggtggatcac ttgaggtcag gagttcaaga ctggcctgac caacatgatg  89520
aaaccccatc tctactaaaa atacaaaatt agctgagtgt ggtggctatt tgagaggctg  89580
aggcaggaga atcatttgaa cccaggaggt gaaggttgca gtgagccaag atcacaccat  89640
tgcactccag tctgggtgac aagagcgaaa ctctatctca aaaaaaagaa aaaagaaaca  89700
agatcttcaa gcttaaggaa acaaaaacaa aactcagctg tgttaaatct gtttttagtt  89760
gctatacatt tctgctcagc ttcatgtgat gcacattcat gtaattgtat cctaaattcc  89820
tttgtacttt ttattttctt ccttggtctt caattatctt aagactacca agaaaacaaa  89880
aattttaaaa atcttcttca gccggtcagg cgcagtggct cacggctgta atcccagcac  89940
ttggggaggc tgaggcgggt ggatcacgag gtcaggagtt caacaccagc ctggccaaca  90000
tggtgaaacg tcgtctctac taaaaataca aaaattagct gggcattgtg gcgcgttctt  90060
gtaatcccag ctgctcagga ggctgaggca ggagaattgc ttgaaccagg acccgggagg  90120
tgtaggttgc ggtgagcgga gatcgcgcca ctgcactcca gcctgggcta tagagtgaga  90180
ctccatttca aaaaaaaaaa aaaaaatctg cttcagctat tctgttaatc ttttgacatt  90240
acttagatgg tctggaaata aattttgaga ataacatgat tagaagtgag agagtataag  90300
catagttttg gagatacact cagaatagca ttatagattt tctcttttta ctaattggaa  90360
aaatggcagt tgttgaataa tagttttctt ccgtgaccct tgtgacttaa aaaaaaaaaa  90420
acactgaaat gaaataatcg aaccattttc tctaaacctt tgaatctgag ctctgcagtt  90480
aggtttataa tggtatatga aacctattag atatatactt ggaagtcata tgggatacaa  90540
accctgcttt tattatcttc ccctttttgac taacttgggt ctcaagtttc cttaattact  90600
gcacagtgga ccttgatgtt gctataaaga atgtgtaggg ctgggcatgg tggctcatgc  90660
ctgtaatccc agcactttgg gaggccaagg taggcagatc acctgaggtc aggagtttga  90720
gaccagcctg gccagcatgg tgaaaccccg tctctactaa aaatacaaaa aaattagctg  90780
gttgtggtgg cgagtgcctt taatcccagc tactccagag gctgaggcag gagaatcact  90840
tgatacattt agttaggaga gaaaatcata cttatgttag taattgctgc tgttcttcat  90900
atacttgtgg ttttgattgc cagcaaattc ctaacatttt ggaaaagaaa acagtaatgg  90960
gataaagggt aagggctaga gaggacagtt ttatttacct agatcttcag agaagcctga  91020
agcctctttt aggaagtaac atttgaactg agaatgtaat aaatacattt tccctttctt  91080
ctagttccaa gattatcccc taaaactcat agacccaggt ctcccagaca gaacagtatt  91140
ggaaataccc ccagtgggcc agttcttgct tctccccaag ctggtattat tccaactgaa  91200
```

```
gctgttgcca tgcctattcc agctgcatct cctacgcctg ctagtcctgc atcgaacaga  91260
gctgttaccc cttctagtga gggtatgtaa caaagggctt ctggatccat aatctcagct  91320
gtgaaattga atgttagagg gtgatattat atgaaaaaat tctaggttat ttttattcat  91380
agacaagtat ttttagtgca catttaaaag tttatgtaaa ttttgatgtt gtttaatact  91440
actaatttaa tatagtgtct gtgttacaaa ggttaacatt cctgggtgtc aaatacctac  91500
ataaataaaa ttattggtgt ttcatatgac atctgcaaag gaaaaaaagc ctctgtttaa  91560
atgaaagcat tattttccaa aaacatagga aatcaaaatt attgttcagt gttttcttgt  91620
tttgcttttc taacttatct gaattttttt taaaaaattg ttttctagct aaagattcca  91680
ggcttcaaga tcagaggcag aactctcctg cagggaataa agaaaatatt aaacccaatg  91740
aaacatcacc tagcttctca aaagctgaaa acaaaggtta gagtttaaag agtcattaag  91800
cttaactgta ggaataggaa gaagtatgtc taatttcatg cccatacaga atatttttgt  91860
tcaacatttc ttcttactat tgtgatagat aaatgtattg cttgacaaat tccaaaatcc  91920
aaatttaata tttgaaatta ttttctgatc ttatatctta ttctaatttc tatcatctca  91980
tactaaaaag aatgtgatgt taaagtttaa aaataaacct gtgtcttaac agttcttaat  92040
tttacaggta tatcaccagt tgtttctgaa catagaaaac agattgatga tttaaagaaa  92100
tttaagaatg attttagggt aagtattgta ctaactgatg aatttgagtt ttagaaaata  92160
agcattacta aagatttatc tatttataaa aatgcgttat gtatacagtc agaaacatca  92220
aaccatatat gtagaaagca gaacattttt aaagtggtct ttgcctatcc tttaagtggg  92280
ataactaaaa tcatgagatt tggtaacaac aatatgtagg tatcaaatga gagtatagcc  92340
ctgacatttg aaaccaccat agcacagctt actatttgat ggtcatttgt actttgttca  92400
gtgaagctag atattagtag agcaaggcca agtcattaat aatctagtgt ggcaaatgga  92460
agatgtactg gactctggtg ttctgaggta gttggagatt tatactttgt acacaaatat  92520
attgtggtca aaatctttct gtaacattat ttctctgtct tagcacaggc tttacttaac  92580
atctctcctt gattgtcatt tcattctttt gcatgttatt tactataggt atcgaggtag  92640
attttgagac caaccaataa atcttcttga aacttagctt cttagaaagg aaaatctaaa  92700
taccagcctt ttaaaaaaag tagctgaatt aaaggatgag tgaaccaaag gcaaaggtag  92760
cctttcctca gcctgtgttt tagctttcta aatgttaaca atagcttcat tcttgactta  92820
ttggtaacat tcaaaatact acttattatt tcatacttta gcacatgtat ctattcagct  92880
ttaatgctat taacagttgt taacctaagt tttcatttgt tggcgggcac ggtggctcac  92940
acctgtaatc ctagcacttt gggaggccga ggtgggcaga tcacctaagg tcaggagttc  93000
gagaccagcc tggtcaacat ggtgaaaccc tgtcttgacc aaaaatagaa aaattagcta  93060
ggcatggtgg cgcacacttg taatcccagc tacttggcag gctgaggcag gataatcgct  93120
tgaacccagg agacagaggt tgcagtgagc cgagatcaca ccactccact ccatcctggg  93180
cgacagagca agactgcatc tcaaaaaaaa aaaaaaaaaa aaaaagtttt tcaatttgtt  93240
aaacaatagt taacacatac aaatgataca aagaatattg aatatgatca tgtgcccact  93300
acccagctta gtaaataaag cattctaaca cagttaaact cctcttatgt atctgcccct  93360
cctcagctgc ttccccctgt ttccttccaa aaggaagggt ttcttttctg tgcagttctt  93420
tatatttata ctgcatatga atatatctgt gagcaataga tgatattttg cataatctta  93480
aatttgctat aaagtctttt tttttttttt aattgatcat tcttgggtgt ttctcgcaga  93540
gggggatttg gcagggtcat aggacaatag tggagggaag gtcagcagat aaaaagtgaa  93600
```

```
caaaggtctc tggttttcct aggcagagga ccctgcggcc ttccgcagtg tttgtgtccc  93660
tgggtacttg agattaggga gtggtgatga ctcttaacga gcatgctgcc ttcaagcatc  93720
tgtttaacaa agcacatctt gcaccgccct taatccattt aaccctgagt gacacagcac  93780
atgtttcaga gagcacaggg ttgggggtaa ggtcatagat caacaggatc ccaaggcaga  93840
agaatctttc ttagtacaga acaaaatgaa aagtctacca tgtctacttc tttctccaca  93900
gacgcagcaa ccatccgatt tctcaatctt ttccccacct ttccccccttt tctattccac  93960
aaagccgcca ttgtcatcat ggcccgttct caataagctg ttgggtacac ctcccagacg  94020
gggtggtggc cgggcagagg ggctcctcac ttcccagaag gggcggccgg gcagaggtgc  94080
cccccacctc ccggacgggg cggctggctg ggcgggggct gaccccccac ctccctcccg  94140
gatggggcgg ctggccgggc gggggctgac ccccacctcc ctcccggacg ggttggctgc  94200
cgggtggaga tgctcctcac ttcccagacg gggtggctgc caggcggagg ggcttctcac  94260
ttctcagacg gggcggctgc cgggcagagg ggctcctcac ttctcagacg gggcggccag  94320
gcagagacgc tcctcacctc ccagacgggg tcgcggccgg gcagaggcgc tcctcacatc  94380
ccagacgggg cagcggggca gaggcgctcc ccacatctca gacgacgggt ggccgggcag  94440
agacgctcct cacttcctag acgggatggc ggccgggaag aggtgctcct cacttcccag  94500
actgggcagc cgggcagagg ggctcctcac atcccagacg atgggtggcc aggcagagac  94560
gctcctcact tcccagacgg ggtggcggcc gggcagaggc tgcaatctcg gcactttggg  94620
aggccaaggc aggtggctgg gaggtggagg ttgtagcgag ccgagatcac gccactgcac  94680
tccagcctgg gcaccattga gcactgagtg aacgagactc cgtctgcaat cccggcacct  94740
cgggaggccg aggctggcag atcactcgcg gttaggagct ggagaccagc ccggccaaca  94800
cagcgaaacc ccgtctccac caaaaaaata cgaaaaccag tcaggcgtgg cggcgcgggc  94860
ctgcaatcac aggcactagg caggctgagg caggagaatc aggcagggag gttgcagtga  94920
gccgagatgg cagcagtaca gtctagcttc ggctcggcat cagagggaga ccgtggaaag  94980
agagggagag ggagaccgtg gggagaagga gaaggagggg gagggggagg gggggagagg  95040
gagagggaca atgatgtctt gctgtaggta ttcttcccca tttgaatttt ttcctcagca  95100
ttattttttt taacatcatt cagtctcctc ttatactaca cttggattga atttaatatc  95160
tcatgaagaa aaaacatttc tactttgaag catgtgaatt agcatgtttt tataacagct  95220
ttattgagat ataatttaca tatataaata aaccgtttaa agtgtataaa tcagtggttt  95280
ttaatgagat ataatttaca tatataaatc aaccatttaa agtgtataaa tcagtggttt  95340
ttaaaatatt cacaatgttg tacaaccgtc ttctcagttg attttaaaac atactcttca  95400
cccccaaaag aaaccccgtg cccagtttag cagtcgttcc acatttgcct ccagcccttc  95460
tctttcccct actcccaacc ctaagcaacc gttaatctac tttctgtctc tatggatggg  95520
cttatttggg gcaaattcca tttcatacaa atggaataat aaaatatgtg gcttttatga  95580
ctggcttctt tcactcagag tagtgttata aaagttcatc catgttggag catgtttcag  95640
tacttcattt ctttttgtga ctgactaata ttccttgatg tggataatac cacattttgt  95700
ttatccatta atcagtttgt agctatttgt ggtgttctca ctgtttgact attctgaata  95760
acactgccac aaacatgagt gtgcagtttt tttctcgtcc tatcttttca tttcttttgt  95820
gtacctacct aggagttgaa ttgctgggtc atatggcaac tgtgtttaac cttttgagga  95880
actaccaagc tatttgccaa gatatctaca ctattttaca ttcccaccag cagggtatga  95940
```

```
gggtttctgt ttctccacat ccttgctaac acttattgtc ttgtcttttt tgattatagt  96000
catccttgtg ggtgtgaagt gttaacctca ttgtggcttt aatgtgcagt tctttcatgg  96060
ctaatgatgt tgaacatctt ttgtgtttat tggccattta tatatcttct ttggattgat  96120
gtctgttcaa atctttaccc attttaaaaa ttgagttgtc tttttattat tgggttgtgg  96180
gagttcttta tatattgtgt gtacaagtcc ctgttagata catggtttgc aaatgttttc  96240
tcctgttctg ttggttgtct ttttactttt tcatcccttg aagcacaaaa atttttaatt  96300
ttgatgaagt ccaatttatc tgattttgaa gtaagctttt ggtgtcgtat ctaagaaaat  96360
actgtttcat caatcattaa ggtttattac tcttctgggt ttttttaaga attacattta  96420
gaggtgtgat ccatttggag caactttttt tttcttttga cacagaatct cgctcttttg  96480
cttaggctgg agggcagtgg tgcaatcttg gctcacagca gcctcagcct cctgggctca  96540
aatgagtagc tggtactaca ggtgtgcacc accacacctt gctattaata acttttgtat  96600
tttttgtag agacagaatt tcgccatgtt gcccaggctg gtctcaaaca cttggactca  96660
agtgacacgc ccacctcagc ctcccaaagt gaaaaattgc tttcaccttg cactgcggac  96720
tcgccctgaa ttctttcttg tgcaagatcc aagagccctc tctgggggtc tggatcggga  96780
cccctttcct ataacaatat tatgagaata acatttgatt ttttttaagt gaaacaaatt  96840
gttattaaaa aattaaaaaa ggtcatagga gagtgacttg gtgctcagcc cattttgagc  96900
agttatttaa tatagcataa ggtggggttc aaattcattc tttatattaa tttttttattt  96960
ctaattgaca cataaccata cacttataac catttttact gtgtaagttc agattcattc  97020
ttccgtatgt aggtattagt tgtcccagca ccatctgtta aaaagactat tcttggccag  97080
gcacagtggc tctcaacgcc tgtaatccca gcactttggg agtcccaagc aggcagatca  97140
catgaggtca ggagttcgaa accagtctga ccaaatggtg aaaccgcatg tctactaaaa  97200
atacaaaaat tacctgggtg tggtggcgca cacctgtagt ctagtcccac tactgtagtg  97260
gctgaggcag gagattcgct tgaacccagg aggtagaggt tgcagtgagc tgagatcatg  97320
cactccagtg tgggcgacag agtgagactc catctcaaaa aaaagactat tctttcctcc  97380
attgaattat cttcacatgc ttgttggaag tctgttgact acaaatgtga aagtttatta  97440
ctggactctg aattgtcctc cactgaatct ctatgtctta tccttatggc agtaccatac  97500
tgtcttgatt agagttactg tattttaaaa ggctgtactt tttcagttag cagaaaacat  97560
tttagctatc agcacaactt tctgtaaacc ttcattaatg cttgacttaa attccaagaa  97620
ggagcaacat aaaaagtctt atctctttag gagttttagt cttactactt tttaggtgcct  97680
gaataaccaa atgtattatt tagcctctta ctaataactc cttgatccat aggggcatac  97740
caggaagaaa agaagtggtt tttaaaaaat gagagtgggc cgggcacggt ggctgatacc  97800
tataatccta acactttggg aggctgaggc gggtggatca cttgaggtca ggagtttgag  97860
accagcctgg ataacatggc gaaaccctat ctttattaaa aatatataaa ttagccgggc  97920
atggtggcac atgcctgtaa tcccagctac tcaggaggct gaggcaggag aatcacttga  97980
atccaggagg tggaggttgc agtgatccga gattgcatca gtgggcgaca gagcgagaat  98040
ctgtctcaaa gaaaaaaaaa gagagtggaa aaaaaaaata tgtgtcccag aacttaaatt  98100
ttaattaaaa aaaaataaaa gagtgaactt tctaattgtt ctcttcagat aatataatgt  98160
tattctctta tgttttattg cgtatttcct gtgtaccaga tgctgttctt catgcttgta  98220
tgttaaatct tgtctaacat ctctgtcaag caagttctgt ttgtatctgc actgtgtata  98280
ttaggcagct tgggcaaaga gaagttaagt aatctgccca aactcacatg gctagtaagt  98340
```

```
aagagggctg accatctggt gtttaagctt ctagcagtgc tttgaatagt aactaatgca  98400
tagtgcatgc tgcactgtca gtcagtgatt cattagagct aacttcatga catgctcata  98460
gccccaaact gcatttgttc acaaatatct gtagtccttc atttaggcag aaatagaaat  98520
accttgtgtg tttgttgttc cttccctttt gagccatatg cagagtgctg atagctttat  98580
ttgtgtaaga attgctagta atttgatctg ttttgggtta ataatgtggg ttttagaggt  98640
aaatggacct aggtttgaat gttggcctct atacatcatg tgcgtaacat tgtggcatgc  98700
tatctacttc ccccaagcca aaatgggtta attttagaac ctgcttcata gtgttcctgt  98760
gagagctcga tgagatattg cctataaagt gtttagcata gtgcctagca catggtatgt  98820
attcaataca tgttcattct tactagcaaa atatagatga cccagtattg tacagagtat  98880
gtacaatggt gtcattgtac catttcatgt ggagtcacat aagaatttca gttttctgct  98940
gggcatgatg gctcactcct gtaatcccag cactttggga ggctgaggtg gatggatcag  99000
ctgaggtcag gagttccaga ccagcctggc cgacatgatg aaaccccatc tctactaaaa  99060
atacaaaaaa ttagccaggc gtggtggcag gtgcctgtaa tcccagctac tcgcaagact  99120
gaggcaggag aaatgcttga acccgggagg cggtggttgc catgagttaa gatcgtgccg  99180
ctgcactcca gcctgggcaa taagagcgaa actccgtctc caaaaaaaag aaaaaaaaag  99240
aacttaagtt ttccattaga tttagtatag tgcagagagg aaatacagca gagtgctata  99300
ttccatatat agcaatatag cattagaaca atatattcca atacagcaga gtgctatatt  99360
cagataccaa ctagtggact tgctatttgt aagatggcaa taatagtatc tacatcaaat  99420
agggctgttg tgaagactaa atgaataagt ctataaatag tttagaacag tgtctggaca  99480
ggtacagtgg ctcatgcctg aatcttagca ctttgggagg ctgagacagg tggatagctt  99540
gagctcaggc attaaagacc aacctgggta acatggtaaa accctgtttc tacaaaaaaa  99600
tacacacatt agccaggtgt ggtggcacat gctaatagta ccagctactc aggaggctga  99660
ggtgggagaa tcacttgagc ctgggagatg gaggttgcag tgaggtgagc ttgcaccact  99720
gcgctccagt ctgggcaacg gagtcagacc ctgtttggaa aaaaaaaaaa aagtgtccaa  99780
cccatagtaa gaaatgcaga tgtgtttgac attgtaagaa aaagcaacac caaaagtctg  99840
atttttgcct tcactcaaga actcttatga taattaaact ccgaagtcct tggcaatata  99900
tatagttggt ctgttatgtg gatcgcctct actaaagatt tttgtgaaca aatgaaagtt  99960
taagtagtaa gttcctacat cgtgacttaa attgccagtg tgcccacata aataccctgt 100020
caacatttgc ccttagccac ttgactcttt agctatattg gtaatgcagt aaagcttgcg 100080
atgcgccaga gttgcataat gctgtttgcc atgacaccaa gagccttggt aatgaaacca 100140
ttgaaattgg tttgcctata ctgaggctga agaggtatct tggctctcta attttaaggc 100200
aaccttttg gctgtgtagg tttctcttta gcttgtttct caccacctgg ggctgtggct 100260
taggtccgtt gtcctaacct gtggcttagg ttctgttttt gttgcttgta cttgctcccc 100320
ctttttcag ccattcctgt tttctttctt ttgtagagga tgccatctta aatcatcttc 100380
agccagtggt agcattttat tttttctggt ctgcaaactt aaaaacctca tcacttattt 100440
tgctaatatc tttgtcttct gttctttttg atggtccttg gttttgcagt ctactttaaa 100500
ggtttttatt tttttatggg tacatagtag acgtattatt catagggtct gtgagatatt 100560
tagataaagg catataatgt gtaataatca cattagggta aatggggtat ccatcaccat 100620
catcattcat catttctttg tgtaatgaac gttgcaattg tactccctca gttattctaa 100680
```

```
aaagtacaac aaattaatgc tgactgtagt caccctgctt tgttgtcaaa tactagatct 100740
tattcattct ttatttaact ttttaaattt taaacttatt ttatttattt atttttagac 100800
ggagtctcac tctgtcgcca ggctggagtg cggtggcgca gtctcaactc actgcaacct 100860
ccgcctccag ggttcaagtg attctcctgc ctcagcctcc tgactagctg gaactacagg 100920
cacgtgccac cacgcccagc taatttttgt atttttagta gagacggggt ttcactatgt 100980
tggctgggat ggtcttgatc tcttgacctt gtgatccggc tgccacagcc tcccaaagtg 101040
ctggggttgc aggcgtgagc caccgtgccc ggcctttaaa attattttaa atcattttaa 101100
tatctttttc atttctgcct ccggtcctgc agagttctta ttcgttcttt ctaaattttc 101160
tttgcaccca ctaatcacct catttccctt cttctcccca ttacccttcc caacttctgg 101220
taaccattct gctatctcca tgtgttcaat tgtttttatt tttagtgcct gcaaacgagt 101280
aagaatatgc aaagtttatc tttctgtccc tggcttattt tacttaacat aatgtcctcc 101340
agtgccatct acattgctgc aaatgacagg atctcattct tttttatggc tgaatggtaa 101400
tctattgtgt atatatacca cattttcttt ctccatttgt ctgtcagtgg acacgtaggt 101460
tgattccaaa tcttggctgt tgtgtatata gtgccgtagt aaacatggga gtgcagatat 101520
tccttcaata aactgatttc ctttctgagt atatacctag cagtgcaatt gctggatcat 101580
atggtagctc tatttttagt tttttgagga atttccatac tgttctccat agtggtttta 101640
ccaatttaca tgtccaccaa cagtgtgtga aggttcccct ttatccacat cgttaccagc 101700
atttgttatt gcctgtcttt tggataaaag ccattttaac tggggtgaga tgatatcttg 101760
ttgtagtttt aatttccatt tttctggtga tcagtagtat tgaatacctt tcatatacct 101820
gtttgccatt cataaataac gatgaggtct tgctgtttgg cccaggctgg tctcgaactc 101880
ctgggctcaa gcaatcctcc caccttggct tcccaaaatg ctgaaattat agttgtgagc 101940
cactgcacct ggccttgtat gtcttccttt tttttttgtt ttgttttgtt tttgagacag 102000
agtctcactt tgttgcccag gctggagcgt agtggtgtga tcttggctca ctgcgcccta 102060
cacctcccgg attcaagcaa ttctcctgcc tcctgccacc atgtctgcct aatttttgta 102120
tttttagtag agacgggatt tctccttgtt gcccaggctg gtcttgaact cctaacctca 102180
ggtgatttac ctgcctcagc ctcccaaagt gctaggatta caggcgtgag ctgctgcgcc 102240
cagcctgtat gtcgtctttt gagaaatgtc tattcagatc ttttgcccat ttttaattga 102300
gttactaaaa ttttccctat ggagttgctt gagtgccttt tatattctgg ttattgatcc 102360
cttgtcagat gagtagtttg caaatatttt ctcccattct gtgggctgtc tcttcacttt 102420
gttgatggtt tcctttgctg tgcagaagct ttttaacttg atgtgatccc atttgtccat 102480
ctttgctttg gttgcctgta cttttggggt attactcaag aaatctttgc ccagagtaat 102540
gtccctggga gtttaatgtt ttcttttagt agtttcatag tttgaggtct tagatttaaa 102600
tctttagtcc attttgattt gatttttttt taatatggtg ggacacaggg gtctggtttc 102660
attcttctgc atatggatat ccagttttcc cagcaccatt tattgaagag actgtccttt 102720
ccccagtgta tgttcatggc ttctttgtgg aaaatgagtt cacttagacg tatggattca 102780
tttctgagtt ctctgttctg tttcattgat ctatatcttt ttttatgcca gtaccatgcc 102840
attttggtta caataatttg aagtcagata atgattcctc ccgttttgtt cattttgctc 102900
agtatggctt ttgctctttt gggccttttg tggttcccta caaattttag aattattttt 102960
gtctacttct gtgaggaatg tcattggtat tttgataggg attgcactga atctgtagat 103020
tgctttgagt attatcaaca ttttagcaat attaattctt ctaatccata aacatggaat 103080
```

```
ctcttttcat gtttttctg tgtcatcaat ttcagtgttt taaagttgtc attatagaaa 103140
tcttttactc atttggttaa gtttattcct aagtatttta ttatatttgt agctattgta 103200
aatgggattg cgtttaaaaa atttttcaga ttgtttgctg ttaaatataa aaatgctcct 103260
gatttttgtg tgttgatttt tgtatcctgc aattttactg aatttgtttg tcagttctaa 103320
taggtttttc ttttttggag tctaggtttt tccaaatgta agatcatatt atctgcaaac 103380
aaggataatt tgacttcttc cattccagtg tggatgcttt ttatttcttt ctgttgtctg 103440
attgctccaa ttaggacttc cgagtattat gttgaataac aatggtgaaa gtgggcatcc 103500
ttgtcttgtt ccagatctta gaggaaagcc tttcagtttt tcccttttca gtatggtact 103560
agttatgggt ctgtcatata tggcttctgt tttgttgagg tatattcctt ctatacccag 103620
ttctttgggg tttttttgtt tgtttgtttt tgagatggag tctcactctg tcacccaggc 103680
tggagtgcag tggcgcaatg ttggctcact gcaagctcca cctcctgggt tcatgccgtt 103740
ctcctgcctc agcctcccga gtagctggga ctacaggtgt ccgctaacac gcccggctaa 103800
tttttgtat ttttagtaga gacggggttt caccgtgtta gccaggatgg tctcgaactc 103860
ctgacctcat gatctgcccg tctcagcctc ccaaagtgct gggattacag gcgtgagcca 103920
ccacgcccgg ccaagggttt taatcataag gggatgtggc attttatgtg atataaatta 103980
tatatttata tcatgtgata tatatttata tcatacacag tataaataat atatatatat 104040
atttttagt ctttgtcttt tattctgtta agatgtacca tgtttattga tttgcgtatg 104100
tcgaaccatc cttgcatccc tgggatgaat cccacttagt catgatgaat gatcttttta 104160
atgtgttact gaattcggtt tgctagtatt atattgagga tttttgcata atgttcttca 104220
gagacactgg cttctagttt tcccttttg atgtgtcctt tggttttgta tagggtaata 104280
gtggccttgt agaatgagtt tagaagtatt ccctcttcct gtattgtgtt ggaatagttt 104340
gagtaggatt ggtattagtt cttctttaaa ggtttagtag aattcagcag tgaagccatc 104400
aggtccatgg cttttctttg ctgggagact atttcttata gctttgatct cgttacttgt 104460
tattggtctc gttacttgtt attgtatttg ggttttggat ttctttgtgg ttcagtcttg 104520
gtaggttgta tgtgtctagg aatttatcca tttcttcaag gttttccaat gtatcagcat 104580
atagatgctc atagtagtct ctaatgatcc tttgaatttc ggtggtaaca attataatgt 104640
ctccttttc atctctcatt ttattatttg ggttttctct tttttttctg agtctggcta 104700
aaggtttgtc agttttgttt atctcttcaa aacaatttac tgttttattg atcttttgta 104760
ttttcttcat ttcaatttta tttatttctg ctttgatttt ttttatttct tctactgatt 104820
ttaggttttg tccttgcttt tctagttctt taggatgtat tggcagatga agtttttcca 104880
ctttttgat gtaggcactt actgctgtaa acattcctct tattgttgct tttactgtat 104940
cctataggtt ttgataagct gtgtttccat tttcatttgt ttcaaggaat tttccagttt 105000
tcttcttaat ttcttcatgg acccactggt cattcaggag catattgctt aattttcatg 105060
tatttgtata ctttccaaag ttcctcttgt tatctagtgt tattttattt tatttttatt 105120
tttgtttttt tgagatggag tctcgctctg tcacccatgc tggagtgtag tggcgcgatc 105180
tcggcttact gcaacctctg cctccccagt tcaagtgatt cttctgcctc agcctcctga 105240
gtagctggga ttacaggcat gtaccaccac tcctggctaa tttttttttg tatttttagt 105300
agagaggggg tttcaccatg ttggtcaagc tgatctcgaa ctcctgacct cagatgatcc 105360
acccaccttg gcctcctaaa gtgctggaat tacaggcatg agccaccgtg cccggcctct 105420
```

```
agtgttatct tattgtgatc agagaagata gttgatatga ttttaacttt tttgaatttt 105480
tatttattta tttgtttgtt tgtttgtttg tttgtaacag agtctcactc tgttacccag 105540
gctggagtac atgtcatgat cttggctcac ctgcaacctc cgccttcctg gctcaagcaa 105600
tcctcccacc ttagccttcc aagtagctgg gactacaggc acatgccgtc acatatggct 105660
gatattttg gattttttt tttttgtag agatggggct ttgcgatgtg tcccagggtt 105720
gtttcgaact cctgagctca agcaatccac ctatttcggc ctcccaaggt gctgggatta 105780
cagacatgag ccactgtgcc acgtcaaatc tttagacttg ttttgtggct taacataggg 105840
tctatctttg agagcaatcc atatgttgag gagaagaatg tgtattctat agctgttgga 105900
cacaatgttc tgtaaatatg tattgggcct atttggtcta tagagcaaat taggtctaat 105960
gtttctttgt tgattttctg tctgaatgat ctgtccattg ctgagagtgg ggtgttgaag 106020
tttccgactg ttactgaggt ctgtttctct tttttgctct aataatgttt gctttatata 106080
tctggatgct ccagtattgg ttgcatatgt atttatactt gttataacct cttgccgaat 106140
tgatcccttt atcattatac aataatcttc tttgtctgtt tttatagact ttgtctcaaa 106200
atctatttta tctaagcata gctactcctg ttcttttctg gtttccattt gcatggaata 106260
ttgttttcca gctcttcaat tttagtctat gtgtgatttt ataggtaaag tgtgtttctt 106320
gtaggcaatg gatctttggt tttttttttt tttttttga gacagagttt tgctattgtt 106380
gcccaggctg gagggcaatg gcgctatctc agctcactgc aacctccgcc tcctgagttc 106440
aagcgattct cctgcctcag cctcccaagt agctgggatt acaggcgcct gccaccaagc 106500
ccagctaaat tttttgtatt ttcagtagag atggggtttc agtatgttcg tcaggctgtt 106560
cttgaactcc taacctcagg tgatttgcct gccttggcct cccaaagtcc tgggattaca 106620
ggcgtgagcc accgcaccca gccttttttt taaatccatt tagccactct gtatcttttg 106680
attggagagt ttagtcgatt tacattcagt gttgttactg attagtgagg acttaactac 106740
taccattttg ttacttatta tctggttgtt ttgtagtcct actccctccc ttccccctc 106800
tttttacttt cctcttcgct cctttttcc ctccctccct tccttgtttt gaaagtgatt 106860
ttctctggtg gtatgtttta atttcctgct ttatattttt tgtgtatctg ttgtaggtgt 106920
ttttgattta agatcaccat gacagctggg tgcagtggtt cacacctgta atcccagcac 106980
tttgggaggc cgaggtgggt ggatcaagag gtcaggagat tgagaccagc ctggctaaca 107040
tggtgaaacc ccatctctac taaaaataca aaacttagcc aggcgtggag gcacgtgcct 107100
gtaatctcag atactcagga ggctgaggca ggagaattgc ttgaacccag gaggcagagg 107160
ttgcagtgag tcaatattgt gccactgcac cccagcctgg gcgacagagt gagactccgt 107220
ctcaaaaaaa aaaaaaaaaa agagatcaca taagggttgc aaataacatt ttataaccca 107280
ttattttaaa ccaatgacaa cttgaaactt tgattgcaaa aacaagcaag caaagagaaa 107340
actaataaaa actctacact tcatctgccc gctttttaac ttttgttgtt tttatttata 107400
tctttattat actatgtctt aaaaaactgt agttataagc caggcgcagt ggttcacgtg 107460
tgtaatccca gcactttggg aggctgaggt gggcggatca cctaaggtca ggagttcgag 107520
accagcctag ccaatatggc aaaacccct ctctactaaa aatagaaaaa ttagccggac 107580
atggtggcgg gtgcctgtaa tcccagctac tcggaggctg aggcaggaga atcacttgaa 107640
cccaggaggc ccaggttgca gtgagccgag agtgcgccac tgcactccag tctgggcaac 107700
agagtaagac tgtctcaaaa aacaatacaa aacaaaacaa aaccctggcc tagtggctca 107760
cgcctaatcc cagcactttg gaaggcaaag gtggggcgaa tcacaaggtt aggagttcga 107820
```

gaccagcctg accaacgtgg tgaaactctg tctctactaa aaatacaaaa attagccagg 107880
cgtggtggca cgcacctgta atcctagcta ctcaggaggc tgaggcagga gaatcgcttg 107940
aacctgggag gcggaggttg cagttagccg agatcgcgcc actgccgtcc agcctgggca 108000
gcagagcaag actctgtctc acaaaaaaaa aaaaaattgt agttcttatt tttgaaaggt 108060 tcattttta ttcttcctgc tcaaaatatg agtagtagtt tatacaccac aattacagtg 108120
ttacaatatt ctgtattttt ctgtgtactt gttaccagtg agtttttgca ccttcaggtg 108180
atttattatt gtttgttaac atccttttct tgcagattga agaacttttt tttttttttt 108240 tttttttga gacagagtca tgctctgtta ccagcctgga gtgcagtggt gccatcttgg 108300
ctcactacaa cctccaactc ccaggttcaa gcgattcttc tgcctcagcc tcccaagtag 108360
ctgggattac aagcatgtgc caccacgccc agctactttt tgtattttta gtaaagacgg 108420
ggttttgcca tatttgccag gctggtcttg agctcctgac ctcagggtga tccgcccgcc 108480
ttggcatcct aaagtgctag gattataagc gtgagtcatc gtgcccaact tggttgttta 108540
ttttcaaata gcctgaattc aagctcacta atgttttctg ctgcttgata catttctgct 108600
attgagagac tgatgcattt ttcagtttgt caattgaatt tttccacttt gggatttctg 108660
cttgattctt tttactaata attattgcag tctcttttt aaatttatag gattctgaat 108720
ttgttctctg tattatcttg gatttcgttg aactttctca aagcattcag cttgaattct 108780
gtctgaaagt tcacatatct cttatcactt gggaattggt cactggtgtc ctttattttt 108840
agttcatttg gtgaggtcat gttttctcag atggccttga tgcttgtgga tgttcatcag 108900
tgtctgggca ttgaagagtt gggtattctg ttctttgtag tctggttttg tttgtacgca 108960
ttcttttttt tttttttctg tttttgagac agagtctcgc tctgtcgccc aggctggagt 109020
gcagtggcac agtctttgct caccgcaacc tccgtctccc ggattcaagc aattctcctg 109080
cctcagcctc ctgagtagct gggattacag gtgcgtgcca ccacgcctgg ctaatttttg 109140
tatttttagt aaatatggtg tttcaccatg ttggtcaggc tggtctcgaa ctcctaacct 109200
cgtgatctgt ccgccttggc ctctcagagt gttgggatta caggcgttag ccactgcatc 109260
cggctcccat tcttcttgag aaggtttttc aagtattcaa agggaattaa gtgttgtcat 109320
ctaagtcttc gctcactgca gccatacatg cattagaggg caccccaaga ctagtaatgt 109380
tgtgactctg tagaggtatc accttggtag tcttggggaa gatctgggag aattccctgt 109440
attaccaggc agtctcttgt cctcttacat ttctccaaac aaatggagtc tctctttgtg 109500
ctgagctgct tggagtttgg ggaagggtga cacaagcact gccatggcca ccgtcactgg 109560
aactgtactt ggtctcaccc aaggcctgtg gcagctattt tctggccacc actgatgtta 109620
atttaaggcc caagggtgct ttagtcagta ggtgaagaat cctgcaagaa ctgggtcttt 109680
actttcagtg cagcaggttc ccttctggcc cagggtgtgt ctagaaatgc tgcccaggag 109740
ccagggcctg ggatcgggag ctttaggaat ctgctttatt gtactggggc tgagctggca 109800
cccacttgca agataaagtc ctttttactc ttctctcacc tcaagcaggt gggtctcccc 109860
atggacacca cagctgtgaa tgtgcggggt catatctgaa gctggcacaa tacgacatgg 109920
caccttgttt tttattcaag gcacaagggc tctttagtca gctggtggtg aatcctacta 109980
ggactaggta tttcccttca aggcaatggg ttcccttctg gtccagaata tgtctagaaa 110040
tgtcatctgg gagctatggc ctagaattga ggcttcagaa ctatgcttgg tgctttattt 110100
tactgtggct gaactagtat ccacattgca agacaaagtc ctccctactc ttccctctcc 110160

```
tcccagagct gtgagctgtg gtacctggag ttgggggaag gctggcacaa gcactccctt 110220
ggccacccta gctggtgtct cagtgggtca catgtacccc aagtccactg actatgagcc 110280
cagcacagta ccatgacttg tccaggaatt gcagtccttc tggtctagac tgcctttcaa 110340
gtttatttag gaccccagag gactttaccc acggtggtgg ggcttaccaa aattaagatt 110400
cttttggttt tttttggcag agtttcgctc ttattgccca ggctggagta tagtgacgca 110460
atctcagctc accacaacct ccgcctcccg ggttcaaata attctcctac ctcagcctcc 110520
tgagtagctg ggattaccgg catgcgctac cacctctggc taattttttt gtttttagt 110580
agagatgagg tttctccatg ttggtcaggc tggtcttgaa ctcccgacct caggttatcc 110640
gtccgcctcg gcctcccaaa gtgctgggat tacagaccat agtgcccagc ccgaaattca 110700
gattctaatc actgggatgg acaattcccc tctgactagg gctagtctaa atactccctc 110760
tgtgggtgct ggctgaattc tgtcctatgc tgctttccac tgtgacaggg cagcactgag 110820
tttcaatgca aaatcccaca gtcatttctc tctctctccc ccgagcacac agattctttc 110880
tccaccccac actgcattgt gggggaatgt caggggtgtt ggaggggcag ttcaagacta 110940
tcttccttat ctttttggt gtctttttcc ttgataggat gtcaaaactg ggtactgtga 111000
tcgcttacct aatttttggt tcttatgaag gtgctttctt gtgtggatag ttgttcaatt 111060
tggtgctcct tgttggggat gatcactgga aggttctgtt tggccaccat gctctgtctc 111120
ttctcccctg ccatctcctt tttttactta ggggtttaga atgtctaact gaccaatatg 111180
tacagtcagg tctcattctg aattcaccta cttaatgacc ttccaagctg actaggccca 111240
gcgcttagtc cagcctccat gacggtccct ccacatccta attagcctcc ctccagttca 111300
tttcacacaa agctgctgtg ttcacctttc tgaactataa atctgcccag tactctaccc 111360
tacttaaaat tccgtataga ctgcccattt gccctgagaa ttaaaagcca aagtcctaaa 111420
cgtagctttt taaaactttt tttttttttt ttttaatttt tagatggagt cttgctctgt 111480
cacccaggct ggagtgcagt ggtgtgatct tggctcactg caacctccgc ctcctgggtt 111540
caagcaattc tcatatgtca gcctcccaag tagctgggat ttacacgtgt gccatcacgc 111600
ctggctaatt tttttttttt atctttagta gagacggagt ttcaccatgt tggccagtct 111660
ggtcttaaac tcctgacctc aagtgatcca cctgccttgg cttcccaaag tgctaggatg 111720
ataggtgtta gccactgcac gcagccctga acatagcttt taagttcctt tattgtcata 111780
ttccttttga cgagtctatc attttctgac tcacttgtac atgtgtgtct cacccttggt 111840
ccagccattg gtgcttttct ttacttcttt atttttgtta ttttatttta ttttattatt 111900
attttttaaa tgagacaggg tatcactatg ttgcccaggc tggtcttgaa ctcctgagct 111960
taagcagtct gcttgtctca gcctcccaaa gggctggaat tacagtgatg agctactgtg 112020
cccagctcat tggtgctatc tttttttttt tttttgagac ggagtctcgc tctgtcaccc 112080
aggctggagt gcagtggcgt gatcttggct cactgcagct ccacttccca ggttcacacc 112140
attctcctac ctcagcctcc cgagtagcag ggactatagg cgcctgccac catgcctggc 112200
taatttttgt atttttagta gagatggggt ttcagcgtgt gagccaagat ggtctcgatc 112260
tcctgacctc gtgatccgcc tgccttggcc tcccaaagtg ctgggattac aggcgtgagc 112320
caccgtgccc ggcccccatt ggtgctattg ttttatgtga tagagccagc ttctcccttt 112380
tctttggatt tttaaacata ctcttccttt tacttagact attctccatc ccaacacctt 112440
tcctaaactt ctttcacacc ttagactagc tgacacttta ctgagaaacc tttcttttt 112500
ataggttgct ttttctatag actctcttag catttactca ttttattgtg aagtgtctga 112560
```

```
tcttatttaa atgacaagta taagaggata gaaactattt catatttttc tcacccagca 112620
ggcacaattt ctgacatgtg gtaagcactc agtaaatatt gaactttaga ggctaggaca 112680
tttgagtgct ttggtgactg tggttgtgct atataggtac tctgttattg ttagtttata 112740
gtaaaagcat tactcttaaa gtatgaaaaa agccttattc agaacatttc atgcgtatag 112800
ttaatattac gtagcttgtg ctcatggcaa aaatgtatta ctaaagttat ttaagatatt 112860
taagtataat tgtttccttt atttagttac agccaagttc tacttctgaa tctatggatc 112920
aactactaaa caaaaataga gagggagaaa aatcaagaga tttgatcaaa gacaaaattg 112980
aaccaagtgc taaggattct ttcattgaaa atagcagcag caactgtacc agtggcagca 113040
gcaagccgaa tagccccagc atttcccctt caatacttag taacacggag cacaagaggg 113100
gacctgaggt cacttcccaa ggggttcaga cttccagccc agcatgtaaa caagagaaag 113160
acgataagga agagaagaaa gacgcagctg agtgagtaaa cctggaactt agaccatcct 113220
gttactcaat taacttttttt tttttaaag gcatttaggt ccttccaact gtgaagaatc 113280
catctggact tttagactac tttatacatt gcccttagtt tacaaacagc tagtccaaac 113340
aaatgacatc ttaagtaaat gaggttattg caccctgtgc tactcttctg ttcttcccct 113400
tttttgtacc ccagggctag aaaaacaagg cataaattaa gaaaagtttt tctgtaaatg 113460
aacaggagtt gaaaaattat caattcaggg gacctatctt tactggattc cactcattag 113520
tcaccctcac tgtgctgcta ggttgaaaaa ctgccactgt caaggagaga agcatgcggt 113580
gcttctactt ggaattcaaa atatttttca tcagaaactg tgttttagtt aatgtttaga 113640
tttgttaaga tagacttaat tctgcacatt cagtatatta attaaatgga cttttagggg 113700
ctaacctcag aacttaacta ccattgactt aggtgtttgg gtaccaaaca atccagttaa 113760
agctgaagtt ttggaatgca gcttattgat aaattgggga ctgcttattc ttgatttgag 113820
gcaatttttt tttacagcca tgactttttc caggtatgtc atgtaaaata tcttctcaca 113880
taagaattac tgcatgctag aatattggta tgttgactgg tagctcatac ctataatccc 113940
agcactctgg gaggtccaag caggtagatt acttgaggtt aggagttgaa gaccagcctg 114000
gccaacatgt gaaaccctgt ctgtactaaa aatacaaaaa ttagccaggc atggtggtag 114060
gtgcctgtat cccagctact cgggaggctg aggcaggaga attgcttgaa cccagaaggt 114120
ggaggctgca gtgagccgag atcatgccac tgcactccag cctgggtgac agagcgagac 114180
tctgtctcaa aaataaataa ataaataaat aaaaggatac tgttatgtta agaattgctt 114240
ttaaggatat ttcataagta gctactgtct tttcagctca agtgtttgtt gattggccag 114300
gcgtggtagc tcatacctgt aatcccagca ctttgggagg ctgagtcagg cagatcactt 114360
aaggtcagcg tggccaaaat ggtgaaaccc catctttact aaaaataaat attaaaaaaa 114420
attagctggg cgtggtggca gtctcctgta atcccagcta atcaggaggc taaggcaaga 114480
gaatggctta aactcgggag gcagaggttg cagtgagcca agattgcact gctgcactcc 114540
aacctgagca acagagtggg actctgtgaa ggaaaaaaaa aaagtatttt ttgattgcct 114600
ttgagaggaa cggttgtata ttactcagat ttttaaaaaa ttgttctttt atggctgtat 114660
tctttaaggg attaaggaat gggcaatata agtgtatatg tttcaataaa aacgattagt 114720
gatcttctag tgagaacagt ttaaatctat atttagcaat ttttttttaaa ttgtcaggta 114780
tggaagattt tagagcaacg taaagtccat gtagatttca ctggccttta tattttttttt 114840
aggcaagtta ggaaatcaac attgaatccc aatgcaaagg agttcaaccc acgttccttc 114900
```

tctcaggtag gtttattact ttctttgagg ttatctagtc ccaaaaaaag aaaaattatt 114960
agtaatagtc cttcttccat acctgccatc tgaattttgt tttagtgtgc tgaaccaacc 115020
ttctttcttt tttttacatg gccattaatg aatacttttt aaacattaaa aaaaggtctt 115080
tgttttgtca tcaattagat gtgatcttgg gcaaatcttt gaatttctct gacccagaat 115140
ttgacgatgg ttggctagct aggctgtcag gtttatagat acgtcctctg cacctgaggg 115200
ttttgcatca ctggattcaa ccaaccatgg atcaaaaaca tagttaggat aatctatact 115260
gaacacatgc agacgtttcc ttgtcattat tccaaaacaa tacagtaaag catttacctt 115320
gttttaggta ttataaataa tctagagatg atgtaaagta tataggagga tatgcatagg 115380
ttgtatgcga atactacatg attttatgta agggacttga gcattccaag actttggtat 115440
cttcacaggg tactgtaacc aatcccccac agatactaag agatgactgt actattgtta 115500
ttattcgact gagatcataa gaagatatat ttatttttaa tttttaaaaa cacttccatc 115560
agtttcttaa aaatagctgc cactgttttt aatatttttt aattgacaaa gttttaagtt 115620
cctactgaaa catttttttct tttattgaaa tgtgaaaatt tatgtgctgt gtttttgttt 115680
tcaataaaag ggacatagtt aaagcaagta aaattagaaa gactgggaaa atccgtcttt 115740
aaattgcaat aatagttcat ctgttacctt gagataattg aatttattgt tgtttttgta 115800
gccaaagcct tctactaccc caacttcacc tcggcctcaa gcacaaccta gcccatctat 115860
ggtgggtcat caacagccaa ctccagttta tactcagcct gtttgttttg caccaaatat 115920
gatgtatcca gtcccagtga gcccaggcgt gcaagtaagt catagaattt gatgttcact 115980
tagcctcccc aattgtttgt atctgacacc aagcactctt taggttttca gtgacttgag 116040
ggtgtgatgg ttatgcatat gcatttgaaa cagacaggca tgcagagatt cagtgtgttg 116100
ttaagtatga ggacctaaat ctgagaatgt tttctgtgaa aaagatggtt tagatttact 116160
gtagtttggg gtttgttcct tttagctgtg ggtatgatct aattttttaa tgactaatgg 116220
agaatcagga aaccttctca tgcctagctc tctagcaata taaaactaag agtgacagaa 116280
taccttgtta ttatcatagg tgcctaatgt taattttttt tttaattctc tcaagccttt 116340
atacccaata cctatgacgc ccatgccagt gaatcaagcc aagacatata gagcaggtaa 116400
aggtgagaat aatcctgcct gtgtttgctt gtagtttgca tgctgcatga attgagtaac 116460
taagtttata atgaataaat agttgtagtt tagctctgac tttttgatga ggctatgcat 116520
tggcttttga tgaacaacat tacatagata ttcacatgga ttttatgaag aaaaacaggg 116580
gagaaaaaat gcccatcagt tgtgattata tagtatcctc ttcaaaaaga gtaattggag 116640
gcctggtgtg atggctcaca cctgtaattt tagcactttg ggaggccaag gcaggaggat 116700
tgcttgagct caggagccca agatcagcct ggacaacaga gactttgtct ctactaaaat 116760
tcaaaaaaat tagctgggca tggtggcata tgcctgtagc cccagctgtt tgggggactg 116820
aggcgagagg atcacttgag cccaggaagt agaggctgca gtgagctgtg attatgccac 116880
tgccctccag cctgggcgac agagtgagac cccgtctcaa acataaatac tggctgggca 116940
tggtggctta tgcctgtaat cccagcactt tgggaggccg aggtgggtgt atcacctgag 117000
gtcagtagtt tgagaccagc ctggccaaca tggcgaaacc ccatctctac taaaatacaa 117060
aaattagccg gacatggtgg cacctgccgc ctgtaatccc agctactagg tggggctgag 117120
gcaggagaat tgcttgaacc cgggaggcag gggttgcagt gagccaagat cgtgccactg 117180
cacttcagcc tgggcaacag agtgagactc catctcaaaa caaacaaaca aacaaaaaac 117240
aaacaaacaa aaaaaccaga ctaattggct ggacacagtg gctccatgcc tgatatccca 117300

```
gctggaggat gacttgaacc catgagttcg agagcagcat gggcaatata gtgagaccct 117360
atctcaaaaa aaaaaaaaaa agttaattcc aaagcttttt gatctgaaat ctgatttaaa 117420
tctgaactta aatttgaaga agagggtttg ctagattaat ttactagatt gctaaccttg 117480
ctttatatat acctacagtt atttccccaa agccagaatt tcttttgaag cagaggggca 117540
actaacttca accaatgtta agatcctatt agaaggatgt ttcggctagg cttggtggct 117600
cacgtgtaat tccagcactt tgagaggctg aggtgggcag atcacatgac cgggagtttt 117660
aagaccagcc tgggcaacat ggcaaaaacc tatctctgca aaaaaaaaat agaaatctta 117720
gccagccgtc atggtgtgct cctgtagtcc tagctacttg ggagactgag gtgggaggat 117780
caattgaaac cagaaggtcc aggctgcagg gaactgtgac tgcaccactg ggctccagct 117840
tgggtgaaag agcgaaaccc tgcctcaaaa agaaaaataa gatggatgtt tctgcattaa 117900
aattagggag ttgtcgtata atgtagttgc ataaactagt attctgtgct tgtgtggtta 117960
aagagccttc gtagaaaaaa tcccacattt ttcttaaaag gaaatctttt ggccaggtgt 118020
ggtggctcac atctgtaagc ccaacactct gggaagccga ggtgggcaga tcacttgagg 118080
tcaggagtac aaaaccatcc tggccaacat ggtgaaaacc cgtctctact aaaaatacaa 118140
agatcagctg ggcatggtgg tgcgtgcctg ggtgacagag cgagactccg tccaaaaaaa 118200
aaaaaaaaaa aaaagagttc ttttaatgtt ggaaaatgct aaagggtttt tttttgccca 118260
accagttaat ttagagtgat taactgctat cagttgagaa actatagaaa gtagaataat 118320
ttatacagaa aagacatttc tcagtgccca ataattgcct ttctgacata aagttttcat 118380
ttttcctgaa ttaataagat ttcctcaatg tgtttttttg ggtgttttgt gtgtgtgtgt 118440
gtgtgtgtgt gtgtgtgtgt gtgtgtgtgt gtatgtgttt gatacagggt cttgctttgc 118500
tgctgaggct ggaacgcagt ggcgctatca tggctcaatg cagccttgac ctcctgggct 118560
caagcgatcc tcccttctca gtcccctgga tagcgggggc tacaggtgca caccaccaca 118620
cctagctaat ttttgtattt tttgtagaga tgggttttgc catgttgcct aggctggtct 118680
caaactcctg ggctcaagcg atctgcctgg ctctgcttcc caaagtgcct gcgcccagcc 118740
aattttctcc atgtttgacc taattgtgat ttcatagatg ttaactaaaa ctcttaattt 118800
tcgttttctc agtatgctat tttttttttt tttagccttg gaacatatga acctgttgaa 118860
agaactctgc ctgaaataat gtaatcaaat tatagagttt aatcttattt tgagggcctt 118920
tagaaattct gagaagaaag tgggtttttt tttttactgc cattttaatg tagtgttaag 118980
gtgttcatgt atcaccagca ggtgtagctg ttttcaatga ttacttaaaa caatgcaatg 119040
ggaacttttt gttgtcatta aaatataaaa ggttactgta gtaagagcaa gcatgacagt 119100
ttggctatct gatgggagag tcacattcta acttcaggag gtactgtctt tttaatagaa 119160
atgatatact cagagtctgg gcacggtggc tcacgcctgt aatccagcac tttgggaggc 119220
cgaggtgggc agatcacgag gtcaggagat caagaccatc ctggctaata cagtgaaacc 119280
gtgtctctac taaaaataca aacaattagc tgagcgtggt ggcaggtgcc tatagtccca 119340
gctactcggg aggctgaggc aggagaatgg catgaacctg ggaggcagag ctggcagtga 119400
gctgagatgg tgccactgca ctccagcctg ggtgacagag cgagactccg tctcaaaaaa 119460
aaaaaaaaaa aaaaaatagt agagaaaggg ctttgccatg ttggccgggc tggtcttgaa 119520
ctcctggcct caagtgatcc acctccctcg gcctcccaaa gtgctgggat tacaggtgtg 119580
agccactgct cctggcctga atataccact tttacctatc atcagttgat gaacatttgg 119640
```

attatttcct ttttctggca atgagtaatg cttttgtgga ttttcatgta caaattttca 119700
tatgaggctg ggagcagtgg ctcatgccta taatcccagc agtctgggag gctgaggtgg 119760
gcagatgact tgaggtcagg agtttgagac cagcctggcc aacatggtga aatcccatct 119820
ctactaaaaa tacaaaaatt acactggcat ggtagcgtgc acctataatc ccagctattc 119880
aggaggctga ggcaggagca tcagaatcgc ttgaacctgg gaggcggagg ctgcagtgag 119940
ctgagatcac accactgcac cccagcctga gtgaaagagt gagtctcaaa aaataaaaaa 120000
taaaattttt tttcatgtgg ccttagattt tcatttctcc taaagtagaa atgctgtgat 120060
ggaactgcca aacttttcca aagcagctgc atcattttgt atttctacca gtaatgtaca 120120
agtgttccag tttctccaca tcctcataaa taaccgatat gtctttggtt tgggttatgt 120180
ccattctagt ggttatgaag tgtcattgtg gttttttgtt tttttgtatt gttttgagat 120240
cgtgcccagg ctggagcaca gtggcacaat ctcggctcac tgcagccttc gcttcctggg 120300
ttcaagcaat tctcctgcct caccctccca gatagctggg gctgcaggca tacgccacca 120360
caccaggcta atttttatat tttttgtaga gatggagctt ctccgtgctt cccaggctgg 120420
tctcgaattc ctgagctcaa gcgatccccc tgcgtcagcc tccagagtag ctggggttat 120480
aggcgtgcac caccgcgctc ggcccatttt tgtattttta gtagagatgg aatttcacca 120540
tgttggccag gctggtcttg aactcctgac ctcaaatgat ccgcctgcct caccttccca 120600
aagtgctgag attttagacg cgaaccacca tgccctgact ataggttatc tttttacttg 120660
cttgatggtg ttctttgtaa cacagttttt aattttgatg aagttcaatt tatctgtttg 120720
ttttttcttt tgttgctgtt gctcctgatg tcatatcaga caaagcattg cctaactcaa 120780
ggccacagag atttactcct atgaaacgcc tataaaactc ctatgatttt tatagtttag 120840
ctcttaacat ttaagtctac aatctctttt gagttaattt ttgtgtatga gatgagagta 120900
gtggtccagg tttttccttt tgcttgtgga tatccgttgt ccccacctca tttgttgaaa 120960
agactattct ttcctcttaa attgtttgtt tgtttattta tttttgagat ggagtgtcgc 121020
tctgatggag tggcgctaac ttagcttcac tgcaacctcc gcctctcaga ttcaagcgat 121080
tcccctgcct cagcctcctg agtagctgga attacagggg tgcgccacca cacccagcta 121140
atttttgtat ttttagtaga gacggggttt taccgtgttg gtcaggctgg tctcgaactc 121200
ctgatctcgt gatctgcctg tctcctggca ccctgggagg ctgagaggct gaggtgggag 121260
gatcacttga gctcaggagt ttgagaccag cctgtaccat tatgcctggc taattttaga 121320
atttatctta aagtataaaa tgtgaatcca atttatcttg ttctaaatga ctatccaaaa 121380
tgttttaacc agttttatta gtctgtaatt tacatacaag aaaatgctca tctttttatg 121440
tttacatttt aatgagtttt gacaaatata tttgctcatg taactacttg cttcatcagt 121500
gaagatggaa aacattgtgc ctgttcctct tctctgtcca actgtacttt attaccacta 121560
gctccagtta accagtaatc tgccttcttt tactatagat tagatttatc ctctttagat 121620
ttctttttct tttttttttt ttgattaggt tttttttttt cttttttttac gtaaaaaaat 121680 cttttttttgg agacgtctca ttatattgcc caggttggtc tcgaactctt gagctcacct 121740
cagcctccca gagtgctagg attacagatg tgagccacct cagccagccc ctagattttt 121800
tttttttttt taataaatgg aatcaaacag cgtgtaacag aggtgttcaa tcttttggct 121860
tccctgggtc atattggaag aagaattgtg ttgggccaca cataaaatac agtaacacta 121920
atgatagctg atgaacaaaa caaaaaaaaa tagcaaaact tataatgttt taagaaagtt 121980
tatgaatttg tgttgggcca cattcaaagc cgtcccagga cgcaagttgg acaagcttgg 122040
tatataattt catatgtgtg tcctaaacag tgtagtaatt tgaatttcat gttagtatca 122100
gcttattcct ttttgtttgt ttgtttgttt ttgagatgga gtcttgttct gtgtcccaga 122160
attggtctgc aattccactg cctcagcctc ccaagtagct gggattacag gcacgtgcca 122220
ccacacctgg ctaattttg tctctctctc ttttttttt ttttttttt ttttttagca 122280
gagacgggat ttcaccatgt tggccaggct ggtctcaaac tcctgacccc aaatgatcca 122340
cctgccttgg cctcccaaag tgctgggatt acaggtgtga gtcaccgtgc ccagccagct 122400
tattcctttt tattgctggg tagcatttca ttttatgatt ataccacagt taatttaccc 122460
attactagtc gatgggcatt tgagttattg ccagcttttg gctattatga atgaagctgc 122520
tgtgagcatt tgtgtacaag tgtttgtgtt tttatttctt ttagttaaat acctagaatt 122580
ggaattgctg aggtatggta agtgcatatt tcattttttt aaaaaattta ttttattttt 122640
tatttattta tttttttga gatgaagtct cactctgttg cccaggctgg agttcagtgg 122700
cgtgatttca gctcatggca acctccctgt cccgggttca agcaattctc ccgcctcagc 122760
ctcccaagta gctgggatta caggcgcgca ccaccatgcc tggctaattt ttttgtattt 122820
ttagtagaga cggggtttca ccacgttggc caggctggtc tcgaactcct gaccacaagt 122880
gatccacccg ccccagcctc ccaaagtgtt gggattacag atgtgagcca ccacacactg 122940
cctggtaaat acatatttca attaataaga aactagcaat cttctaaagt gattgtgtca 123000
ttttacattc caactgatca ggtacatgtg taggttccat gtgttctgca tccttgccaa 123060
cacttggtat tgtgttatct ttttaatttc aacaggtcta atgggtgtct tatggtatct 123120
cattgtgatc ttaaatgtac atttctctga tgatgactga tccaggagca cctcatcatg 123180
tgtgtgtttg ttttcagctg tcaacctttt tttagtaaat ggttcaaatc ttttttccat 123240
tttatttatt tatttattta tttgatggaa tctcactcta ttgcccaggc tggaacgcag 123300
tggtgccatc ttggctcact gcaacctccg cctcccaggt tcaagcaatt cttacgcctt 123360
agcctcccaa gtagctggga ttacaggcat gcgccaccat gcctggctaa ttttgtattt 123420
ttagtgtagg tggggtttca ccatgttggt catgctggtc tctaactcct gacctcaggt 123480
gatctacctg cctcggcctc ccaaagtgct gagattacag gtgtgagcca ctgcgcctgt 123540
cctaataatt tctttttgtc tcaatgtttc tgcctgggtg cactggctca cgcctgtaat 123600
tccagcactt tgggaggcca acctggatgg atcatttgag ccaacagttt gagaccagcc 123660
tgaggaacat gacaaaaccc tgtctttgca aaaaaaaaaa agaaaaaaga aaaattagcc 123720
aggcacagaa gcgcattcct atggtcccag ctacttgggg ggctgaggtg ggacaatcgc 123780
ttgagcgagg ttgcgggggt ttggagggcg atggaggggt gatcgaggtt gcagtgagct 123840
gagattgcac tactgcactc cagcctgggc aatagagcca gaccctgtct cacaaaaaaa 123900
agaaaaaaaa gtcatgtttc ttttcttact gtgaaaataa agttactact tttagtaaat 123960
tattttaagt tatttatata ttctggttac aagtcctttc tcagaatatt gtgaatattt 124020
tctcccagtc tgcggttttt tttgaagagc cagtattgtt aattttaatg aagccttatt 124080
tatcaagctt ttctcttaag gttcatgctt ttttgtatca taataagaaa tcttttacgt 124140
accctaggtt atgaatgttt ttatggttag gtatatggtt gatttcaggt taggttttgt 124200
gtagggtgtg atgtaaaggt ctagcttcat tttctccacc ataaatattt actcggtttc 124260
tctggcacca gcctctgttt tccattggtg gctttatttt ttttctgttc ttgaaacaag 124320
agtctcgatc ttgttaccca ggctggagtg cagtagtgtg accttggctc actgcaacct 124380

```
ccacttccca gggtcaagcg attctgcctc agcctctcga gtagctagga ttacaggtgc 124440
ccgccactac acccagctaa tttgtatttt tttttttttt ttttttagta gagacagggt 124500
ctcaccatgt tggccaggct agtctcgaac tcctgacctc aggtgatctg ctcatctcag 124560
cctcccaaag ttctgggatt acaggcatga gccactgcgc ccagccatag tagctttatt 124620
gaattcagtt gactgtattg tatgtgtgtc tatttgtgaa ctgttttgtt gtattgatct 124680
ttgtatatat ccttatgcca attctctctt tattgctgtt actttgtaac caacctttaa 124740
gttcatatga gtctcccagt tttattctcg tcaaaattac tcttattctg cgttctttga 124800
atttgcaaat aaattttaga atcagcttgg gattgtgcac tgaatcttta tatcagttct 124860
gggagaaata tcttaacaat atggaatctt cattgaggtc atcatatact gctccattta 124920
tttaagtctt aagtttcacc agtgttttct agttttcttt gtatcagttt tgtgcctgct 124980
ttcttaaatt tatcccttaa tatttcatct gttttgtgct gttgtgagtt atattttaaa 125040
aactttcaac gtttgtttat tcgtaaatag agatgcactt gatttttgaa tattgacctt 125100
gtgtcttgat gtgttggtaa acccactgtt tctggcagcc ctttaagact taaacataca 125160
atcatgatct aatcaccatg ttggtgtttt tgggtttttt ttttttgtct tattgtactg 125220
gtgcattact gaaaaaggca tgagattttg ccatgctccc atttttaggg gtgagacatt 125280
gtctttcact attaagcata cagttaggtg ttacttcagt tcctaatttg cagaggtggg 125340
tttgttttct ttttaatcat gaatggttgt tggattatgt tcaaatactt atcatctact 125400
aagtatatca tattgaccag gaacagtggc tcatacctgt aacctcagag ctttgggagg 125460
ccaaggcagg aggatcgctt gaggccagga gttcaagacc aacctgggtg atgtaggaaa 125520
accccatatc tacaaaacaa tttaaaaatt tgctgggtgt ggtggcacac acctgtagtc 125580
ctaactactt gagaggctga ggaaggagaa ttgcttgagc ccagtagttt aaagcagcag 125640
tgagctgtga ttgtaccact gtactccagc ctgggtgaca gaaggagacc ctgtatttaa 125700
agtgtgtgtg tatgcgtgcg catagatgga tagataataa tgtaattcca ttatggtcat 125760
acaaactgat atgaaatgcc attttatcat ataacaagtg tctttttgtg gttgaatttg 125820
tttctggatt tttcactctg cttcactaat ctaataggac taccttctca tccactcact 125880
gccaacattg attttttttt tcagattacc ttgaattttc tgtttatttt tccatatgaa 125940
ctctataatt aacttactac taaaaaaatc agttgccttt ttaaaaccaa ctgatcttta 126000
aaatatatct tggctgggcc cggtggcagg cacctgtaat tctagctact tgggagactg 126060
aggcagaaga attgcttgaa cccaggaggc ggaagttgta gttgagttga gattgcgcac 126120
ctgtactcca gcctgggtga cagagcaaga ttccctctta aaaaaaaaaa aaaaaaaaag 126180
aaacagaaaa gataaatctt tttacaataa tttgttccaa ttagggtcca agtcaggctt 126240
gcaatttgga tttgtttata tgttgaagtc tttttttttt tttaattgtt tcatattgtg 126300
gtaacttttt tttttttttt ttgagatgga atcttggctc tgtcacctag gctggagtac 126360
agtggcacaa tctcaactca ctgcaacctc cccctctggg gttcaagcaa ttctcctgcc 126420
tcagcctccc aagtagccca gccttttttt tttgagacag agtctcgctc tgttgcccag 126480
gctggagtgc agtgatgcga tctcggctca ctgcaagctc cgcctcttgg gttcatgcca 126540
ttctcctgcc tcagcctcct gagtagctgg gactacattc gcccgccacc acacccggct 126600
aatttttttg tatttttagt agagacaggg tttcaccgtg ttagccagga tggtatcgat 126660
ctcctgacct cgtgatccgc ccgcctcggc ctcccaaagt gctgggatta caggtgtgag 126720
ccactgcgcc cggccttgta tttttaatag agatggggtt tcaccatgtt ggccagcccg 126780
```

```
gtcttgaact cctgacctca aatgatccac ccgcctcggc ctcccaaagt gctgggatta 126840
caggtgtgag ccatcgctct cagccttgcg gtaacttttt attacgaatg tattgagaca 126900
ttaataacct aggccagtca tgtttcatcc ctacccattg tctcttaaaa gctttgagtc 126960
cactggatta ttctgaagca aattctagac attgcatcag tttatccacc aacattttag 127020
tgtgtatctt taagttggtt ttggttttgt tttttgtttt tgagatgggg tctggctttg 127080
ttgcccaggc ttggagtgca gtagtgcaat catagctcac tgctgctgcg aattcctggt 127140
ctcaaaggat cctccctcct cagcctctca agtaactgtg actacaggca catgccacct 127200
tgccagcttt tcttttcttg tcttgtcttt cttcttcttt gtttttttgt ttgtttttg 127260
ttttttttg agacagagtc tcaccatctt tctatcttgc ccaggctagt cctaaattcc 127320
agggcttaag ttatctttct acctcagcct cctaaagtgc taggattaca ggccagcact 127380
ttaggaggtg ctggatgagc catcacaccc agccaagtca taggtttttt tgtttgtttg 127440
ttttttgaga cagtgtctaa ctctgtcacc caagctggag tgcagtggca tgatttcagc 127500
tcagtgcagt ctctaccaat tgggcttagg tggtcctccc acctcaacct cccaagtagc 127560
tgggactaaa ggtgcgcgcc accatacctg gctaattttt gtattttttg tagagacagg 127620
gtttcgaatt cctgagctca agcagtctgc ctgccttgac tcccaaggtg ccaggattac 127680
aggcatgagc cactgcactc agccctcaca gttttaatta cagtttttcc cttagttttt 127740
gtcttgttca tatccagctt gtcttgtatt tttttcccac gatctgaatt ttgctgactg 127800
tatccctgtg ttgatattta aagtagactt ctgtcccctg taatctttgt aaactgatag 127860
taaataatga aggcttgatc agattgggtt tttttttttt ttccccaatg tttcacagat 127920
gtgtgtactt tcagtgagga gtcatgtaat cagtcttttt cctgatagga gtagtcagtg 127980
agttcctaga tgttttatct atccaggaga taatatgtcc ctttagcgcc ttaatttttt 128040
tggtgtgttt tttagcagcc attgatgata attgtctagc ccaagatcag ttatttcctt 128100
aggggttgta aaatggtgac attcttttcc tttcatccct tcttcaatta ttgcctggaa 128160
tatttctata aagaaaaact ttcccatatc cagctgtttg gttaccctga ggtatagctt 128220
tcttaggaaa agtaatttaa aatgttaatc atttcccttt ttaaggcagt cttcaaaata 128280
atgagttggt tttctgttat cctccaaagg taaccagtga ggtggttttt ttgtcgttgg 128340
ttcttactat cagtataaac ttctggaatt tttttttttt ttttaatttt ttggagacaa 128400
ggtctggctc tgttacctag gctggagtgc agtgggatga tctgggcata ctgcagcctc 128460
aacttcccga gctaaggcaa tccccccacc tcagcctccc aagtagctgg gactacaggc 128520
aagcaccacc gtgcctggct taatttttgt atattttgca gagacagggt ttcaccatgt 128580
tgcccaggct ggtgtcgaac tcctgagctc aagcagtctg cctgtgtcag cctcacaaag 128640
tggtgggact acaggcatga gccaccatgg caggccagaa tcacaataaa cttataaatt 128700
aacttgagaa gaaatgattg atgtcttcat gatgttgagt cttcctgttc aagaacaaag 128760
tataccttca atagcatatt aaagtttatc cttggctgga tgcagtggct gacgcctgta 128820
atcccacctc tttgggaggc agaggtgggc agatcacctg aggtctggag ttcgagacca 128880
gcctggccaa catggtgaaa ccccgtctct actaaaaata ttttaaaaaa agtattagct 128940
gggtgtggtg tgcacctgta gtcccagcta ctctggaggc tgaggtagga gaatcgcttg 129000
aacccaggag gcagagagtg cagtgagtca agattgcacc actgcactcc agcttgggca 129060
accgagcgac actctgtctc aaagaaaata aataaataaa aataaagttt atctttaagg 129120
```

```
ttttgtacat ttttttcagt gtatgcctta ggtaggttct tttttaatgt tagtgtaacc 129180
cagggacttc tcttccattg catcttctaa gtaattactt atgaagtacc atatatgaag 129240
gctattgctg tttatatgtt agtttttacc ctgctccttt actaaattcc aatcctttga 129300
ggtattggat aaaaatattt ttagcatttt tcaaataaca ggcagagtca agggcttggt 129360
ttcttttctt cccctcctgt cccctaccct cccctttttt gagacagggt ctcacttctt 129420
cgccgaggct ggagtgcagt ggtgcagtta cggcttaccg cggcatctgc ctccctggct 129480
gaaaagttcc tcccacctca gcctcctgag tagctgggac catagatgca cagcaccgca 129540
gctggctaat atttttgtat tttttgtgga ggcagtgtct ccccatgttg cccagggtgg 129600
tcccaaactc atgagctcaa gcagtccgct cgccctggcc tcctaaagtg tagggattat 129660
aagcgtgagc cactgcgcct ggcctgggga tcatgtttta acatgagaat tagtggagac 129720
aaacacatga tatctaaata atagcaccat agtatacttg actagctttt taattatttt 129780
ttaaatatac aggaaggtaa taagtaacaa agtaataata gtgaatagtt taagctcagt 129840
tagcataatc gggcaaactt tcatttgata aaagtgataa gtagttttca gtggcttttt 129900
tgtttaccag aaggaggtgg tttttaaata cgtgcatcca agataaaata taaaaaaatg 129960
ttcaggtttg ctttcctaca tagataaaat aatatgtaac tagctctccc aaatttcagc 130020
aacagttagt gaatgtttag ccacaaattt gcagttaatt atataatcag ttcttaggat 130080
tttatgaaca agttctatat tctttgtgcc ttatacctag ttgtaagcag tcattccaca 130140
attattttcc tgaagtggct tggttaatgc cacaccagaa acaggtcaca gacaatagtg 130200
ctgtaagaaa tgtgtgagga aagaggcaca tgggaagtag ctagctcgtg ctggaggaac 130260
tggaaaaaaa cctcacatgg gagatgacag ttgagctgaa ttcttaacta gagttgtaac 130320
agggcgaggc ccttacatgc agaccacctg tgtggattaa gataagacat aaagtaatct 130380
tttaaaagaa ctattattta gaaacctggt atatgctaca tggtgctgtg ttatactggg 130440
tttgagaaag aatgggaagt gttacaagga ttcagtggtt ggaaattaag gaagatagaa 130500
agttagtgtt ggatctgttt tggctctttg gtcatgcctt tgtttttctc aaaatgaatg 130560
cagtgcccgt cccagaaaat accatatgag aagcgatttc ataatgctgt gagagtctgt 130620
tacagggact tgatcaagtc tgagggccat gagagaaagt ccctctgagg aagttgcttt 130680
caagctgaca cctgaaggat gaagcagaat tatcccagct gggatttggg aactggtgtt 130740
tgaggctgag gactagcatg catgatagga aaataaccca gagtggcaga agtgggagtg 130800
gtatgagatg gcatcagaga cgcagattca gggtcaaatc attcagagcc tcctagacca 130860
tgtgaacaca tgtattatgc tgtggagata ctgtttaata ggcagtctgc tttttttct 130920
gcagtaccaa atatgcccca acagcggcaa gaccagcatc atcagagtgc catgatgcac 130980
ccagcgtcag cagcgggccc accgattgca gccaccccac cagcttactc cacgcaatat 131040
gttgcctaca gtcctcagca gttcccaaat cagccccttg ttcagcatgt gccacattat 131100
cagtctcagg taaggctggt aaggcctaac tcttaatttt tgtaccatat aaaaaaactt 131160
ttaatatggt aaagggattt tcctttataa tttttgcttt tgtgtgatgg tagggtagat 131220
agctaaggac ttggggaccc ttttcaatat atattcgaag gttactgatg attgtaagag 131280
gttcagagga aacagccaag aaagatttga gagtttacag ctgtttctgg aaatctggaa 131340
accatggagt taaaaatctt aactaaagtc tgcttggctc tatttgcagt gttaatgtgc 131400
tttctttatt ttttgtttga acacagcatc ctcatgtcta tagtcctgta atacagggta 131460
atgctagaat gatggcacca ccaacacacg cccagcctgg tttagtatct tcttcagcaa 131520
```

ctcagtacgg ggctcatgag cagacgcatg cgatgtatgg taggaagcac tttgtttgtc 131580
tcttccagtg tgtgtgactc ttcttaattt aagtttctga aaacatactc tatctaagaa 131640
taacctgacc ttttatgaca ttgagggtca agaatctgaa ggaaaagatg aacccatttc 131700
tttgcctgac ttgctttata acttttggca aatagtttct acttctgtac ctggtcttca 131760
gatctctttc ctgctttaac taaaatgtaa tgatgtatat aatggcaaag catctttgtg 131820
gagaaaggta cctttctcct cttcctcatc aatattatgc tttggtatat cctgcctacg 131880
acatgcaaga gaattttata ataataaaag cataaaggtg ttctccagca tgaaaacatt 131940
ttgcttcact acttgatctg agggtcactg gcattacata ttttttttgc tgtttgttat 132000
aatgataata ctatgtttct acatcatgct gtattttaat ggttgaatat tatgtcatat 132060
tagatatatt ttagacatga gtcacacttt aaatataacc aatgtgaaca gaatgctgaa 132120
atgaaaatga gaagtatttt atgtaaaact aagcagtatt tatatgtgag aataataagc 132180
aaaaaaaccc atcttcgttt tgtgactaaa cagagaaatt tgtgtagatc aacttagcag 132240
ctgtctaaag taccaaaata atagattttt cactgttgat aatttaaaat aaaatgtcca 132300
tttgtatatc ttatgataca gaattaatgg attgcttcaa atgtttttca gaatatgttt 132360
ttaaatagta ctgatttcat taagatgttt tgttctgaat atttctgaga actaccgtag 132420
tgtcgtttag ttttcctatt tgcgtttttg gttgtttgga gtaggggata attttggttt 132480
attcatacag ttgaaaagtg tactgctatg agaatgagat tatggttaca tgtaactaca 132540
tgggcatttc atttttaaag cctctttgaa ctttttgaaa tactaagaat ataaaatttt 132600
tattttttaa gtttagatgt cctgaacgag tatgtttagg caaaattgag ttatttaaga 132660
atttataggc tgggcgcagt ggctcacgcc tgtaatccca gcactttggg aggccaaggc 132720
tggcggatca tgaggtcagg agatcgagac cagcctggcc aacatggtga aaccccatct 132780
ctactaaaaa tccaaaaaat tggccgggtg tggtggcatg tgcctgtagt cccggctact 132840
tcggaggctg aggcaacaga attgcttgaa cccgggaggc agaggttgca gtgagccgag 132900
atcgcgccac tacactctag cctgagcgac agagtgagac tccatctcca aaaaaaaaaa 132960
aaaaaaaaaa gaatttacag atttctggca aaccttcttc ttgagacatt actacttttc 133020
ataccacctc tgtccttttt gaagaataaa agttttaaca ttccgtaggt taatgagaat 133080
aggacttggg cagcagcaat catccttcct gtcacctgta acccacagct tatgctttct 133140
tcctggaggt tcttgtctgc cacaaaggct cactgctgat aggaatttgt atatgatcaa 133200
aggtgtttag ttttataaaa cagttaagtc cagtcttaat tttccacatt atcactttca 133260
attttgtatt gtggattacg cattttaaat aaaaaattgt gtgattgcta cattttggaa 133320
aacatttttt tcaagaggcc catccgtaat ttaattgtaa aagatactga caaactaact 133380
tggtttatta ttttggttat gaccccgtca tttgacttgt ctttagttgt cttaacgggg 133440
actgaatatg cgtgcaaagg cacgattgat ttatcatgct ggcttttatg caacttgtat 133500
atattttaac aattttcctg tttgctaaag gcttaggtta aaagttcatt atgattgttt 133560
atacatttct ggtgaataca tcatgattta acaagtggaa agaacatctc tttccttcca 133620
ttttctggca tactcccctt ggaatcagat ctgaaacttt taagctaaaa tttccattgc 133680
atttggagag tagttatttg tgtatgcatg cttttgagac attgtagcaa taatactgta 133740
atgttgagcc gaatctttct cctcattgtg ttcattcact gccaacatct ggcttcatct 133800
tttggatgaa tgttcattgg ttttgaaaca gcctataggg taaatactgt gtttgaggta 133860

```
cagatgattt tcataactac ttcctagaac atgtccattt gaagagcagt ggggccttag 133920
accccaaagt ccatttatgt gtgggcaaat aggaaatgtt gcaaacaaaa caaagcacta 133980
gatctaatgt ccagtgaaat ctggaatgaa ctagtcatta gagccggttc tttcatgcca 134040
ggaaaaagtt actcagccaa atctgaacta ctctcctgca gtttacacag gtggtattta 134100
attgctgtct gtatggaggc aggctaggag caaggctgtg gacttgttgt gattgtcact 134160
agttaatcaa gattcccttt gtggtgctta agaccctaaa aaggacacta ggagctgggc 134220
atggtggctg acacctgtaa tccaagaact tggggaggct gaagtggagg atcgcttagc 134280
ccaggtgttc aagaccagtc taggcaagat ggcgagatcc catctctacc aaaaaaaaaa 134340
aaaaaaaaaa aaaaaaaaag cccagtcatg gtggcacatg cctgtagtcc cacctacaca 134400
ggaagctgag atgggaggat cacttgagtc caggactttg aggctacagt gagctatcat 134460
ggcaccactg taatccagcc tgggtgacag agcaagaccc tgtctctatt taaaaaaaag 134520
aaaacataag aaagaattgt tttgttctat gccatcataa gccataattt aatctgctta 134580
agcatgttct tcattaaatc tgcagtgatt tatttgaatt attagacttt caaagcctta 134640
ttatatcaaa tataaacaaa atttgaagta cattcttata aactacaaca aacttacata 134700
gaagtgttaa ttttatactc atcttccctg aacaatttat attttataaa tatattaaat 134760
atattgtaat aaattttctc aaaggaacca aatactttga gtatgaattg tgcttttctt 134820
tttaagctac atcatatcta ggtttttaaa acatttaatg caaacagaag aacatgcacc 134880
cagatgttgg tgacaatttt atgtcacctt ttctcattca ttaattgtta tagccatagc 134940
caaaggcatt gaaaacatag gaccactaat gactgcaaaa tgaaatcctg attattgttt 135000
ttaaattttt agtatgttta atacacatat gctaacatta ctgaacagtt aaatgataaa 135060
ataggataat tattttattc taaaaaagta ttgaccttga cctctttcta gctatcttag 135120
aaagggcttt tgtcaaaaac cttatctctt tgatgtctct ttttttgaga tggagtctct 135180
ccctgtcgcc caggctggag tgcagtggcg tgatctcagc tcactgcacg ctccgcctcc 135240
tgcgttcacg ccattctcct acctcagcct cccgagtagc taggactaca ggcgcccgcc 135300
accatgcccg gctaattttt tgtattttgt ttagtagaga tggggtttca ctgtgttagc 135360
caggatggtc ttgatctcct gacctcgtga tccgcctgcc tcagcctccc aaagtgctgg 135420
gattacaggc gtgagccact gtgcccagcc tctttttttt tttttatttt ttatttattt 135480
tttatttttt ttttaatttt tgagaaggag tctccctctg ccacccaggc tggagtgcag 135540
tggcgcgatc tcagctccct gcaaactccg cctcctgggt tcaagcagtt ctcctgcctc 135600
agcctcctga gtagctggga ctacaggtgc ccgccaccac acctggctaa tttttgtgtt 135660
tttagtagag acagggtttc accatgttgg tcaggctggt cttgaattcc cgacctcagg 135720
tgatccaccc acctcagcct cccaaagtgc tgggattaca ggcgtgagcc actgccccgg 135780
cctctttgat gtctcttaat ctaacttcca tcattgcctc taccccatcc cttctaagaa 135840
gttactttaa ttttttttcc tctcacatct actctttttt tttttttttt tttttttttg 135900
aggtagtctc actctgtcac ccattctgaa gtgcagcggt gcgatctcag ctcactgcaa 135960
catctgcctc ccaggttcaa gcggtttttc tgcctcagcc tcccgagtag gtgggactac 136020
aggtgtgcgc caccacgacc ggccaatttt tgtattttta gtagagacgg ggtttcaccg 136080
tcttggccag gctgatctcg aacttctgac cttgtgattt gtctgcctag gcctcccaaa 136140
gtgctgggat tacagatgtg agccaccacg cccagcctca catctactct tctaatccat 136200
ctaattttgt tttatggtga tgcttttacc tttcagaaac agtaataata caacttttcc 136260
```

gactaactag agccattagg aagaattaga tccagaatcc ttttttgatt tgtttttggt 136320
agtttaatgc agataagtaa gaaaatatag ttaagttaaa aaaaaaaaaa atgaaaagca 136380
tccataatcc ctccacctga caactgcctt ttaacatttt gatgtgtatc cttccaggtg 136440
tatttaaata cactcaaata ccctacccct ttatgtagac atgttttaat aagaaataat 136500
attcatgttt atattcttgc tatgatccta aatttttgga tccattacta gataatcttt 136560
caggataatg acatttccat tagtaatgtt tttgcaaaat tgtgtgtcta ttgaattaaa 136620
cttgtaaaat agttttattt tggtacatga tttatatcaa ggttgttcag tagaatgcca 136680
tgttggtgtt tttattagat aatgatttta ttccttttac ttttaagcaa gtcagcatga 136740
caacttgaca cctaagtaca gaagaacagt gtcttccggt ttagtccttt cttttaaaat 136800
tctgtagcag tgtttaaagt gcttgtcatc tcttatgaaa atgaattatg catgaataca 136860
aaaagaaatt actaatatgt caacctttcc agaaaatttg gaaaatgcac acctcaaaag 136920
gctaatttac ctttctattt cccaaattca gcatgtccca aattaccata caacaaggag 136980
acaagccctt ctttctactt tgccagtgag ttgggttttt tatactaatt tttaattgta 137040
cagtaaaaca ctttttaaag gatacatgtt aagggagtag acttgttgaa caatattttc 137100
cttgtgccag tcaaattatt gaaagtactt atatatataa ataattcagt ttttaaaatg 137160
gaaataccca atttaagaag gctggagtta atgaaaaatg gagttgtttc agaaatcaat 137220
ttttgcatac caagcaaatg tgactgggaa atgcctaata ttttccttgt tagagaaact 137280
tcctaaacag ctttatacac acacacacac acacacacac acacacacac aaacacacac 137340
acccaagcca caagcttggt ataaatttaa aatgtttatt tatacacaca cacacacaca 137400
cacacacaca cacacacacc ccaagccaca agcttggtat aaacttaaaa tgtttattta 137460
tattctgata agatgaaatt tatgcctacc aggattttta attgaatagg attgatgaaa 137520
tactaaggga aaaacttttc agtcctgtgc atggctaaag gtttaaaata ctcaggaagg 137580
gccaggcacg gtggctcaca cctgtaatcc cagtgctttg ggaggctgag gcgggtggat 137640
catctgaggt cagcagttca agaccagcct agccaacatg gtaaaactcc atctctacta 137700
aaaaatacaa aaatcagcca tgcatgctgg catgcgccta taatctcagc tactagggag 137760
gctgagacag gagaattgct tgaacttggg aggcagaggt tgcagtgagc cgaagtcgtg 137820
ccactccact ccagcctggg tggcagagcg aaattctgtc tcaaaaaata aaatattcag 137880
gaagcagacc cctcaggata tcttgagctt aagcaagaga tcatgacctc tcaggtcatt 137940
atcttggaca gcacaggtcc cctctcccca cctggcaaaa agtacagaaa tagttgctcc 138000
ttcatggaga aagtctgggc agagctttct tctggaaatg aacttttaag gtacattttt 138060
cctatttgta gggcaatttg taaaaataag ggccggacgt ggtggctcac gcctgtaatc 138120
ccagtacttt gggaggccga ggtgggtgga ttgcttgagg ccaggagttc gagaacagcc 138180
tggccaacat ggtgaaaccc tatctctacc aaagcatggt ggcacgcacc tgtagtccca 138240
gctacttggg aggcggaggc acaagagttc catgaaccct ggaggtggag gttgcagtga 138300
gctgagattg taccactgca ctcaggcctg ggcaacagag agagactctg tctcaaaata 138360
aaaaataaaa ataaggctag tcttggactt tggtatttaa ataggaagga gtactaatat 138420
ttgtagaaat cctttagaaa tttgtgccat taatattgtc accttgtatg aaatgttgtg 138480
ttctagagga tattaaggat tcaaatttta tgttaggcac attttgagtt attttggggt 138540
gactcaatgt ctgactctac taaatgccat attagcattt aaaatgcatt tgaccttaaa 138600
tctttgttaa ttatgccatg acttggtatc caaaaataag ctgatacata catacataca 138660
tatatgtgtg tgtgtgtgtg tgtgtgtgta tatatatata tatgtatgtg tgtatatata 138720
atttatttgg tgctaggaaa tgttaaattt aatcctttaa tagatgctct ttaaaaagga 138780
gtcttgctgt atgtatatac tattaaaggg gaaactatgt ctgtgattgt agtgtgtaaa 138840
agatagtagg tgattttatt atgtactcaa tttgaggtct caaatgtagt tatcctcacc 138900
atcttactgt ctctgttagt agtttggtgt tgttttcctg gtaagtagct aaggtcctta 138960
atcattaaca cctaagcctt aattgcctta gcacaacttc ccctaaaagg gagtatcagt 139020
actttttaaa agaaactaac agttgggctg ctaatttaat ctgctgcttc atttccccct 139080
gttctaagcc attttatgat ggtttggtca agttgccttt tattcccctt ttagagtttt 139140
caactttcct tcacttccct ttttctgaat ttaacatcag atttacaagt tggaagattt 139200
tgttttgttt tataagtttt gcaatgctgg tgatctctta tgacttgtgc atccaaagtc 139260
aaaatgacaa aacctagtta caaattaaac acacagcttt ctgtacttaa tttgcttcag 139320
tgagatcaca gctgaggaaa ctagttctgg aatgtggtta gtgttattaa ggatttttga 139380
ctgatcatat gtttagaatc ttaaatattt atgtcaagga acactgagtg ggaaacttct 139440
ggactaggtc tggaccaaag aagcatatgt ctttgattat ctttaatcta aaagatttta 139500
tgaagactaa agttttataa atagaagttt aactgatgaa taaatcagta ttacaaataa 139560
aattaacttt atttttaacc tctctgggat ctttagccag aatgagcata tataacaaaa 139620
gcagtgaaat aatatgtgtg ggtcagaacc cactgccctt cccactccac tctccttttc 139680
cctgattctc ctgtgttttt tccttcttta ccttatcttg gttccttttt tttttttttt 139740
cttttgagat ggagtctcac tctgtcgtcc aggctggagt gcagtggtgc gatctcggct 139800
cactgcaacc tccgcctcct aggttcaagc aattctctgc ctcagcttcc agagtagctg 139860
ggattacagg cgcctgctgc cacacccagc taattttttt tgtattttta gtagagacag 139920
ggtttcacca tcttggccag gctggtcttg aactcctgac ctcgtgatca cctacctcgg 139980
cccctggttc ctttttttgtc tctcttgtct tccaagctat ttttttcctt ggcttttaaa 140040
ttttcttcct accctgcttt gtgtcactgt cacttaactg gcctatcaag gaaccgaact 140100
gtatttttgt tactagtatt gatttaaagt ataagtttca catttctccc aatttattat 140160
tattatttat ttatttattt gtttatttta ttttttgaga cggagtttcg ctcttgttgc 140220
ccaagctgga gtgcaatggt gtgatgtcgg ttcactgcaa cctccacctc ccgggttcaa 140280
gctattctcc ttccccactc tccctagtag ctgtgattac aggtgcctgc caccacgccc 140340
agctaatttt tgtattttta gtagagacag ggtttcgccg tgttggccaa gctggtctcg 140400
aactcctaac ctcaggtgat ccgcccgcct cggcctccca aaatgctggg attacaagcg 140460
tgagccaccg tgcccggctc catttctccc aatttcaaat tcaaggagga aaagaattcc 140520
tgattaaggt acttctttca gatcttttga gctagaacaa aaaaacaaag ggaaatattt 140580
ctaattaact ctttttaaat tttgtttaca acgtatgata catattttac acatcctttg 140640
tggtttttgt tcgtcttgtt tttaatcaat gccttgcaag tttaccggta tttaggtagg 140700
gaaaggattt tgtttttgtt tttttaaaca aagcctatgt acattcactc agcttgggta 140760
tttgtgctat gcatgcaaat tagctataga ttagaaaacc gtattatagt ctttaaatac 140820
tggtaaactt aaattgcaga gatgcctttt aaaaatgcat agtaaaaata tttcatcttt 140880
acttttctct tcaaatgatt ttaagatttt tacatttttc cagttgatga ataacttaaa 140940
ttatgagatt tcatgggcat aattattttc tatatttatt gttacttttt aatattctta 141000

```
atactttgct tagaaggtat ttaaaagtga aatttcaaac tttttagtac aaaatttctt 141060
gaataaataa agttacaaaa aaaaaacaaa aacctctgag attccgtact gtatctttat 141120
gaacctccat gaacagaatt tgggatttgg gaattgcttt tccttagaca gatttagatt 141180
gttacaaatg acatttttaa gaggctgggg tggcggtagg ggttagtgct aatggtttaa 141240
cagtagggga ccatggacaa ctgtagacat cactatccag tagaacattt tgtggctggg 141300
cgcggtggct cacgcctgta gtcccagcac tttgggaggc caagacaagt ggatcacctg 141360
aggtcaggag ttcaagacca gccagaccaa catggtgaaa ccctgtctct actaaaaata 141420
caaaaaagtt agccaggcgc gcctgtagtc ctagctactc aggaggctga cacaggagaa 141480
tcgcttgaac ccgggaggca gaggttgcgg tgagctgata tcacgccact gcactccacc 141540
ctgggcaaca gagcgagact ccgtctcaaa acaacaacaa aactgcactg tccaccgtat 141600
tagctactta gctacatgtg gctttttat tattcaaaaa taaattttta ggccgggtgc 141660
agttgctcac acctgtaatc ccaacacttt gggaggccga gatggacgga tcacttgagg 141720
ccaggagttt gagaccagcc tggccaacat ggtgaaaccc cgtctctact aaaaatacaa 141780
aaattagcca ggtaatccca gctactcaga ggctgaagca ggagtatcac tttaacccag 141840
gaggcggagg ctgcagtgag ccgagatcgc tccactgcac tccagcctgg gtgacagcaa 141900
gactgggtct caaaaataaa caaacatggc cgggcgcagt ggctcatgcc tgtaatccca 141960
gcactttggg aggccgaggc ggatggatca cttgaggcca gtagttcgag accagcctgg 142020
ccaacatggt gaaacccgtc tctactaaaa atacaaaaat cagccaggca tggtgatgct 142080
tgcctatagt tccagctact cggcaggctg aggcaggaga atcgcttgaa cccgggaggc 142140
ggaggttgca gtgagccgag atggtgcccc tgcactccag cctgggcaac agagcgagac 142200
tctgtcaaaa attaaacaaa taaatacatt tttaaaatga acgtaagatt tttacaagta 142260
caacaaactc aggttcgaaa tttacatcaa atcttttaga ccaagtcagt gcctatacaa 142320
cttggaggag ctggaagtaa acttaatgag tatgatgatg atggagggcc tgttaataag 142380
ccaccaagtt agaaaaaaag gactgtctta tagacttatg ggactgtgaa gctcaggaag 142440
gcttcatcgt ttgtacatca tttgttctag ctcccagaag acgttcacta ctcttaaaaa 142500
cattcagaga ctatgttgcc acagttttct tgttaaaata ttctggcata tgttaattcc 142560
tacagtctgg aaaattttcc cagtgtataa acaaagctgc tgtatccagt ctaaactgga 142620
tatgaaggaa tattaatgcc agctgtggca ttggcagtgg atgcacaggt gatcctagaa 142680
ctggctcttt gccttgccct ttcccctgct aagagatagc tttgcagctg gagacgtaac 142740
tgttagggct ggagagttgg tggcccttag ccctacaaca cctaggatta tagaactgct 142800
ccatgtgcct agcctaaccc tctgcacacc atttacgtgg aatataccca gagccgtcta 142860
tgctggtgac tcggcagcct tgcctaccag actgctggaa ctagggtgcc tcttcccaaa 142920
gctgtgcttg cttctctcac caatcagtcc tgcatatgtc tgtgtttgct aacacgttat 142980
atgaagaatg tggggaacta ttttggaatc atttctgtgt atgggcttat tatcttgagg 143040
gattttagga tttgtttctc aagagagggc tgggaactat accttgctag agttgtcttg 143100
agaacgctct attctcagct cattgcctcg tggaggttag ttttttatca tcggtgtgct 143160
gtccatagtc actggaagca gtgaacacat cctactctgc ttctgattct caacttactg 143220
tttttgaagc acatgaacag gccaggcacg gtggctcacg tctgtaatcc cagcactttg 143280
ggaggctgaa gtgggcggat catttgaggt caggagtttg agatcagcct ggccagcatg 143340
```

```
gcgaaacccc atctctacta aaaatacaaa aattagctgg gcgtggtggc acatgcctgt 143400
aatctcagct actcgggagg ctgaggcagg agaattgctt gaacctggga ggcagaggtt 143460
gcagtgagcc tgggcaacag agtgagtgag acttatatct caaaaaaaaa caaaaaacaa 143520
aaaactgaaa gacatgaaga aatggttttt gtaccaaggt ttggcccacg ctgagattca 143580
caaagaactg gctttcagtt cttatcttta ttttgattta aactggccca tcatgttgtc 143640
ctttgaagtt agtctagtaa atttctttcc aaagggctgg ggcactcaga agggagttta 143700
cttttctata tttatttcat aaagcaaaga tgggagatcc tccattaggg cttgggaaag 143760
taaactgagt ggcagaaggg ctcctgtgat tagctgagag agactgtggt ccttcggccc 143820
tgatgataga tccctggcct tgccacatac catacacagt gcccgcaccc ccatccccca 143880
ccacacccaa tatagtctgt gccctcagga cattgctcca gggcagtagc atggtgaggt 143940
tagcctgatg atggccttga gctaaagagt gtgcacctaa aatgcacttg tttgagtagt 144000
ttctgcctat gccttcaagt tgcctttttg ggaaaaccta gtgaccgtta agagtaaatg 144060
caaactaatt tgattttaat atcatatgta gagctgtatt atatgaacca aatgctagtc 144120
tgttaagcaa tagctacact tattttttca agacaatgga tggtttaaat ggagtcatct 144180
atagaaattg gtagtggcgt gagttatgca ttgtaaccat caagaaagtt cagttgatga 144240
agtgtagagg agcgatggag gttgtcagac atcggttgtg tacatgctcc tttttctttc 144300
actttagttt ccacgggctc ccttgctcag cagtatgcgc accctaacgc taccctgcac 144360
ccacatactc cacaccctca gccttcagct acccccactg gacagcagca aagccaacat 144420
ggtggaagtc atcctgcacc cagtcctgtt caggtaaggg caactcagag gtctgcatgg 144480
agtggcttct ttatcctagt atctgagtgc tttcttcagg tgccaggtat cgcatcgtca 144540
gaacacatgg catgtccacc ctcgtgaaga tggatacagc tgtgcccctg gggtggtggt 144600
tttaagaatc acatttaaag gctgggcgca gtggctcacg cctgtaatcc caccactttg 144660
ggaggccgag gcgggtggat cacgaggtca ggagattgag accatcctgg cgaacactgt 144720
gaaactccgt ctctaataaa aatacaaaaa aattagccgg gcgtggtggt gggcgcctgt 144780
agtcccagct tctcgggagg ctgaggaagg agaatggcgt gaacccggga ggcggagctt 144840
gcagtgagca gagatcgcgc cactgcactc cagcttggac aacagcgaga ctctgtctca 144900
aaaaaataaa aaattaaaaa aaatcacatt taagatacat gttgataata aggtgattgg 144960
ataagctctg gaaacttgca gtaatgaaaa atcaaattta acataaagtt cataaggcaa 145020
attcctattt gcttgggact ttttaatttc taaggtttat gtgatgaggt tattttccta 145080
tgagcttctt gaattatgtt tgctaatgga ggcagttaaa gatgtctttg atatctatca 145140
gttccctggg gcagtagtct tttttgactt tagtatgtat gctcagaagt ttctaactgc 145200
cagactgaga atcaggcttc tgtaccctag aaaggagttg tccagatggg aggcacctcc 145260
agccttgctc ttaccaccct gtacattctc ctgtactttc cagtgaccct catcataggc 145320
ccaagtgtgc aaagcttagc tttgtgggta tcccttggct gcttttcatt aaagaagttt 145380
tcctctcaat tctttcctgt cgctttgcag caccatcagc accaggccgc ccaggctctc 145440
catctggcca gtccacagca gcagtcagcc atttaccacg cggggcttgc gccaactcca 145500
ccctccatga cacctgcctc caacacgcag tcgccacaga atagtttccc agcagcacaa 145560
cagactgtct ttacgatcca tccttctcac gttcagccgg cgtataccaa cccaccccac 145620
atggcccacg tacctcaggt aataccagct ttagccaact ttctgtgaag gccaagtaga 145680
atgtgaaggt tatcagtaag cagctagagg ctctcccagc taggaaaccc tgtgtgtcat 145740
```

gccatttgcc tgtctccctt tccctctcaa atacacgtga tctggcccta agggaatgtt 145800
tgtgtggttt tgtcatggga tcagtgaagg tgctgattgg tcagtccttt agttttccaa 145860
ctgagacctt aaaaatatct ttgactctgg aatgcaaccc agtccttctt tcctttctgt 145920
gtctgctttg ctatgtctat atagcctcac tactatatat atgtgtacat atatattccc 145980
ctacacactt accttggaag ccaggcaggg atgatggcct tcacagagtc tcagctctcc 146040
gaagtgacta ccggggcctg tcaacttgat tgttactcac atgagttcca gacacatctc 146100
tccaattgtt ttccctggtt atccatatat ctgctttgac cataagttgt actcttgaga 146160
gggcttggcc ttggacattg gtgcagtgta actagaagct ggaagcaccc aggtggtccc 146220
atttttcttt aagagcagcc ctggaagcac tttggagctc acctccagtg taagctgcta 146280
caggtgaaag gtgtgcttgc catctcagtg gttgctgtct gcatcagctg ctgacaaagg 146340
tccctgcact ccagggccca ggggattgtc ttaatgagga gaaggagctg cactgaagtt 146400
gggctctaac gctggccttg aggccctccc tggggctgtt acgggtgaat tggctgtatt 146460
agatgtctct gctactttca taacagaact ctctgaggcg ggtctaagtg agacctgcca 146520
caatgaattc catttcctgt taaatagtgc gccagtgagg ctctggcaag gtgtgggcta 146580
gagatgcgac tcagttggat ctatctctca gaaggctacc ttgtaagtag agttccacag 146640
ctctgggaag tttgggcgtc ctcaccctgc aaagtttagg ttctgtggtg tagcgcactg 146700
cagttgattt gctttttgat agtggggagg gaagccggtt tggtccgtgt gggccagcgt 146760
ggtttggtgg agtcagcttc ataagagctg gggtcctgta ggtgtctacc agaggctggt 146820
ggctaagtag gcatgtgaac ttacatgtaa gtcagggatc cctaaaacct cactctgttt 146880
ttgtgctgaa agggcaaaaa ggttaacaca gggaagctca aatttgccat gtgcccgttt 146940
gaatatgtga gagtaaaaac ggcatttcat ccaaggctta tcgtagtcta gaacagtgca 147000
cagtgtggga aaaaggaaac aagggctctt cctggccctg ccaacccccct gcagagctgg 147060 aatccagctg tttgggctga ctaaaatcac ctttccaact tgacagtgag tgagaccagg 147120
ttgaacttgg tacagagacg ctgggctggc ccagatgact tcaggttact cctttccatc 147180
tcactggagc cattaaaaac tccaactcct cctcctcctc ctgctccatc agcatatctc 147240
tgagagagtc acgggggcct aagagtctct tttcactgcc tggtgagcag accagaagca 147300
gagggagaga ggcaaatgaa cagaggtcca agtaattcac atacttgact gtgacagtct 147360
ctgcttatta atgtaatctg ttttcctatt tgaaagggat gttatctgca aaactacctc 147420
aggccccaca tggcagcctg attctgaagc atcattgaat cttgtatgat attaagttga 147480
gaaagctgcc cttggatcca gtgtctaatc tttgtgaaga tcttacccca tacatagaat 147540
acaatgatca gaaatgtcaa gggttaggac agcacagccc tgacttctac ccaggctcac 147600
ttgttgcctg ctccctgacc cttgcaggat ctgcccaaag gtgaagcgcg tcttcaggtc 147660
aatagataat ctactagaga ttgtccccag agaacagaac tgggccctga ggcccaccgt 147720
tgccctttcc tgagagtccc agcccagtga aaggaacaca gttgacatgt tgttgaagcc 147780
ggagatgttg cctgtatgcg taaaagagct ctctgtttca ggctcatgta cagtcaggaa 147840
tggttccttc tcatccaact gcccatgcgc caatgatgct aatgacgaca cagccacccg 147900
gcggtcccca ggccgccctc gctcaaagtg cactacagcc cattccagtc tcgacaacag 147960
cgcatttccc ctatatgacg cacccttcag gtgaggcgtg tgtgtgcagg ggccgccggg 148020
gcaccccaaa gcattctgct cgcacaggtg gaatggcagg cagggccagt gcttcaagcc 148080
ccgcatttga gaactagcaa gacccgtcca ggagtgtgca caggagggac tgtgacgatc 148140
agttcagcat cagggcctga ggcttccggg agccgagtct gtgtgtgttc tgatggtata 148200
caggatttgg cttgatgaga agcagcagca gcagcaacag cagcctgatg catgcctagg 148260
actcagttgg ccttccttgt tatgacaggc tggacagggc agtgttttcc ttcctgagtc 148320
ccaaaagtct gacatgtggg gggttattac catggcagag tttgattgta gctctggaga 148380
agatactgct gagaaagcgc tgtggatgga ctggctttga gtgtagcgtt agccccagcc 148440
cctgaacagg ggagagcgcc ctgtgattgt gctctactac ttgatggctg ccatggcgat 148500
acttcacagt ctgacctgtt attctgaaag caatactggt gcttggctaa tatttgggga 148560
gggggtttgt taaggccttt ttttctaccc catgaacaag tcttctggga gttttatctg 148620
aagtggtttt acgtctgact ggtttgtttc tacccaccca cccaaccctc cccactttgg 148680
tgcagatggg agggggaaaa gcgaattcaa ttttgagttt tgttcagcta gcacgaggat 148740
agtttacaat catgtgctgc agagacacta ggctgatgtg tggtgttgcc agttttctgt 148800
ttcaatgttc gcttttcttt ttacagtaca agcccaccac caacagcagt tgtaaggctg 148860
ccctggagga accgaaaggc caaattccct cctcccttct actgcttcta ccaactggaa 148920
gcacagaaaa ctagaatttc atttattttg tttttaaaat atatatgttg atttcttgta 148980
acatccaata ggaatgctaa cagttcactt gcagtggaag atacttggac cgagtagagg 149040
catttaggaa cttgggggct attccataat tccatatgct gtttcagagt cccgcaggta 149100
ccccagctct gcttgccgaa actggaagtt atttattttt taataaccct tgaaagtcat 149160
gaacacatca gctagcaaaa gaagtaacaa gagtgattct tgctgctatt actgctaaaa 149220
aaaaaaaaaa aaaaaaatca agacttggaa cgccctttta ctaaacttga caaagtttca 149280
gtaaattctt accgtcaaac tgacggatta ttatttataa atcaagtttg atgaggtgat 149340
cactgtctac agtggttcaa cttttaagtt aagggaaaaa cttttacttt gtagataata 149400
taaaataaaa acttaaaaaa aatttaaaaa ataaaaaaag ttttaaaaac tgatcaagtt 149460
agtgtgtgtc tgtataagct acttctttgt aggatactta atatcaaagc aggtgtgcta 149520
agggtgcatt ttgaatatcc cggaaggtag ctgtgaaatg atttttcttc ttcaccctta 149580
gttctggttc aaggtatctc tagaaaaaga caagactgag ctattctctt tggtggatta 149640
gagatctgct tcaggaggag gaaggttggc cagagttggg cagcactgaa attccacatc 149700
ctcgggctga caccgattct gtaagcttcc tttttaatat ctcctgaacc aaaatgagtg 149760
tcattagctg gaagttccca attcgggcat ttttctactt taccagtagg gggcaggaga 149820
cactcagaaa aaaattgcaa taaagaaatc cagagggcat gaaggctgaa aagatacaaa 149880
gatgtacaaa gctgcttatt gacatggatg gactcataag catttgttag tattcccaga 149940
ttgcaacggg gaggacaaag ggaagagcga gtatttgggc agggcaagga ttttgtagag 150000
acaccatggt cttaatagag cctttaaata ttatgacagc aaatcaagat tctgaaaact 150060
ttttaattca catatagcaa tttgtacatt atagcaaaat ttgcattatt caagaataag 150120
ttacttgtac agtacataaa acaatacata aaaatttgcc aaataccttc tgcctataat 150180
gatacaagat gaatccactt tatgttatca caatgtgctg tatattctaa ccaaacacag 150240
gatgtcagat gtgtccttgt taatatactc gcaagttcct ctagcttgtg ggagatgtta 150300
gagctaacac atttgcagta agggacttag tcctgaatag aaagcatgaa ggaatctcag 150360
gcaaccctca gggaagagtc caaggccttg actttaggtt aagaaactgt tatgtaaaaa 150420
tagtgttctc tggcccaaga ttttaatgat tgctattcct ttttcctacg gtccagaaat 150480

```
gatcaaaggc agaagattta taccagataa agccatatgg attgctggtc taaaattcaa 150540

ggcaggttag ttgacttaat tctttggtgc tggtgactgt tagtttgtaa aagttcaata 150600

agtcagatga aggaagggat ggtgccggga gctgtcaagc tgtactggtg gggtctgtaa 150660

ttagagctaa ctggagggat catgatgtct actgtccagt ttggtgttga gccatggctc 150720

tcggtagaag ttgccggctg gggcctggtc aggactggaa ggagagtggt gggatgtgct 150780

gtgcctatgg tgggctagct gcagccagtg gggtgcctgc cccacactgc tgcccacccc 150840

ttcatcagct gattctgctc ccacataaag aaaggtgttg gcttagtgtc acttcttcct 150900

agagccatgg gagttttctg tcagcatgtt tttgagctgt cctggtaact tggacgggaa 150960

gcagtctgga ggtgggtgcc ttccaaatct ctgccacaga a                      151001
```

```
<210> SEQ ID NO 3
<211> LENGTH: 863
<212> TYPE: DNA
<213> ORGANISM: homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t

<400> SEQUENCE: 3

gtctgtcggg gctctctccc cgccccctcc ggatcctggg naagnacggn ggacggggtg     60

gagacaagtg ggccttggcc cccgcacccc tctgcgttcg tgtccgaggc ggcggcgggg    120

gctcccgaac tcccctgaaa tcgtggggct ccatgtggcc tccggcagcg ttccaccctc    180

ccccacctgg ggaagggaag gggtggggag tgcccggccc cgtcccggcc ttcctccttc    240

ccccgccaga cctctccggc gcgcgggtgg tggccgatcc gcattgctgt tcgaggccgc    300

agtggagaag gcgcctgtgg aacatcgagg tcgaaacagt aacaaaggac tgcctcagtc    360

tacgatttct tttgatggaa tctatgcaaa tatgaggatg gttcatatac ttacatcagt    420

tgttggctcc aaatgtgaag tacaagtgaa aaatggaggt atatatgaag gagtttttaa    480

aacttacagt ccgaagtgtg atttggtact tgatgccgca catgagaaaa gtacagaatc    540

cagttcgggg ccgaaacgtg aagaaataat ggagagtatt ttgttcaaat gttcagactt    600

tgttgtggta cagtttaaag atatggactc cagttatgca aaaagagatg cttttactga    660

ctctgctatc agtgctaaag tgaatggcga acacaaagag aaggaccctg cagcccctgg    720

atgcaggtga actcacagcc aatgagggaa ctggaggctt tgnaaaatga cgtatctaat    780

ggatggaacc caaagatatg tttcgtttaa tgaaaaaaat tatggcgcag gggccaccgt    840

tgaaagcagt ttatttcgga tac                                            863
```

```
<210> SEQ ID NO 4

<400> SEQUENCE: 4

000
```

<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
accaaagagt agttaatgga ggtgttc 27

<210> SEQ ID NO 6
<211> LENGTH: 19
<212> TYPE: DNA
<213> ORGANISM: Artificial sequence
<220> FEATURE:
<223> OTHER INFORMATION: Primer

<400> SEQUENCE: 6
agaaggtggg cgagaggaa 19

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
ctggccatcg ccttgccca 19

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccggctcgca cgccgggcgg 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
catacaccgg ctcgcacgcc 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ggcttcagcg acatggtgag 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgacctctgc ccaggccggg 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tgcatagatt ccatcaaaag 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
aagtatatga accatcctca 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttcacttgta cttcacattt 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctgtacttt tctcatgtgc 20

<210> SEQ ID NO 19
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 19
ctggattctg tacttttctc 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ctctccatta tttcttcacg 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tctttaaact gtaccacaac 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gagtcagtaa aagcatctct 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cagggctcca ggtccttctc 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gcatcccagg gctccaggtc 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tcttcattat atcgaaacat 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gctaactggt ttgcccttgc 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gtatttttct tcctcactcc 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tgctgtgtat ttttcttcct 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
gaaatctgaa gtgtgagaag 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cctccattaa ctactctttg 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggaacacctc cattaactac 20

<210> SEQ ID NO 32
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 32
ggcgatggcc agggaacacc 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gtagcgagaa ggtgggcgag 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agagttggga cctgactggt 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tggaagagag ttgggacctg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ggagctggag aaccatgagc 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gagacaggag ctggagaacc 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttgtgggata caaattctag 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ggaaccccac tgaccactga 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcttgaagcc tggaatcttt 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aacctaaaat cattcttaaa 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
agttgatcca tagattcaga 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ctggtacagt tgctgctgct 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgccactgg tacagttgct 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tttgcattgg gattcaatgt 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gaaggctttg gctgagagaa 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gtagtagaag gctttggctg 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tgacccacca tagatgggct 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtattgggt ataaaggttg 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gtcataggta ttgggtataa 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ggatgctgag actgataatg 20

<210> SEQ ID NO 52
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 52
acatgaggat gctgagactg 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aatttgggac atgcatacat 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtctccttgt tgtatggtaa 20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
tgaacaggac tgggtgcagg 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gactgctgct gtggactggc 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ctgactgtac atgagcctga 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ccattcctga ctgtacatga 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cagttggatg agaaggaacc 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
catgggcagt tggatgagaa 20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
accgccgggt ggctgtgtcg 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tttgagcgag ggcggcctgg 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gctgtagtgc actttgagcg 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
agactggaat gggctgtagt 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
gcgctgttgt cgagactgga 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggaaatgcgc tgttgtcgag 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ggcttgtact gaagggtgcg 20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gtggtgggct tgtactgaag 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
ctgttggtgg tgggcttgta 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
caactgctgt tggtggtggg 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gccttacaac tgctgttggt 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
ttcggttcct ccagggcagc 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ttctagtttt ctgtgcttcc 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
aataaataac ttccagtttc 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gaatcactct tgttacttct 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
cagcaagaat cactcttgtt 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tttataaata ataatccgtc 20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
aagttgaacc actgtagaca 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
atcggccacc acccgcgcgc 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
caaagggtta attaggatct 20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
cccaaagggt taattaggat 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggacagtca tttgatttgt 20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ctttgaggac agtcatttga 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctgacagaac aaatgatatg 20

<210> SEQ ID NO 85

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
tattgggtat aaaggcttga 20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggtattgggt ataaaggctt 20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ctcttttacg catacaggca 20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
aggaaggcca actgagtcct 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ggtcagacgg aagcagaacg 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ccacctggct gcggcgaagc 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gccgttgccg ttgctaccaa 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
ggcccataca ccggctcgca 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gcttcagcga catggtgagg 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
ggacattggc agccgcgggc 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
gattccatca aaagaaatcg 20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
caactgatgt aagtatatga 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
ccaaatcaca cttcggactg 20

<210> SEQ ID NO 98
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 98
ctcatgtgcg gcatcaagta 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
catttgaaca aaatactctc 20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ctgatagcag agtcagtaaa 20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gggccactcg agctttgtac 20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
aggaatatat ttattttccc 20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
cccatacgcg gtgaattctg 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tggagcccga tccaggctgg 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
agaagtggat cttgatggca 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ggagaaccat gagcagaggg 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
ggcccttctg aagacatgcg 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cactggatat ggaacccctc 20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gtgggataca aattctaggc 20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
actgaccact gatgaccacg 20

<210> SEQ ID NO 111
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 111
ctgggtctat gagttttagg 20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tggaataata ccagcttggg 20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
ggcatggcaa cagcttcagt 20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
taggagatgc agctggaata 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gaagcctgga atctttagcc 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ccctgcagga gagttctgcc 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ttcagaagta gaacttggct 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
caattttgtc tttgatcaaa 20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
tgttactaag tattgaaggg 20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
aagtgacctc aggtcccctc 20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
atgttgattt cctaacttgc 20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gtataaactg gagttggctg 20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
gtgcaaaaca aacaggctga 20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
gactggatac atcatatttg 20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
ggttgcacgc ctgggctcac 20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
tcataggtat tgggtataaa 20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
ttgattcact ggcatgggcg 20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
gatgatgctg gtcttgccgc 20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
atcattctag cattaccctg 20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
atactaaacc aggctgggcg 20

<210> SEQ ID NO 131
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 131
acatgcatac atcgcatgcg 20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
tagaaagaag ggcttgtctc 20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
cgcatactgc tgagcaaggg 20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tagctgaagg ctgagggtgt 20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
caccatgttg gctttgctgc 20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
actgggtgca ggatgacttc 20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
cgtggtaaat ggctgactgc 20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
ttggaggcag gtgtcatgga 20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tggcgcatgg gcagttggat 20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ctttgagcga gggcggcctg 20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gtcgagactg gaatgggctg 20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
attcctattg gatgttacaa 20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
atcttccact gcaagtgaac 20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
tatggaatta tggaatagcc 20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
gcaagaatca ctcttgttac 20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tgtagacagt gatcacctca 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
ggccaaggcc cacttgtctc 20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
cactgcggcc tcgaacagca 20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
aaattcctca ttttcttttc 20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
gttatagtaa tctgtaatca 20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
aggattgtaa aatgatacag 20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gtaggattgt aaaatgatac 20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
ttatatatgt aaattatatc 20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aaccactgat ttatacactt 20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
ttaaaaacca ctgatttata 20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
atatagcact ctgctgtatt 20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
taccaagctt gtggcttggg 20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ttataccaag cttgtggctt 20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
cctcgatgtt ccacaggcgc 20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
gagttcacct gcatccaggg 20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tccagttccc tcattggctg 20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
ggttccatcc attagatacg 20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ttaaacgaaa catatctttg 20

<210> SEQ ID NO 164

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164

gcccctgcgc cataattttt                                          20


<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165

ataaactgct ttcaacggtg                                          20
```